(12) United States Patent
Stanton et al.

(10) Patent No.: US 11,806,368 B2
(45) Date of Patent: Nov. 7, 2023

(54) STEM CELL SUBPOPULATIONS WITH DIFFERENTIAL GSTT1 EXPRESSION OR GENOTYPE

(71) Applicant: Agency for Science, Technology and Research, Singapore (SG)

(72) Inventors: Lawrence Stanton, Singapore (SG); Padmapriya Sathiyanathan, Singapore (SG); Simon Cool, Singapore (SG); Victor Nurcombe, Singapore (SG); Rebekah M. Samsonraj, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 609 days.

(21) Appl. No.: 16/875,486

(22) Filed: May 15, 2020

(65) Prior Publication Data

US 2020/0345782 A1 Nov. 5, 2020

Related U.S. Application Data

(62) Division of application No. 15/318,909, filed as application No. PCT/SG2015/050184 on Jun. 26, 2015, now abandoned.

(30) Foreign Application Priority Data

Jun. 26, 2014 (SG) .............................. 10201403640X

(51) Int. Cl.
*A61K 35/28* (2015.01)
*C12Q 1/6881* (2018.01)
*A61K 35/545* (2015.01)
*C12N 5/0775* (2010.01)

(52) U.S. Cl.
CPC ............ *A61K 35/28* (2013.01); *A61K 35/545* (2013.01); *C12N 5/0662* (2013.01); *C12N 5/0663* (2013.01); *C12Q 1/6881* (2013.01); *C12Y 205/01018* (2013.01); *C12Q 2600/158* (2013.01)

(58) Field of Classification Search
CPC ................................ A61K 35/28; C12N 5/0663
USPC ......................................................... 435/372
See application file for complete search history.

(56) References Cited

U.S. PATENT DOCUMENTS

2005/0019911 A1 1/2005 Gronthos et al.
2006/0269925 A1 11/2006 Nunes et al.

FOREIGN PATENT DOCUMENTS

| WO | WO-2005005601 A2 | 1/2005 |
| WO | WO-2007030693 A2 | 3/2007 |
| WO | WO-2012088225 A2 | 6/2012 |
| WO | WO-2012141971 A2 | 10/2012 |

OTHER PUBLICATIONS

Felix, 2006, Mutation Research/Fundamental and Molecular Mechanisms of Mutagenesis, 602:175-181.*
Aguilera, 2013, Human Immunology, 74:1470-1473.*
Wu, 2008, Stem Cells, 26:1484-1489.*
Gerber (2002, Nature, 417:954-958).*
Wu, H., et al., 'Copy number variant analysis of human embryonic stem cells', Stem Cells, 2008, vol. 26, pp. 1484-1489.
Shao, J., et al., 'Cytochrome P450 and glutathione S-transferase mRNA expression in human fetal liver hematopoietic stem cells', Drug Metabolism and Disposition, 2007, vol. 35, pp. 168-175.
Lustremant, C., et al., 'Human induced pluripotent stem cells as a tool to model a form of Leber congenital amaurosis', Cellular Reprogramming, 2013, vol. 15, pp. 233-246.
Okada, R., et al., 'Direct and rapid genotyping of glutathione-s-transferase M1 and T1 from human blood specimens using the SmartAmp2 method', Drug Metabolism and Disposition, 2010, vol. 38, page.
Aguilera, I., et al., 'Clinical relevance of GSTT1 mismatch in solid organ and hematopoietic stem cell transplantation', Human Immunology 2013, vol. 74, pp. 1470-1473.
Lordelo, G. S., et al., 'Association between methylene tetrahydrofolate reductase and glutathione S-transferase M1 gene polymorphisms and chronic myeloid leukemia in a Brazilian population', Genetics and Molecular Research, 2012, vol. 11, pp. 1013-1026.
Fujimoto et al., Drug Metabolism & Diposition, 35 (12), 2196-2202 (2007).
International Search Report and Written Opinion for PCT/SG2015/050184 dated Oct. 7, 2015 (Applicant—Agency for Science, Technology, and Research) (13 Pages).
Kim, S-H. et al., J Periodontal Implant Sci 2011;41:192-200.
Felix, R. et al. (2006) GSTM1 and GSTT1 polymorphisms as modifiers of age at diagnosis of hereditary nonpolyposis colorectal cancer (HNPCC) in a homogeneous cohort of individuals carrying a single predisposing mutation. Mutation Research/Fundamental and Molecular Mechanisms of Mutagenesis. 602(1-2): 175-181.
Buchard, A. et al., Multiplex PCR detection of GSTM1, GSTT1, and GSTP1 gene variants, Journal of Molecular Diagnostics, 9(5):612-617 (2007).
Ito, M. et al., GSTT1 is upregulated by oxidative stress through p38-MK2 signaling pathway in human granulosa cells: possible association with mitochondrial activity, Aging, 3(12):1213-1223 (2011).
Teixeira, R.L.F. et al., Tuberculosis pharmacogenetics: state of the art, Tuberculosis—Current Issues in Diagnosis and Management, InTech, (2013).

(Continued)

*Primary Examiner* — Valarie E Bertoglio
(74) *Attorney, Agent, or Firm* — Polsinelli PC

(57) ABSTRACT

A method for providing a sub-population of stem cell or plurality of stem cells by determining or modulating GSTT1 expression level or genotype is disclosed together with uses of the stem cells.

5 Claims, 35 Drawing Sheets

Specification includes a Sequence Listing.

(56) References Cited

OTHER PUBLICATIONS

Rodriguez-Mahou, M. et al. (2007) Antibodies Against Glutathione S-Transferase T1 (GSTT1) in Patients With GSTT1 Null Genotype as Prognostic Marker: Long-Term Follow-Up After Liver Transplantation. Transplantation. 83(8): 1126-1129.
Yen et al., Cell Transplant., 2011, vol. 20, pp. 1529-1545.

* cited by examiner

| GST Classes | Homo sapiens GST Class Members |
|---|---|
| Alpha | GSTA1, GSTA2, GSTA3, GSTA4, GSTA5 |
| Kappa | GSTK1 |
| Mu | GSTM1, GSTM1L, GSTM2, GSTM3, GSTM4, GSTM5 |
| Omega | GSTO1, GSTO2 |
| Pi | GSTP1 |
| Theta | GSTT1, GSTT2 |
| Zeta | GSTZ1 |

| Table 1 | Frequencies of homozygous deletion | | |
|---|---|---|---|
| Locus | Frequency (range) | Population | |
| GSTT1 | 0.24 | African American (United States) | 32 |
| | 0.38 | African (Nigeria) | 42 |
| | 0.16 | Caucasian (Australia) | 40 |
| | 0.11-0.18 | Caucasian (European) | 24, 42, 63, 64 |
| | 0.15-0.16 | Caucasian (United States) | 31, 32 |
| | 0.58 | Chinese (Singapore) | 65 |
| | 0.16 | Indian (Singapore) | 65 |
| | 0.38 | Malay (Singapore) | 65 |

| Gene | Slow Growers | | | Fast Growers | | |
|---|---|---|---|---|---|---|
| | B | D | F | A | C | E |
| GSTT1 | 446.7 | 534.1 | 484.2 | -1.8 | 0.1 | 387.2 |

| T cell : hMSC ratio | Proliferation of T cells (%) | |
|---|---|---|
| | Fast growing | Slow growing |
| 1:2 | 5.42 ± 0.78 | 4.96 ± 0.11 |
| 1:1 | 7.49 ± 0.25 | 18.1 ± 1.02 |
| 2:1 | 21.34 ± 1.27 | 34.51 ± 0.70 |
| 4:1 | 47.92 ± 1.85 | 58.53 ± 2.88 |
| 8:1 | 68.4 ± 1.58 | 73.77 ± 0.43 |
| 16:1 | 79.3 ± 1.58 | 82.41 ± 1.35 |
| 32:1 | 85.26 ± 0.52 | 83.45 ± 1.79 |
| Negative control | 1.77±0.44 | |
| Positive control | 85.23±0.19 | |

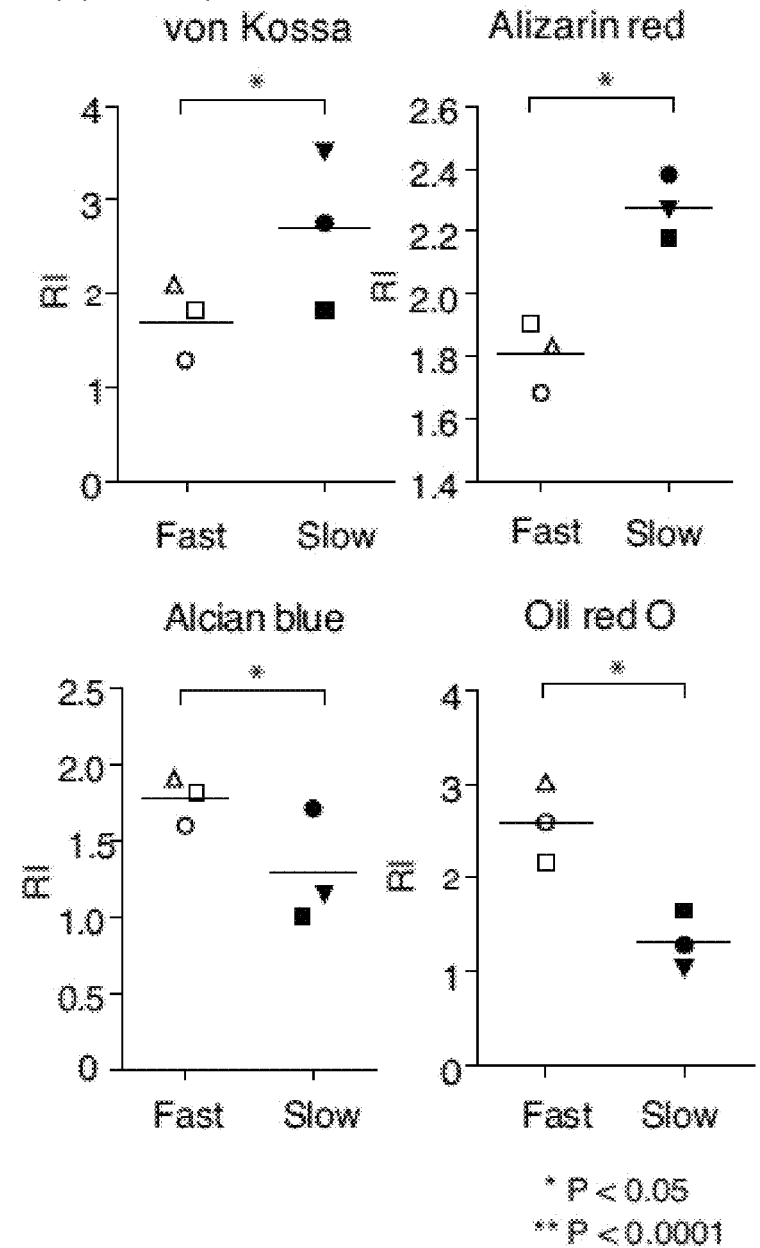

(i)

(ii)

(*P = 0.002, ANOVA (post-test Fisher LSD))

SEQUENCE LISTING

<160> NUMBER OF SEQ ID NOS: 15

<210> SEQ ID NO 1
<211> LENGTH: 8146
<212> TYPE: DNA
<213> ORGANISM: Homo sapiens

<400> SEQUENCE: 1

```
actggagttt gctgactccc tctggtttcc ggtcaggtcg gtcggtcccc actatgggcc      60
tggagctgta cctggacctg ctgtcccagc cctgccgcgc tgtttacatc tttgccaaga     120
agaacgacat tcccttcgag ctgcgcatcg tggatctgat taaaggtagg tccagcctcg     180
ggtttgggga accgaaaagt caggaagggg acaggtaggc atacatagct tagggaactt     240
ctcccagcgc caccttcttc ctggggccat tgctggtctg gtttggagac cgaacagaga     300
aaggtgagcc agcagggaga tccaagagtc ggggctcccc aaaactctgc tcggtctcac     360
ggaatagacc acggggttcc cctgaggccg aataaagggg tggggatcat gaagagaagc     420
cagacaggag gacaaaaacg ggcgcagctg ggtgcagggg cacacgcctg tagtcccagc     480
aactcgagag gctggggtgg gaggatcgct tgagcccagg aattccaggc cgcagtgcac     540
```

```
tatcatggtg cccttgaata gccactgcac tcccgtcagg gcaatctagc gagacccgt      600 cttaaaaaaa aaaacaaaa aaaaacaaaa tgaaagcagg tgtgacctcg gcctagggaa      660
aggtgggatg agagaggtca agggtgccaa gtgtagagac tgggacagcg tcaagtccct      720
tctttatggc ccagctgctg agattctgca acagcaaaca gctcaggacg tgactttcca      780
tccctgccct ctgcactcgt ccagtctgca ttggggtccc tctttgtccc ttccttcctc      840
tgttcctcct gttttgcctc tgaccttgtc cttgtccttt ttttttgag acagagtctt      900 gcttttgctt tgttgcagtg cagtggcacg atctcgaat cactgcaacc accacctccc      960
gggttcaagc aattctcctg cttcagcctc ctgagtagct agattacaaa tgtgtgccac     1020
tatgtctggc taatttttt gtattttaa cagagatggg atttcacaat tttggtcagg     1080
ctgttctcga actcctgaca tcaaatgatc tgccggctta gcctcccaaa gtgctgggat     1140
tacaggcatg agccactgtg cctggcccaa ggcattttgt ttatttgttt gtttgttttt     1200
gagacggagt ctcgctctgt cgcccaggct ggagtgcagt ggcaggatca cagctcactg     1260
caacctctgc cgcccgaaac cttgtcctct gcctcttgtt cctgctgggg aggtaggttg     1320
ccccaggctg ctgatgctgg aagcagcagg gggaccctgg ggcttgatga gccctacacc     1380
ctgttttgtt tctctagcat gcctccaagg cccttgagga ctcagctggc aggcccaggc     1440
ccaggcccag tgcagggtgg ggtagtagga ggggttggaa gcagaatcca ggtatggctg     1500
gtggggcaag taaggcgact ctacttggct aagccttctg cccagggctc ccactccatg     1560
gctggccctc tgcctgaaac ttctccacat aatctcttct gcaaactgcc cactgtcctg     1620
cgcaaggact tcctctgcag agtgtggagt agaggaaagg gaatggggga caagaggacg     1680
tccaagctgg ttgtcaaatg tagtggtgca gagggaagtg tgttttccca ggagacagag     1740
gagggttttc ctggtgaagg aacagtctga agggagggtg aagagagggt agcaggctgg     1800
gcatggtggc tcacacctgt aatcccagca ctttgggagg ccgaagtagg aagattactt     1860
gaggccagta gttcaagacc agcctgggca acatagtgag accccaactg taaggggaat     1920
aaaagtttgg ggcacagggg gtggtagcag gtatgctaca cacagctcca cagtgcccag     1980
ggcagggtga acaaagggac atggtggggc cagtagaagt tgcttctaag taggtagata     2040
ccagaaaaag accacttctc tgtgtttcat gaccctgcct tagaattaat ggtggaaggg     2100
acaaggtagt cagtcccctc aggtgaccta tcgtgcagct tggggtgctc tgattgtgag     2160
ttcatgaagc tggcaatagt ggaaagagga gatgggtagg gtgcatgcaa aggtccagga     2220
accacaccct gcacagtgag ctctgttgca gaggggcagc ctgtgggagg aggctgtgcc     2280
tacaggactt agcaaggggt gttgtctatt ttgtaccagc cggtggagtg gtctcctcct     2340
cctcccgcag gggcccttcc agtctttgcc aaccaggagt gcagactggt gggaagaaga     2400
actgtgaaac tggggccaga gcattgcagg gaggggcaca ggccatggcg ggctcagcgt     2460
tctcctccca ccaccacca tgctggactc ttcccaggtc agcacttaag cgatgccttt     2520
gcccaggtga accccctcaa gaaggtgcca gccttgaagg acggggactt caccttgacg     2580
gagaggtaac tgggaccta ggactgctgc caggcctgct ggaaccatcc tgttctaacc     2640
ctctatttca tagacaagga aactaaagtc ttcagaggca gagagtctct gtgccccgca     2700
tcctgcagag agtcagtact ggaccccagg cccttgcctt cctgctattc cagttcaccc     2760
tgatgattag aaaagcaaat atctactta cttccacacc agtgctttgg ttgctggtga     2820
gtggtgagag tatccttgag acagggtagg ccagaggacg atggcagctt tgcccaccgt     2880
```

```
ggggcaggcc tctggccaag cttgtgtggc gatggctcag tggcatctgg gctgccggt    2940
ggctccatct ctgggctgca gcttcccagg atgggtcttc cccatggaag agccaccaga   3000
tatggacgtc ttacatcaca gctggtccca agaagttgaa tcctcttcag gaaaagccaa   3060
tctttcccca gttctgcccc ttttgtcacc agagtcaccc ttcccctaac aagaacctgg   3120
agtttgtgct ttaaagctca tctctgaaat ctcaggatgg acgcacctcc gatgaattcc   3180
tctgacattc tgccagggcc cgtcttcctc cctggtgccc caggtgtcct gagtccttgt   3240
gtcactcagc gttgtgaccc ccaggtacca gccagagtca atgtgcaatc tctgcctctg   3300
tcactactct caccttcagg tctgtggctc acagagacct gcagccctcc tcagaggtgg   3360
cttgaacaat tggctgggag caaaaggagc tcctgggcac cctgcacaga caacggagtc   3420
gttaagctgg gacacgtgtg tagccccagc ttaaaagaga atataggccc gtggcagata   3480
cagaggtttt ctgcccttt ggcctgcatg cccaaccttt gggaaacccc aagttcctga    3540
aagcttttct gtgtctccaa atggacacat cctgtgtcct tccaggtcca tgctcatctc   3600
atcaccatgg cggccctcaa aacccaggga aggaggagag tgccaggggg ccttgtctgt   3660
tctgttgttc taggatcctg cagctgcagg agtgcttcct gagtggtact ttaggaagcc   3720
aaactacccc agtcagctta gataggagct gattcttggc agaaagaatg acagaaagaa   3780
caaagggaca cggaagcctt tttgaacagt caggccatca gaggctggtc ggaatcccag   3840
cagatgagag tggataccga atggaaagaa ctgagcttct ttaaagctca gctttgatgc   3900
cccgttctcc tggaagctct ctctggttct ctgatcagaa actgtctcta aacatttggc   3960
aagacattct gttgtgggat tttgcctggt ggtaggaaaa gcttgggtat tagcctcaga   4020
aagattctca gctctgccat taagagctgt gtgccctagg gcaagtctct gcctttctaa   4080
gcctggtttt cttctctgga aaatgaggct aatactttgg caaattgtca gaaaggttaa   4140
agaagtgtgc tgggcacagt ggttcatgcc tataatgcca gcgctttggg atgccaaggc   4200
tggaggattg cttgaggata ggagtttaag accagcctgg caatacagtg agatcccatc   4260
tctacaaaaa agaaaaaagg tagccaggca tggtggtgca ctcctataaa aattgaagct   4320
gcagtgagct gagactgcac cactgcactc cagcctgggt gactgaggaa gaccttgtct   4380
ccaaaaaaaa aaaaaaaaa aaaaaaaaa aaggccaggt gcggttgctt atacgtgtaa    4440
tcacagcact ttgggaggcc gaggcaggca gatcacaagg tcaggagttc gagaccatcc   4500
tggctaatat ggtgaaaccc catctctact aaaactacaa aaattagcc aggcatggtg     4560
gcacgcacct gtagttccag ctacttggga ggctgaggca ggagaatcac ttgaacccgg   4620
gaggtggagg ttgcagtgag ccaagatcgc accactgcac tccagcctga gcgacagagc   4680
gagactccgt atcaaaaaaa aaaaaaagcg actatgtatg aaatacccag cacagtgccc   4740
ttcccttacc catcatgacc cccacaccca cagtgtggcc atcctgctct acctgacgcg   4800
caaatataag gtccctgact actggtaccc tcaggacctg caggcccgtg cccgtgtgga   4860
tgagtacctg gcatggcagc acacgactct gcggagaagc tgcctccggg ccttgtggca   4920
taaggtgagg ctgggaatgt gggggggcggc agcgagagca ttccccaaag gtgttcaggc   4980
accagtctct tcttttcagt tttggattat ttctactgac ctgtcttgc cttcacagat     5040
tctttcctct gttgtgccaa attgctatta agcccatcca atacattctt tgtttgagat   5100
atgtattttt cagctctgga aattccattt ggttgttttt tagaatttcc acttctctga   5160
tgaaattcac catctgttca tccatttat ctgtcttttc ttgtaaattc tttaacatat    5220
ttatcactgt tacctaaaaa tctttgtcaa ctaatttcaa cacgtaggtg ttctgtgggt   5280
```

```
ctggttttttt tgttttgttt tgtttttgag atggggtctc actctgtcac ccaggctgag   5340
tgcaatggtg cgatctcagc tcactgcaac ctccacctcc caggctcaag cgattctcct   5400
gcctcagcct cctgcgtagc tgggattaca ggcacccacc agcacacctg gctaactttt   5460
gttatttgta gtggagaccg ggtttcacca tgttggccag gctggtttcg aactctccac   5520
ctgaagtgat tcgtcctcct tggcttccca aagtgttggg attacaggca tgagccacca   5580
tacccagcct acgggtctat ttctattgat tgttgttttc tccctcttga ttatgggtca   5640
catttgcctg cttctttgca tgtctcatga tgtattatca ttattttta ttttttttgag   5700 acggactctc actccattgc ccaggctggc gtgcaatggc acgatcttgg ctcactgcaa   5760
cctccgcctc ctgggttcaa gcgattctcc cacctcagcc tcccaagtag ctagaattac   5820
aggcacctgc catcatgcct ggctaatttt tgtattttgg tagagacagg gtttcaccat   5880
gttggccagg ctggtcttga actcctgacc tcaggtgatc ctcccatctc ggcctcccaa   5940
agtgctggga ttgtaggcat gagccaccat gcccggcctc atgatgtatc cttgtgtgcc   6000
agacattatg ataaaagaag agcagagatt gaattgcata ataaacaccc ccaagaaagg   6060
gcttgcactt ccctgtgtca ggtagccagg atgtgaggct gttctcttct aagctaatca   6120
ggaggtgggc tgggttgcag gtttagttgg tttcagttta tctttggttt caaatatctt   6180
gaatgtgaga tcaggtcact agctcagtct agcatggctt tggaatctaa tcaccaacta   6240
cgatgttgcc tgtaagatct ctctgctttt catccctgcc cccagttccc aaactgctgc   6300
tcagtcagaa aagcccatgc ctgtgacagt ctttctccca gcctgcttgg gcccaaggaa   6360
atgaaattgg aatgaaagta gctcatctag gaacggctta tgcctctctg gaatttagtt   6420
catttagtca agtgctgtcc gatagaagta taaagtgagc cacatacgta attttaaatt   6480
ttctagtagg cacatttaaa aagtaaaaag agtccaggca cagtggctca tgccaataat   6540
cctagcactt tgggaggcca aggcagtgga tcacctgagg tcaggagttc gagaccagcc   6600
tggtcaacat ggggaaacct tgtctctact aaaaccacaa aaattagcca ggcttggtgg   6660
cctgtgccta taatcccagc tactcaggat gctgaggcag gagaattgct tgaacccagg   6720
gggcaaagtt ggcagtgtgc cgagatggtg ccacttcact ccagcctggg tgacagagct   6780
gaacactgtc tcaaaagaaa aaaaaaagt aaaggaaat tgatatattt tacttaaccc   6840
aatgtgttga gaatattatc attttggcca acaagtacaa gaaaagatgc ttggccgggc   6900
gcggtggctc acgcctgtaa tcccagcact ttgggaggcg gaggcaggca gatcacaagg   6960
tcaggagatt gagaccatcc tggctaacac agtgaaaccc tgtctctact aaaaataaaa   7020
aaaaaattag ctgggcgtgg tggcgggcac ctgtagtccc agctactcgg gaggctgagg   7080
caggagaatg gcgtgaaccc aggaggcgga gcttgcagtg agccgagatc accccactgc   7140
actccagcct gggcgagaga gcaagactca gtctcaaaaa aaaaaaaaaa agaaaagatg   7200
ctcagcatca ctaatcatta gggaaatgca aatcaaaact aactccctac tccagtaact   7260
cccgactttg cctgcccaat ccccaggtga tgttccctgt tttcctgggt gagccagtat   7320
ctccccagac actggcagcc accctggcag agttggatgt gaccctgcag ttgctcgagg   7380
acaagttcct ccagaacaag gccttcctta ctggtcctca catctcctta gctgacctcg   7440
tagccatcac ggagctgatg catgtgagtg ctgtgggcag gtgaacccac taggcagggg   7500
gccctggcta gttgctgaag tcctgcttat gctgccacac cgggctatgg cactgtgctt   7560
aagtgtgtgt gcaaacacct cctggagatc tgtggtcccc aaatcagatg ctgcccatcc   7620
```

-continued

| | |
|---|---|
| ctgccctcac aaccatccat ccccagtctg tacccttttc cccacagccc gtgggtgctg | 7680 |
| gctgccaagt cttcgaaggc cgacccaagc tggccacatg gcggcagcgc gtggaggcag | 7740 |
| cagtggggga ggacctcttc caggaggccc atgaggtcat tctgaaggcc aaggacttcc | 7800 |
| cacctgcaga ccccaccata aagcagaagc tgatgccctg ggtgctggcc atgatccggt | 7860 |
| gagctgggaa acctcaccct gcaccgtcc tcagcagtcc acaaagcatt ttcatttcta | 7920 |
| atggcccatg ggagccaggc ccagaaagca ggaatggctt gcctaagact tgcccaagtc | 7980 |
| ccagagcacc tcacctcccg aagccaccat ccccaccctg tcttccacag ccgcctgaaa | 8040 |
| gccacaatga gaatgatgca cactgaggcc ttgtgtcctt taatcactgc atttcatttt | 8100 |
| gattttggat aataaacctg ggctcagcct gagcctctgc ttctaa | 8146 |

<210> SEQ ID NO 2
<211> LENGTH: 1076
<212> TYPE: DNA
<213> ORGANISM: Homo sapiens

<400> SEQUENCE: 2

| | |
|---|---|
| actggagttt gctgactccc tctggttttcc ggtcaggtcg gtcggtcccc actatgggcc | 60 |
| tggagctgta cctggacctg ctgtcccagc cctgccgcgc tgtttacatc tttgccaaga | 120 |
| agaacgacat tcccttcgag ctgcgcatcg tggatctgat taaaggtcag cacttaagcg | 180 |
| atgcctttgc ccaggtgaac ccctcaaga aggtgccagc cttgaaggac ggggacttca | 240 |
| ccttgacgga gagtgtggcc atcctgctct acctgacgcg caaatataag gtccctgact | 300 |
| actggtaccc tcaggacctg caggcccgtg cccgtgtgga tgagtacctg gcatggcagc | 360 |
| acacgactct gcggagaagc tgcctccggg ccttgtggca taaggtgatg ttccctgttt | 420 |
| tcctgggtga gccagtatct ccccagacac tggcagccac cctggcagag ttggatgtga | 480 |
| ccctgcagtt gctcgaggac aagttcctcc agaacaaggc cttccttact ggtcctcaca | 540 |
| tctccttagc tgacctcgta gccatcacgg agctgatgca tcccgtgggt gctggctgcc | 600 |
| aagtcttcga aggccgaccc aagctggcca catggcggca gcgcgtggag gcagcagtgg | 660 |
| gggaggacct cttccaggag gcccatgagg tcattctgaa ggccaaggac ttcccacctg | 720 |
| cagaccccac cataaagcag aagctgatgc cctgggtgct ggccatgatc cggtgagctg | 780 |
| ggaaacctca cccttgcacc gtcctcagca gtccacaaag catttcatt tctaatggcc | 840 |
| catgggagcc aggcccagaa agcaggaatg gcttgcctaa gacttgccca gtcccagag | 900 |
| cacctcacct cccgaagcca ccatccccac cctgtcttcc acagccgcct gaaagccaca | 960 |
| atgagaatga tgcacactga ggccttgtgt cctttaatca ctgcatttca ttttgatttt | 1020 |
| ggataataaa cctgggctca gcctgagcct ctgcttctaa aaaaaaaaaa aaaaaa | 1076 |

<210> SEQ ID NO 3
<211> LENGTH: 240
<212> TYPE: PRT
<213> ORGANISM: Homo sapiens

<400> SEQUENCE: 3

Met Gly Leu Glu Leu Tyr Leu Asp Leu Leu Ser Gln Pro Cys Arg Ala
1               5                   10                  15

Val Tyr Ile Phe Ala Lys Lys Asn Asp Ile Pro Phe Glu Leu Arg Ile
            20                  25                  30

Val Asp Leu Ile Lys Gly Gln His Leu Ser Asp Ala Phe Ala Gln Val
        35                  40                  45

Asn Pro Leu Lys Lys Val Pro Ala Leu Lys Asp Gly Asp Phe Thr Leu
    50                  55                  60

Thr Glu Ser Val Ala Ile Leu Leu Tyr Leu Thr Arg Lys Tyr Lys Val
65                  70                  75                  80

Pro Asp Tyr Trp Tyr Pro Gln Asp Leu Gln Ala Arg Ala Arg Val Asp
                85                  90                  95

Glu Tyr Leu Ala Trp Gln His Thr Thr Leu Arg Arg Ser Cys Leu Arg
            100                 105                 110

Ala Leu Trp His Lys Val Met Phe Pro Val Phe Leu Gly Glu Pro Val
            115                 120                 125

Ser Pro Gln Thr Leu Ala Ala Thr Leu Ala Glu Leu Asp Val Thr Leu
        130                 135                 140

Gln Leu Leu Glu Asp Lys Phe Leu Gln Asn Lys Ala Phe Leu Thr Gly
145                 150                 155                 160

Pro His Ile Ser Leu Ala Asp Leu Val Ala Ile Thr Glu Leu Met His
                165                 170                 175

Pro Val Gly Ala Gly Cys Gln Val Phe Glu Gly Arg Pro Lys Leu Ala
            180                 185                 190

Thr Trp Arg Gln Arg Val Glu Ala Val Gly Glu Asp Leu Phe Gln
            195                 200                 205

Glu Ala His Glu Val Ile Leu Lys Ala Lys Asp Phe Pro Pro Ala Asp
    210                 215                 220

Pro Thr Ile Lys Gln Lys Leu Met Pro Trp Val Leu Ala Met Ile Arg
225                 230                 235                 240

<210> SEQ ID NO 4
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 4
tcgggaaccc agaaggcaca gacag                                    25

<210> SEQ ID NO 5
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 5
tacaagcact cccacttcat ctgga                                    25

<210> SEQ ID NO 6
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 6
tccagttcag ggcagtagtg actca                                    25

<210> SEQ ID NO 7
<211> LENGTH: 25
<212> TYPE: DNA
<213> ORGANISM: Artificial sequence
<220> FEATURE:
<223> OTHER INFORMATION: Synthetic sequence: Oligonucleotide probe

```
<400> SEQUENCE: 7
tctcataatg ccatcaggtt tgggc                                          25

<210> SEQ ID NO 8
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 8
tcgtgccttg tcattttatt tggag                                          25

<210> SEQ ID NO 9
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 9
gccggagacc tagatgtcat tgttt                                          25

<210> SEQ ID NO 10
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 10
acgtgcgcga gcgccagcgc accca                                          25

<210> SEQ ID NO 11
<211> LENGTH: 25
<212> TYPE: DNA
<213> ORGANISM: Artificial sequence
<220> FEATURE:
<223> OTHER INFORMATION: Synthetic sequence: Oligonucleotide probe

<400> SEQUENCE: 11
tggtcttggt ggaaactttg ctgcc                                          25

<210> SEQ ID NO 12
<211> LENGTH: 25
<212> TYPE: DNA
<213> ORGANISM: Artificial sequence
<220> FEATURE:
<223> OTHER INFORMATION: Synthetic sequence: Forward primer

<400> SEQUENCE: 12
tcttttgcat agagaccatg accag                                          25

<210> SEQ ID NO 13
<211> LENGTH: 25
<212> TYPE: DNA
<213> ORGANISM: Artificial sequence
<220> FEATURE:
<223> OTHER INFORMATION: Synthetic sequence: Reverse primer

<400> SEQUENCE: 13
ctccctactc cagtaactcc cgact                                          25

<210> SEQ ID NO 14
```

```
<211> LENGTH: 24
<212> TYPE: DNA
<213> ORGANISM: Artificial sequence
<220> FEATURE:
<223> OTHER INFORMATION: Synthetic sequence: Forward primer

<400> SEQUENCE: 14
gaagcccaag aatgggtgtg tgtg                                            24

<210> SEQ ID NO 15
<211> LENGTH: 22
<212> TYPE: DNA
<213> ORGANISM: Artificial sequence
<220> FEATURE:
<223> OTHER INFORMATION: Synthetic sequence: Reverse primer

<400> SEQUENCE: 15
tgtccccatg gcctccaaca tt                                              22
```

STEM CELL SUBPOPULATIONS WITH DIFFERENTIAL GSTT1 EXPRESSION OR GENOTYPE

CROSS REFERENCE TO RELATED APPLICATIONS

This application is a Division of U.S. patent application Ser. No. 15/318,909, filed on Dec. 14, 2016, which is a U.S. National Stage Application filed under 35 U.S.C. 371 of PCT Application No. PCT/SG2015/050184, filed on Jun. 26, 2015, which claims the benefit under U.S.C. § 119(e) of Singapore Patent Application Serial No. 10201403640X, filed on Jun. 26, 2014, each of which is incorporated herein by reference in its entirety.

FIELD OF THE INVENTION

The present invention relates to methods involving the determination of the GSTT1 genotype of cells or the determination of the level of GSTT1 expression in cells, and to cells modified to express reduced levels of GSTT1.

BACKGROUND TO THE INVENTION

Glutathione-S-transferase theta 1 (GSTT1) is a metabolic enzyme that belongs to the GST superfamily. This family of phase II metabolic proteins is classified into 7 classes according to their sequence and structure. They catalyze the conjugation of reduced glutathione to electrophilic and hydrophobic xenobiotics for detoxification (FIGS. 1A and 1B). They also remove reactive oxygen species, biosynthesize and metabolize prostaglandins and steroids.

Genetic polymorphism within GST genes is common in the world population with the members having either point mutations or a complete loss of gene. GSTT1 homozygous deletion is prevalent in approximately 20-60% of most populations (FIG. 2). Homozygous deletion is caused by homologous recombination of two highly similar stretches of sequence flanking the gene. Studies have shown a weak association between GST polymorphism and DNA damage or DNA repair leading to disease risk such as cancer. However, many other studies have shown no disease association. Thus, there is no conclusive data on GSTT1 involvement in cancer and other diseases.

Several members of the GST family have been ascribed non-enzymatic roles. A, P and M classes are involved in signaling pathways that control cell cycle and differentiation. They sequester members of MAPK pathways which are involved in cell survival and cell death. A recent study has shown that oxidative stress induces an increase in GSTT1 expression possibly through the p38 signaling pathway, suggesting its involvement in cell cycle control.

Finding an ideal stem cell for clinical applications with high self-renewal capacity and multipotency has been a challenge.

Despite a considerable body of research over the last decade, and an increasing pace of IND submissions to the US FDA, there is still no generally accepted definition of what constitutes a mesenchymal stem (or stromal) cell (MSC) (Keating, 2012 Cell Stem Cell 10(6):709-716; Mendicino et al., 2014 Cell Stem Cell 14(2):141-145). As Keating (2012) has succinctly pointed out, MSCs, as they currently tend to be defined, are "a phenomenon of in vitro culture", which makes it difficult to predict how they will perform when transplanted back into the body. There is thus still a pressing need to carefully correlate the in vitro characteristics of particular populations of MSCs with their activity to form appropriate tissue when transplanted back in vivo. In view of the burgeoning interest in the clinical utility of MSCs, there clearly needs to be a further refinement in the protocols used to generate them; clearly plastic adherence, surface marker expression and differentiation potential (Dominici et al., 2006 Cytotherapy 8: 315-317) are not sufficient criteria for selection, and other features, including the secretion of growth factors and immunomodulatory status, must be taken into account, and then cross-correlated with in vivo outcomes. The present inventors are sought to address this need to revise the definition of MSCs.

Human MSCs (hMSCs) are generally considered to consist of a heterogeneous subpopulations of adherent cells that can be obtained from various adult tissues and, under defined culture conditions, demonstrate the ability to self-renew as well as retaining the capacity to differentiate into specialized cells such as osteoblasts, chondrocytes, adipocytes, and myoblasts (Pittenger et al., 2009 Science 284: 143-147). However, the ability to survive and differentiate in vitro may no longer be regarded as predictive of the ability to repair tissue as the in vitro characteristics of hMSCs do not entirely correlate with in vivo efficacy (Ko et al., 2008 Tissue Eng Part A 14:2105-19; Bueno and Glowacki, 2009 Nature Reviews Hematology 685-697; Rai et al., 2010 Biomaterials 7960-70).

Clearly, the postulates given by the International Society for Cellular Therapy (ISCT) for defining an MSC (that include adherence to plastic, expression of CD markers, and multipotency in vitro) must be revised in order to address the efficacy problems that arise due to the heterogeneous nature of the cultures. Even if using MSCs generated as single-cell-derived colonies, there are problems with persistent heterogeneity in the cultures of the cells (O'Connor et al., 2011 BMC Proc 5 Suppl 8: 014). Several groups in recent years have attempted to isolate homogeneous cell populations by enriching cells for one or more surface markers that are known to be linked to fundamental mesenchymal stem cell function (Simmons and Torok-Storb 1991 Blood 78:55-62; Gronthos et al. 1999 Journal of Bone and Mineral Research 14:47-56; Deschaseaux et al., 2003 British Journal of Haematology 122:506-517; Buehring et al., 2007 Hematopoietic Stem Cells Vi 262-271; Gang et al., 2007 Blood 109:1743-1751; Battula et al., 2009 Haematologica—the Hematology Journal 94:173-184; Tormin et al., 2011 Blood 117:5067-5077). While these approaches are helpful in isolating hMSCs from the haematopoietic cells, they do not fully distinguish naïve cells from functionally mature populations. Another strategy for the isolation and preparation of uniform populations of hMSCs include size-based sorting to obtain cells that are highly clonogenic and multipotential (Colter et al., 2001 Proceedings of the National Academy of Sciences of the United States of America 98:7841-7845; Smith et al., 2004 Stem Cells 22:823-831); yet another that has emerged is the secretome of these cells. MSCs secrete a broad array of bioactive paracrine factors that play critical roles in engraftment and wound healing (Caplan and Dennis 2006 Journal of Cellular Biochemistry 98:1076-1084; Caplan and Correa, 2011 Cell Stem Cell 9:11-15). Such secretory profiling has also been hypothesised as a means of predicting of hMSC potency (Caplan 2009 Journal of Pathology 217:318-324; Prockop et al., 2010 14: 2190-2199).

SUMMARY OF THE INVENTION

The present inventors have unexpectedly found that GSTT1 expression is inversely correlated with growth rate i.e. cell doubling time and/or tissue forming potential. This discovery enables the identification, separation, enrichment and/or selection of cells having relatively fast growth rates. In the context of stem cells this allows for the provision of cell populations useful in the generation of tissues in vitro and in vivo. As such, tissues may be generated in vitro which are suitable for implantation into patients or cells identified or selected by the methods of the invention may be administered or implanted into patients in order to provide a medical treatment, e.g. the regeneration of tissue.

Accordingly, in one aspect, the present invention provides a method for identifying a stem cell or plurality of stem cells, the method comprising determining the level of GSTT1 expression in said stem cell or plurality of stem cells.

Advantageously, the method can be used to identify stem cells having improved/enhanced growth rate, and/or tissue forming potential. Accordingly, in some embodiments, the method comprises: (i) determining the level of GSTT1 expression by a stem cell or plurality of stem cells, and; (ii) comparing the level of GSTT1 expression determined in step (i) to a reference value for the level of GSTT1 expression for that stem cell type. In some embodiments, the method further comprises the step of identifying a stem cell or plurality of stem cells having decreased GSTT1 expression relative to the reference value. In some embodiments the method further comprises the step of separating and/or isolating a stem cell or plurality of stem cells having decreased GSTT1 expression relative to the reference value from other cells or stem cells.

The present inventors have also discovered that certain genotypes of GSTT1 are correlated with cell proliferation (i.e. growth rate) and/or tissue forming potential. Accordingly, in a second aspect, the present invention provides a method for identifying a stem cell or plurality of stem cells, the method comprising determining the GSTT1 genotype of the stem cell or plurality of stem cells. In some embodiments, the method further comprises the step of identifying a stem cell or plurality of stem cells having a non-homozygous wildtype GSTT1 genotype. In some embodiments, the method further comprises the step of separating and/or isolating a stem cell or plurality of stem cells having a non-homozygous wildtype GSTT1 genotype from other cells or stem cells.

The stem cells having comparatively reduced or lower GSTT1 expression, and/or having GSTT1 genotypes correlated with enhanced or improved cell proliferation (i.e. growth rate) and/or tissue forming potential have various other characteristics which may help to distinguish them from stem cells having comparatively higher GSTT1 expression, and/or having a GSTT1 genotype not correlated with enhanced or improved cell proliferation (i.e. growth rate) and/or tissue forming potential. Accordingly, in some embodiments of the methods of the invention, the stem cells possess one or more of the following characteristics as compared to a reference population of stem cells: (i) enhanced colony forming capacity; (ii) reduced cell size; (iii) increased telomere length and/or reduced rate of telomere shortening; (iv) increased expression of STRO-1, SSEA-4, CD146 and/or PDGFRβ; (v) increased secretion of FGF-2, VEGF, SDF-1α, fractalkine, PDGF-BB and/or MIP-1α; (vi) enhanced suppression of T cells; (vii) decreased expression of ALP, RUNX2 and/or BSP-II; (viii) increased expression of TWIST-1 and/or DERMO-1.

The present inventors have discovered that the growth rate and/or tissue forming potential of stem cells can be modified by changing the level of GSTT1 gene or protein expression, or GSTT1 function.

In a third aspect, the present invention provides a method for modifying a stem cell or plurality of stem cells, the method comprising contacting a stem cell or plurality of stem cells with an agent capable of modifying a stem cell to reduce GSTT1 expression and/or function. In some embodiments the method comprises: (i) optionally isolating a stem cell or plurality of stem cells from an individual, and; (ii) contacting an isolated stem cell or plurality of stem cells in vitro with an agent capable of modifying a stem cell to reduce GSTT1 expression and/or function.

The present invention also provides a stem cell or plurality of stem cells which have been modified to reduce endogenous GSTT1 expression and/or function.

Also provided is a stem cell or plurality of stem cells, which contain an agent capable of reducing GSTT1 expression and/or function.

Also provided is a stem cell or plurality of stem cells, which have been modified to have decreased GSTT1 expression and/or function relative to stem cells which are homozygous for wildtype GSTT1 and/or stem cells having the average (i.e. mean) level of GSTT1 expression and/or function for that stem cell type.

Furthermore, the present invention provides an isolated stem cell or plurality of stem cells, which have decreased GSTT1 expression and/or function relative to stem cells which are homozygous for wildtype GSTT1.

In a further aspect of the present invention, a stem cell or plurality of stem cells according to the invention are provided for use in a method of medical treatment.

In another aspect of the present invention, the use of a stem cell or plurality of stem cells according to the invention in the manufacture of a medicament for use in a method of medical treatment is provided.

In one aspect, the present invention provides a method of regenerating tissue in a patient in need of such treatment, the method comprising administering to the patient a therapeutic number of stem cells according to the invention.

The present invention also provides the stem cell or plurality of stem cells according to the invention for use in a method of treating a bone fracture, or in the repair of cartilage tissue, wherein the method comprises administering the stem cells to tissue surrounding the fracture or to the site of the injury.

Also provided is the use of a stem cell or plurality of stem cells according to the invention for the generation of bone or cartilage tissue in vitro or in vivo.

In a further aspect, the present invention provides a method for selecting a stem cell donor, the method comprising determining the genotype for GSTT1 in a nucleic acid containing sample isolated from an individual, or determining GSTT1 expression in a sample isolated from an individual.

In some embodiments, the method comprises detecting the presence of a GSTT1 allele in the nucleic acid containing sample. In some embodiments, the GSTT1 allele is one or more of the wildtype GSTT1 allele, a GSTT1 genotype which is known and/or which would be predicted to result in decreased expression of GSTT1 relative to wildtype GSTT1, and the GSTT1 null (i.e. deletion) allele.

In a further aspect, the present invention provides a method for selecting a stem cell donor, the method comprising determining the genotype for GSTT1 in a DNA-containing sample isolated from an individual, wherein an individual determined to have a GSTT1 genotype which is known and/or which would be predicted to result in decreased expression of GSTT1 relative to individuals homozygous for wildtype GSTT1 is selected as a stem cell donor.

In another aspect, the present invention provides a method for selecting a stem cell donor, the method comprising: (i) determining the level of GSTT1 expression by a stem cell or plurality of stem cells in a sample isolated from an individual, and; (ii) comparing the level of GSTT1 expression determined in step (i) to a reference value for the level of GSTT1 expression for that stem cell type; wherein an individual determined to have a stem cell or plurality of stem cells having decreased GSTT1 expression relative to the reference value is selected as a stem cell donor.

In accordance with methods for selecting stem cell donors, in some embodiments the stem cell or plurality of stem cells additionally possess one or more of the following characteristics as compared to a reference population of stem cells: (i) enhanced colony forming capacity; (ii) reduced cell size; (iii) increased telomere length and/or reduced rate of telomere shortening; (iv) increased expression of STRO-1, SSEA-4, CD146 and/or PDGFRβ; (v) increased secretion of FGF-2, VEGF, SDF-1α, fractalkine, PDGF-BB and/or MIP-1α; (vi) enhanced suppression of T cells; (vii) decreased expression of ALP, RUNX2 and/or BSP-II; (viii) increased expression of TWIST-1 and/or DERMO-1.

In another aspect of the present invention a method of enriching for colony forming units (CFU-F) in a culture of stem cells, preferably mesenchymal stem cells (MSC), is provided the method comprising partitioning stem cells having a decreased level of GSTT1 expression.

In another aspect of the present invention a method of enriching for colony forming units (CFU-F) in a culture of stem cells, preferably mesenchymal stem cells (MSC), is provided the method comprising partitioning stem cells not having a homozygous wildtype GSTT1 genotype.

Partitioning of cells may involve separating and/or isolating cells having, or not having, a selected characteristic from cells that do not have, or have, the characteristic respectively. As such, a population of cells enriched for cells having a desired characteristic may be provided. The characteristic may be a decreased level of GSTT1 expression or none homozygous wildtype GSTT1 genotype.

In another aspect of the present invention a kit for determining GSTT1 expression is provided, the kit comprising reagents for determining the level of expression of GSTT1 by a stem cell or plurality of stem cells in a sample.

In another aspect of the present invention a kit for determining GSTT1 genotype is provided, the kit comprising reagents for determining the GSTT1 genotype in a DNA containing sample.

Kits in accordance with aspects of the invention are useful in methods for selecting a stem cell donor in accordance with the invention. In particular, the kits are useful for the identifying suitable donors of bone marrow for obtaining stem cells.

DESCRIPTION

GSTT1

Glutathione-S-transferase theta 1 (GSTT1) is a metabolic enzyme that belongs to the GST superfamily. This family of phase II metabolic proteins is classified into 7 classes according to their sequence and structure. They catalyze the conjugation of reduced glutathione to electrophilic and hydrophobic xenobiotics for detoxification (FIG. 1A). They also remove reactive oxygen species, biosynthesize and metabolize prostaglandins and steroids.

The DNA, coding DNA (i.e. CDS), and amino acid sequences for wildtype Homo sapiens GSTT1 are provided below:

```
Homo sapiens GSTT1 DNA sequence (NCBI Ref. Seq. NT_187633.1
GI: 568815467)
ACTGGAGTTTGCTGACTCCCTCTGGTTTCCGGTCAGGTCGGTCGGTCCCCACTATGGGCCTGGAGC

TGTACCTGGACCTGCTGTCCCAGCCCTGCCGCGCTGTTTACATCTTTGCCAAGAAGAACGACATTC

CCTTCGAGCTGCGCATCGTGGATCTGATTAAAGGTAGGTCCAGCCTCGGGTTTGGGGAACCGAAAA

GTCAGGAAGGGGACAGGTAGGCATACATAGCTTAGGGAACTTCTCCCAGCGCCACCTTCTTCCTGG

GGCCATTGCTGGTCTGGTTTGGAGACCGAACAGAGAAAGGTGAGCCAGCAGGGAGATCCAAGAGTC

GGGGCTCCCCAAAACTCTGCTCGGTCTCACGGAATAGACCACGGGGTTCCCCTGAGGCCGAATAAA

GGGGTGGGGATCATGAAGAGAAGCCAGACAGGAGGACAAAAACGGGCGCAGCTGGGTGCAGGGGCA

CACGCCTGTAGTCCCAGCAACTCGAGAGGCTGGGGTGGGAGGATCGCTTGAGCCCAGGAATTCCAG

GCCGCAGTGCACTATCATGGTGCCCTTGAATAGCCACTGCACTCCCGTCAGGGCAATCTAGCGAGA

CCCCGTCTTAAAAAAAAAAAACAAAAAAAAACAAAATGAAAGCAGGTGTGACCTCGGCCTAGGGAA

AGGTGGGATGAGAGAGGTCAAGGGTGCCAAGTGTAGAGACTGGGACAGCGTCAAGTCCCTTCTTTA

TGGCCCAGCTGCTGAGATTCTGCAACAGCAAACAGCTCAGGACGTGACTTTCCATCCCTGCCCTCT

GCACTCGTCCAGTCTGCATTGGGGTCCCTCTTTGTCCCTTCCTTCCTCTGTTCCTCCTGTTTTGCC

TCTGACCTTGTCCTTGTCCTTTTTTTTTGAGACAGAGTCTTGCTTTTGCTTTGTTGCAGTGCAGT

GGCACGGATCTCGAATCACTGCAACCACCACCTCCCGGGTTCAAGCAATTCTCCTGCTTCAGCCTC

CTGAGTAGCTAGATTACAAATGTGTGCCACTATGTCTGGCTAATTTTTTTGTATTTTTAACAGAGA

TGGGATTTCACAATTTTGGTCAGGCTGTTCTCGAACTCCTGACATCAAATGATCTGCCGGCTTAGC
```

-continued

```
CTCCCAAAGTGCTGGGATTACAGGCATGAGCCACTGTGCCTGGCCCAAGGCATTTTGTTTATTTGT
TTGTTTGTTTTTGAGACGGAGTCTCGCTCTGTCGCCCAGGCTGGAGTGCAGTGGCAGGATCACAGC
TCACTGCAACCTCTGCCGCCCGAAACCTTGTCCTCTGCCTCTTGTTCCTGCTGGGGAGGTAGGTTG
CCCCAGGCTGCTGATGCTGGAAGCAGCAGGGGGACCCTGGGGCTTGATGAGCCCTACACCCTGTTT
TGTTTCTCTAGCATGCCTCCAAGGCCCTTGAGGACTCAGCTGGCAGGCCCAGGCCCAGGCCCAGTG
CAGGGTGGGGTAGTAGGAGGGGTTGGAAGCAGAATCCAGGTATGGCTGGTGGGGCAAGTAAGGCGA
CTCTACTTGGCTAAGCCTTCTGCCCAGGGCTCCCACTCCATGGCTGGCCCTCTGCCTGAAACTTCT
CCACATAATCTCTTCTGCAAACTGCCCACTGTCCTGCGCAAGGACTTCCTCTGCAGAGTGTGGAGT
AGAGGAAAGGGAATGGGGGACAAGAGGACGTCCAAGCTGGTTGTCAAATGTAGTGGTGCAGAGGGA
AGTGTGTTTTCCCAGGAGACAGAGGAGGGTTTTCCTGGTGAAGGAACAGTCTGAAGGGAGGGTGAA
GAGAGGGTAGCAGGCTGGGCATGGTGGCTCACACCTGTAATCCCAGCACTTTGGGAGGCCGAAGTA
GGAAGATTACTTGAGGCCAGTAGTTCAAGACCAGCCTGGGCAACATAGTGAGACCCCAACTGTAAG
GGGAATAAAAGTTTGGGGCACAGGGGGTGGTAGCAGGTATGCTACACACAGCTCCACAGTGCCCAG
GGCAGGGTGAACAAAGGGACATGGTGGGGCCAGTAGAAGTTGCTTCTAAGTAGGTAGATACCAGAA
AAAGACCACTTCTCTGTGTTTCATGACCCTGCCTTAGAATTAATGGTGGAAGGGACAAGGTAGTCA
GTCCCCTCAGGTGACCTATCGTGCAGCTTGGGGTGCTCTGATTGTGAGTTCATGAAGCTGGCAATA
GTGGAAAGAGGAGATGGGTAGGGTGCATGCAAAGGTCCAGGAACCACACCCTGCACAGTGAGCTCT
GTTGCAGAGGGGCAGCCTGTGGGAGGAGGCTGTGCCTACAGGACTTAGCAAGGGGTGTTGTCTATT
TTGTACCAGCCGGTGGAGTGGTCTCCTCCTCCTCCCGCAGGGGCCCTTCCAGTCTTTGCCAACCAG
GAGTGCAGACTGGTGGGAAGAAGAACTGTGAAACTGGGGCCAGAGCATTGCAGGGAGGGGCACAGG
CCATGGCGGGCTCAGCGTTCTCCTCCCACCACCCACCATGCTGGACTCTTCCCAGGTCAGCACTTA
AGCGATGCCTTTGCCCAGGTGAACCCCCTCAAGAAGGTGCCAGCCTTGAAGGACGGGGACTTCACC
TTGACGGAGAGGTAACTGGGACCCTAGGACTGCTGCCAGGCCTGCTGGAACCATCCTGTTCTAACC
CTCTATTTCATAGACAAGGAAACTAAAGTCTTCAGAGGCAGAGAGTCTCTGTGCCCCGCATCCTGC
AGAGAGTCAGTACTGGACCCCAGGCCCTTGCCTTCCTGCTATTCCAGTTCACCCTGATGATTAGAA
AAGCAAATATCTACTTTACTTCCACACCAGTGCTTTGGTTGCTGGTGAGTGGTGAGAGTATCCTTG
AGACAGGGTAGGCCAGAGGACGATGGCAGCTTTGCCCACCGTGGGGCAGGCCTCTGGCCAAGCTTG
TGTGGCGATGGCTCAGTGGCATCTGGGCTGCCCGGTGGCTCCATCTCTGGGCTGCAGCTTCCCAGG
ATGGGTCTTCCCCATGGAAGAGCCACCAGATATGGACGTCTTACATCACAGCTGGTCCCAAGAAGT
TGAATCCTCTTCAGGAAAAGCCAATCTTTCCCCAGTTCTGCCCCTTTTGTCACCAGAGTCACCCTT
CCCCTAACAAGAACCTGGAGTTTGTGCTTTAAAGCTCATCTCTGAAATCTCAGGATGGACGCACCT
CCGATGAATTCCTCTGACATTCTGCCAGGGCCCGTCTTCCTCCCTGGTGCCCCAGGTGTCCTGAGT
CCTTGTGTCACTCAGCGTTGTGACCCCCAGGTACCAGCCAGAGTCAATGTGCAATCTCTGCCTCTG
TCACTACTCTCACCTTCAGGTCTGTGGCTCACAGAGACCTGCAGCCCTCCTCAGAGGTGGCTTGAA
CAATTGGCTGGGAGCAAAAGGAGCTCCTGGGCACCCTGCACAGACAACGGAGTCGTTAAGCTGGGA
CACGTGTGTAGCCCCAGCTTAAAAGAGAATATAGGCCCGTGGCAGATACAGAGGTTTTCTGCCCTT
TTGGCCTGCATGCCCAACCTTTGGGAAACCCCAAGTTCCTGAAAGCTTTTCTGTGTCTCCAAATGG
ACACATCCTGTGTCCTTCCAGGTCCATGCTCATCTCATCACCATGGCGGCCCTCAAAACCCAGGGA
AGGAGGAGAGTGCCAGGGGGCCTTGTCTGTTCTGTTGTTCTAGGATCCTGCAGCTGCAGGAGTGCT
TCCTGAGTGGTACTTTAGGAAGCCAAACTACCCCAGTCAGCTTAGATAGGAGCTGATTCTTGGCAG
```

-continued

```
AAAGAATGACAGAAAGAACAAAGGGACACGGAAGCCTTTTTGAACAGTCAGGCCATCAGAGGCTGG

TCGGAATCCCAGCAGATGAGAGTGGATACCGAATGGAAAGAACTGAGCTTCTTTAAAGCTCAGCTT

TGATGCCCCGTTCTCCTGGAAGCTCTCTCTGGTTCTCTGATCAGAAACTGTCTCTAAACATTTGGC

AAGACATTCTGTTGTGGGATTTTGCCTGGTGGTAGGAAAAGCTTGGGTATTAGCCTCAGAAAGATT

CTCAGCTCTGCCATTAAGAGCTGTGTGCCCTAGGGCAAGTCTCTGCCTTTCTAAGCCTGGTTTTCT

TCTCTGGAAAATGAGGCTAATACTTTGGCAAATTGTCAGAAAGGTTAAAGAAGTGTGCTGGGCACA

GTGGTTCATGCCTATAATGCCAGCGCTTTGGGATGCCAAGGCTGGAGGATTGCTTGAGGATAGGAG

TTTAAGACCAGCCTGGCAATACAGTGAGATCCCATCTCTACAAAAAAGAAAAAAGGTAGCCAGGCA

TGGTGGTGCACTCCTATAAAAATTGAAGCTGCAGTGAGCTGAGACTGCACCACTGCACTCCAGCCT

GGGTGACTGAGGAAGACCTTGTCTCCAAAAAAAAAAAAAAAAAAAAAAAAAAAAAAGGCCAGGTGC

GGTTGCTTATACGTGTAATCACAGCACTTTGGGAGGCCGAGGCAGGCAGATCACAAGGTCAGGAGT

TCGAGACCATCCTGGCTAATATGGTGAAACCCCATCTCTACTAAAACTACAAAAAATTAGCCAGGC

ATGGTGGCACGCACCTGTAGTTCCAGCTACTTGGGAGGCTGAGGCAGGAGAATCACTTGAACCCGG

GAGGTGGAGGTTGCAGTGAGCCAAGATCGCACCACTGCACTCCAGCCTGAGCGACAGAGCGAGACT

CCGTATCAAAAAAAAAAAAAAAGCGACTATGTATGAAATACCCAGCACAGTGCCCTTCCCTTACCCA

TCATGACCCCCACACCCACAGTGTGGCCATCCTGCTCTACCTGACGCGCAAATATAAGGTCCCTGA

CTACTGGTACCCTCAGGACCTGCAGGCCCGTGCCCGTGTGGATGAGTACCTGGCATGGCAGCACAC

GACTCTGCGGAGAAGCTGCCTCCGGGCCTTGTGGCATAAGGTGAGGCTGGGAATGTGGGGGCGGC

AGCGAGAGCATTCCCCAAAGGTGTTCAGGCACCAGTCTCTTCTTTTCAGTTTTGGATTATTTCTAC

TGACCTGTCTTTGCCTTCACAGATTCTTTCCTCTGTTGTGCCAAATTGCTATTAAGCCCATCCAAT

ACATTCTTTGTTTGAGATATGTATTTTTCAGCTCTGGAAATTCCATTTGGTTGTTTTTTAGAATTT

CCACTTCTCTGATGAAATTCACCATCTGTTCATCCATTTTATCTGTCTTTTCTTGTAAATTCTTTA

ACATATTTATCACTGTTACCTAAAAATCTTTGTCAACTAATTTCAACACGTAGGTGTTCTGTGGGT

CTGGTTTTTTGTTTTGTTTTGTTTTGAGATGGGGTCTCACTCTGTCACCCAGGCTGAGTGCAAT

GGTGCGATCTCAGCTCACTGCAACCTCCACCTCCCAGGCTCAAGCGATTCTCCTGCCTCAGCCTCC

TGCGTAGCTGGGATTACAGGCACCCACCAGCACACCTGGCTAACTTTTGTTATTTGTAGTGGAGAC

CGGGTTTCACCATGTTGGCCAGGCTGGTTTCGAACTCTCCACCTGAAGTGATTCGTCCTCCTTGGC

TTCCCAAAGTGTTGGGATTACAGGCATGAGCCACCATACCCAGCCTACGGGTCTATTTCTATTGAT

TGTTGTTTTCTCCCTCTTGATTATGGGTCACATTTGCCTGCTTCTTTGCATGTCTCATGATGTATT

ATCATTATTTTTATTTTTTGAGACGGACTCTCACTCCATTGCCCAGGCTGGCGTGCAATGGCAC

GATCTTGGCTCACTGCAACCTCCGCCTCCTGGGTTCAAGCGATTCTCCCACCTCAGCCTCCCAAGT

AGCTAGAATTACAGGCACCTGCCATCATGCCTGGCTAATTTTTGTATTTTTGTAGAGACAGGGTTT

CACCATGTTGGCCAGGCTGGTCTTGAACTCCTGACCTCAGGTGATCCTCCCATCTCGGCCTCCCAA

AGTGCTGGGATTGTAGGCATGAGCCACCATGCCCGGCCTCATGATGTATCCTTGTGTGCCAGACAT

TATGATAAAAGAAGAGCAGAGATTGAATTGCATAATAAACACCCCCAAGAAAGGGCTTGCACTTCC

CTGTGTCAGGTAGCCAGGATGTGAGGCTGTTCTCTTCTAAGCTAATCAGGAGGTGGGCTGGGTTGC

AGGTTTAGTTGGTTTCAGTTTATCTTTGGTTTCAAATATCTTGAATGTGAGATCAGGTCACTAGCT

CAGTCTAGCATGGCTTTGGAATCTAATCACCAACTACGATGTTGCCTGTAAGATCTCTCTGCTTTT

CATCCCTGCCCCCAGTTCCCAAACTGCTGCTCAGTCAGAAAAGCCCATGCCTGTGACAGTCTTTCT

CCCAGCCTGCTTGGGCCCAAGGAAATGAAATTGGAATGAAAGTAGCTCATCTAGGAACGGCTTATG

CCTCTCTGGAATTTAGTTCATTTAGTCAAGTGCTGTCCGATAGAAGTATAAAGTGAGCCACATACG
```

-continued

```
TAATTTTAAATTTTCTAGTAGGCACATTTAAAAAGTAAAAAGAGTCCAGGCACAGTGGCTCATGCC
AATAATCCTAGCACTTTGGGAGGCCAAGGCAGTGGATCACCTGAGGTCAGGAGTTCGAGACCAGCC
TGGTCAACATGGGGAAACCTTGTCTCTACTAAAACCACAAAAATTAGCCAGGCTTGGTGGCCTGTG
CCTATAATCCCAGCTACTCAGGATGCTGAGGCAGGAGAATTGCTTGAACCCAGGGGGCAAAGTTGG
CAGTGTGCCGAGATGGTGCCACTTCACTCCAGCCTGGGTGACAGAGCTGAACACTGTCTCAAAAGA
AAAAAAAAAGTAAAAGGAAATTGATATATTTTACTTAACCCAATGTGTTGAGAATATTATCATTT
TGGCCAACAAGTACAAGAAAAGATGCTTGGCCGGGCGCGGTGGCTCACGCCTGTAATCCCAGCACT
TTGGGAGGCGGAGGCAGGCAGATCACAAGGTCAGGAGATTGAGACCATCCTGGCTAACACAGTGAA
ACCCTGTCTCTACTAAAAATAAAAAAAAAATTAGCTGGGCGTGGTGGCGGGCACCTGTAGTCCCAG
CTACTCGGGAGGCTGAGGCAGGAGAATGGCGTGAACCCAGGAGGCGGAGCTTGCAGTGAGCCGAGA
TCACCCCACTGCACTCCAGCCTGGGCGAGAGAGCAAGACTCAGTCTCAAAAAAAAAAAAAAAAGAA
AAGATGCTCAGCATCACTAATCATTAGGGAAATGCAAATCAAAACTAACTCCCTACTCCAGTAACT
CCCGACTTTGCCTGCCCAATCCCCAGGTGATGTTCCCTGTTTTCCTGGGTGAGCCAGTATCTCCCC
AGACACTGGCAGCCACCCTGGCAGAGTTGGATGTGACCCTGCAGTTGCTCGAGGACAAGTTCCTCC
AGAACAAGGCCTTCCTTACTGGTCCTCACATCTCCTTAGCTGACCTCGTAGCCATCACGGAGCTGA
TGCATGTGAGTGCTGTGGGCAGGTGAACCCACTAGGCAGGGGCCCTGGCTAGTTGCTGAAGTCCT
GCTTATGCTGCCACACCGGGCTATGGCACTGTGCTTAAGTGTGTGTGCAAACACCTCCTGGAGATC
TGTGGTCCCCAAATCAGATGCTGCCCATCCCTGCCCTCACAACCATCCATCCCCAGTCTGTACCCT
TTTCCCCACAGCCCGTGGGTGCTGGCTGCCAAGTCTTCGAAGGCCGACCCAAGCTGGCCACATGGC
GGCAGCGCGTGGAGGCAGCAGTGGGGGAGGACCTCTTCCAGGAGGCCCATGAGGTCATTCTGAAGG
CCAAGGACTTCCCACCTGCAGACCCCACCATAAAGCAGAAGCTGATGCCCTGGGTGCTGGCCATGA
TCCGGTGAGCTGGGAAACCTCACCCTTGCACCGTCCTCAGCAGTCCACAAAGCATTTTCATTTCTA
ATGGCCCATGGGAGCCAGGCCCAGAAAGCAGGAATGGCTTGCCTAAGACTTGCCCAAGTCCCAGAG
CACCTCACCTCCCGAAGCCACCATCCCCACCCTGTCTTCCACAGCCGCCTGAAAGCCACAATGAGA
ATGATGCACACTGAGGCCTTGTGTCCTTTAATCACTGCATTTCATTTTGATTTTGGATAATAAACC
TGGGCTCAGCCTGAGCCTCTGCTTCTAA
```

Homo sapiens GSTT1 coding sequence (NCBI Ref. Seq. NM_000853.2 GI: 167466163)

```
ACTGGAGTTTGCTGACTCCCTCTGGTTTCCGGTCAGGTCGGTCGGTCCCCACTATGGGCCTGGAGC
TGTACCTGGACCTGCTGTCCCAGCCCTGCCGCGCTGTTTACATCTTTGCCAAGAAGAACGACATTC
CCTTCGAGCTGCGCATCGTGGATCTGATTAAAGGTCAGCACTTAAGCGATGCCTTTGCCCAGGTGA
ACCCCCTCAAGAAGGTGCCAGCCTTGAAGGACGGGGACTTCACCTTGACGGAGAGTGTGGCCATCC
TGCTCTACCTGACGCGCAAATATAAGGTCCCTGACTACTGGTACCCTCAGGACCTGCAGGCCCGTG
CCCGTGTGGATGAGTACCTGGCATGGCAGCACACGACTCTGCGGAGAAGCTGCCTCCGGGCCTTGT
GGCATAAGGTGATGTTCCCTGTTTTCCTGGGTGAGCCAGTATCTCCCCAGACACTGGCAGCCACCC
TGGCAGAGTTGGATGTGACCCTGCAGTTGCTCGAGGACAAGTTCCTCCAGAACAAGGCCTTCCTTA
CTGGTCCTCACATCTCCTTAGCTGACCTCGTAGCCATCACGGAGCTGATGCATCCCGTGGGTGCTG
GCTGCCAAGTCTTCGAAGGCCGACCCAAGCTGGCCACATGGCGGCAGCGCGTGGAGGCAGCAGTGG
GGAGGACCTCTTCCAGGAGGCCCATGAGGTCATTCTGAAGGCCAAGGACTTCCCACCTGCAGACC
CCACCATAAAGCAGAAGCTGATGCCCTGGGTGCTGGCCATGATCCGGTGAGCTGGGAAACCTCACC
CTTGCACCGTCCTCAGCAGTCCACAAAGCATTTTCATTTCTAATGGCCCATGGGAGCCAGGCCCAG
```

-continued

```
AAAGCAGGAATGGCTTGCCTAAGACTTGCCCAAGTCCCAGAGCACCTCACCTCCCGAAGCCACCAT

CCCCACCCTGTCTTCCACAGCCGCCTGAAAGCCACAATGAGAATGATGCACACTGAGGCCTTGTGT

CCTTTAATCACTGCATTTCATTTTGATTTTGGATAATAAACCTGGGCTCAGCCTGAGCCTCTGCTT

CTAAAAAAAAAAAAAAAAAA
```

Homo sapiens GSTT1 amino acid sequence (NCBI Ref. Seq. NP_000853.2
GI: 167466164)

```
MGLELYLDLLSQPCRAVYIFAKKNDIPFELRIVDLIKGQHLSDAFAQVNPLKKVPALKDGDFTLTE

SVAILLYLTRKYKVPDYWYPQDLQARARVDEYLAWQHTTLRRSCLRALWHKVMFPVFLGEPVSPQT

LAATLAELDVTLQLLEDKFLQNKAFLTGPHISLADLVAITELMHPVGAGCQVFEGRPKLATWRQRV

EAAVGEDLFQEAHEVILKAKDFPPADPTIKQKLMPWVLAMIR
```

In this specification "GSTT1" includes proteins or polypeptides having at least 70%, more preferably one of 75%, 80%, 85%, 90%, 95%, 96%, 97%, 98%, 99% or 100% sequence identity with the amino acid sequence of GSTT1, such proteins or polypeptides preferably retaining glutathione reduction function.

A GSTT1 protein or polypeptide may be a fragment or truncate of a full length GSTT1 protein or polypeptide or mature form lacking a signal sequence.

The GSTT1 protein may be from, or derived from, any animal or human, e.g. non-human animals, e.g. rabbit, guinea pig, rat, mouse or other rodent (including from any animal in the order Rodentia), cat, dog, pig, sheep, goat, cattle (including cows, e.g. dairy cows, or any animal in the order Bos), horse (including any animal in the order Equidae), donkey, and non-human primate or other non-human vertebrate organism; and/or non-human mammalian animal; and/or human.

GSTT1 genotypes can be determined by a variety of means well known to those skilled in the art. These include but are not limited to restriction fragment length polymorphism identification (RFLPI) of genomic DNA, random amplified polymorphic detection (RAPD) of genomic DNA, amplified fragment length polymorphism detection (AFLPD), polymerase chain reaction (PCR), DNA sequencing, allele specific oligonucleotide (ASO) probes, and hybridization to DNA microarrays or beads.

Similarly, the skilled person is well able to employ methods for identifying other variation such as epigenetic marks. These include but are not limited to chromatin immunoprecipitation (ChIP) based methods, fluorescent in situ hybridization (FISH), using methylation-sensitive restriction enzymes, DNA adenine methyltransferase identification (DamID) and bisulfite sequencing.

GSTT1 Expression and Function

Genetic polymorphisms within GST genes are common in the world population with the members having either point mutations or a complete loss of gene. Homozygous deletion of GSTT1 is prevalent in approximately 20-60% of most populations (FIG. 2). This is caused by the homologous recombination of highly similar stretches of sequences flanking the gene.

The present invention is concerned with any variation (including genetic variation, epigenetic variation, DNA methylation, etc.) which influences the level of GSTT1 gene and/or protein expression, and/or the level of functional GSTT1 protein and/or GSTT1 activity. For example, the variation may influence transcription, mRNA processing (e.g. splicing), mRNA stability, translation, post-translational processing, protein stability, protein degradation and/or protein function/activity.

In aspects of the present invention, methods are provided for identifying a stem cell or plurality of stem cells, and/or identifying stem cell donors based on GSTT1 genotype.

In particular, the present invention is concerned with GSTT1 genotypes which gives rise to a level of gene and/or protein expression and/or a level of functional GSTT1 protein and/or a readout for GSTT1 protein function, which is less than or reduced relative to the level of gene and/or protein expression and/or the level of functional GSTT1 protein and/or the readout for GSTT1 protein function for a reference stem cell.

A 'reference stem cell' as used herein can be a stem cell which is homozygous for wildtype GSTT1, preferably a stem cell of the corresponding type. Alternatively, a 'reference stem cell' can be a representative stem cell of the corresponding type. In some embodiments, a 'reference stem cell' may be a notional stem cell having the average (i.e. mean) value/level/status for that stem cell type.

In some embodiments, the level of gene and/or protein expression and/or a level of functional GSTT1 protein and/or a readout for GSTT1 protein function gene and or protein expression may be less than 1 times, less than 0.99 times, less than 0.95 times, less than 0.9 times, less than 0.85 times, less than 0.8 times, less than 0.75 times, less than 0.7 times, less than 0.65 times, less than 0.5 times, less than 0.45 times, less than 0.4 times, less than 0.35 times, less than 0.3 times, less than 0.25 times, less than 0.2 times, less than 0.15 times, less than 0.1 times, less than 0.05 times, or less than 0.025 times the level expression compared to the level of expression of a reference stem cell.

The genotype may be a point mutation, substitution, insertion, or deletion, and may reduce or influence transcription, mRNA processing (e.g. splicing), mRNA stability, translation, post-translational processing, protein stability, protein degradation and/or protein function/activity. For example, the variation may be a homozygous deletion of the GSTT1 gene. Example genotypes of interest include GSTT1 homozygous negative (i.e. GSTT1−/GSTT1−) and heterozygous (GSTT1+/GSTT1−) genotypes.

Variation predicted to influence the level of GSTT1 gene and/or protein expression, and/or the level of functional GSTT1 protein and/or GSTT1 activity can be identified using informatics-based techniques. For example, the predicted effect of a genetic variant identified in the GSTT1 coding sequence can be determined by 'translating' the altered coding sequence into a predicted amino acid sequence in silico. In this way, variants predicted to result in e.g. a premature stop codon and thus a truncated, potentially non-functional GSTT1 can be identified.

Measuring GSTT1 Expression and Function

The present inventors have unexpectedly found that GSTT1 expression is inversely correlated with cell proliferation (i.e. growth rate or cell doubling time) and/or tissue forming potential. 'GSTT1 expression' as used herein may be gene expression, protein expression and/or GSTT1 protein activity.

GSTT1 gene expression can be measured by a various means well known to those skilled in the art. For example, gene expression can be measured by measuring levels of GSTT1 mRNA, for example by quantitative real-time PCR (qRT-PCR), or by reporter-based methods.

Similarly, GSTT1 protein expression can be measured by various methods well known in the art. For example, GSTT1 protein expression and be measured by antibody-based methods, for example by western blot, immunohistochemistry, immunocytochemistry, flow cytometry, ELISA, etc. Expression can also be measured by reporter-based methods.

GSTT1 activity (i.e. GSTT1 protein function) can be measured by various means, for example by assaying glutathione-S-transferase activity.

A stem cell or plurality of stem cells having reduced GSTT1 gene expression and/or GSTT1 protein expression and/or GSTT1 activity are identified as having improved/enhanced cell proliferation (i.e. growth rate) and/or tissue forming potential.

In accordance with certain methods of the present invention, readouts for GSTT1 expression are compared between e.g. cells, samples and/or individuals, or compared to reference values for GSTT1 expression.

For example, the level of GSTT1 expression by a stem cell or plurality of stem cells may be compared to a reference value for the level of GSTT1 expression for that stem cell type.

A reference value may be a known and/or published value for the level of GSTT1 expression for that stem cell type, or may be an average (i.e. a mean) value of GSTT1 expression for that stem cell type. In some embodiments, the reference value may be or may have been determined empirically.

In some embodiments, the reference value may be the value for the level of GSTT1 expression by a corresponding cell having the homozygous wildtype genotype for GSTT1 (GSTT1+/GSTT1+).

GSTT1 gene expression and/or GSTT1 protein expression and/or GSTT1 activity can be compared between cells—e.g. between a stem cell having a homozygous wildtype genotype for GSTT1 and a stem cell not having a homozygous wildtype genotype for GSTT1.

In some embodiments, the stem cells having reduced GSTT1 gene expression and/or GSTT1 protein expression and/or GSTT1 activity have a GSTT1 gene expression and/or GSTT1 protein expression and/or GSTT1 activity which is less than 100%, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% of the reference level of GSTT1 gene expression and/or GSTT1 protein expression and/or GSTT1 activity.

In some embodiments, the level of GSTT1 gene expression and/or GSTT1 protein expression and/or GSTT1 activity correlates with the number of copies of the wildtype GSTT1 gene. For example, from highest to lowest GSTT1 gene expression and/or GSTT1 protein expression and/or GSTT1 activity, genotypes are GSTT1+/GSTT+>GSTT1+/GSTT−>GSTT1−/GSTT−.

For each of the properties described hereinbelow correlated with the level of GSTT1 gene expression and/or GSTT1 protein expression and/or GSTT1 activity, the properties are correlated with the number of copies of the wildtype GSTT1 gene.

Stem Cells

The stem cells cultured and described herein may be stem cells of any kind. They may be totipotent, pluripotent or multipotent. They may be embryonic or adult stem cells from any tissue and may be hematopoietic stem cells, neural stem cells or mesenchymal stem cells. Preferably they are adult stem cells.

In this specification, by stem cell is meant any cell type that has the ability to divide (i.e. self-renew) and remain totipotent, pluripotent or multipotent and give rise to specialized cells.

Stem cells cultured in the present invention may be obtained or derived from existing cultures or directly from any adult, embryonic or fetal tissue, including blood, bone marrow, skin, epithelia or umbilical cord (a tissue that is normally discarded).

The multipotency of stem cells may be determined by use of suitable assays. Such assays may comprise detecting one or more markers of pluripotency, e.g. alkaline phosphatase activity, detection of RUNX2, osterix, collagen I, II, IV, VII, X, osteopontin, osteocalcin, BSPII, aggrecan, ALBP, CCAAT/enhancer binding protein-α (C/EBPα), adipocyte lipid-binding protein (ALBP), alkaline phosphatase (ALP), bone sialoprotein 2, (BSPII), Collagen2a1 (COL2A1) and SOX9.

In some preferred embodiments the stem cells are mesenchymal stem cells (MSCs), e.g. capable of differentiation into connective tissue and/or bone cells such as chondrocytes, osteoblasts, myocytes and adipocytes. In some preferred embodiments the MSCs are BM-MSC.

Mesenchymal stem cells are easily obtainable from bone marrow by minimally invasive techniques and can be expanded in culture and permitted to differentiate into the desired lineage. Differentiation can be induced by the application of specific growth factors. The transforming growth factor beta (TGF-beta) superfamily member proteins such as the bone morphogenetic proteins (BMPs) are important factors of chondrogenic and osteogenic differentiation of mesenchymal stem cells.

Mesenchymal stem cells can be isolated and detected using selective markers, such as STRO-1, from a CD34+ fraction indicating their potential for marrow repopulation. These cell surface markers are only found on the cell surface of mesenchymal stem cells and are an indication of the cell's multipotency.

Suitable mesenchymal stem cells may be obtained or derived from bone marrow mononuclear cells (BMMNCs) collected from aspirates of bone marrow (e.g. Wexler et al. Adult bone marrow is a rich source of human mesenchymal 'stem' cells but umbilical cord and mobilized adult blood are not. HAEMOPOIESIS AND LEUCOCYTES *British Journal of Haematology* 121(2):368-374, April 2003.) or Wharton's Jelly of the umbilical cord (e.g. Ta et al. Long-term Expansion and Pluripotent Marker Array Analysis of Wharton's Jelly-Derived Mesenchymal Stem Cells. *Stem Cells Dev.* 2009 Jul. 20 (Epub)).

Mesenchymal stem cells may be obtained by differentiation of pluripotent stem cells, such as human embryonic stem cells or induced pluripotent stem cells, by application of suitable differentiating factors, as is well known in the art.

Mesenchymal stem cells are multipotent progenitor cells with the ability to generate components of cartilage, bone, muscle, tendon, ligament, and fat. These primitive progenitors exist postnatally and exhibit stem cell characteristics, namely low incidence and extensive renewal potential. These properties in combination with their developmental plasticity have generated tremendous interest in their potential use to replace damaged tissues. In essence these stem cells could be cultured to expand their numbers then transplanted to the injured site or after seeding in/on scaffolds to generate appropriate tissue constructs.

Thus, an alternative approach for skeletal, muscular, tendon, ligament and blood repair/regeneration is the selection, expansion and modulation of the appropriate progenitor cells (e.g. mesenchymal stem cells, chondrocytes) in combination with a conductive or inductive scaffold to support and guide regeneration together with judicious selection of specific tissue growth factors.

The stem cells may be obtained from any animal or human, e.g. non-human animals, e.g. rabbit, guinea pig, rat, mouse or other rodent (including cells from any animal in the order Rodentia), cat, dog, pig, sheep, goat, cattle, horse, non-human primate or other non-human vertebrate organism; and/or non-human mammalian animals; and/or human. Preferably they are human. Optionally they are non-human. Optionally they are non-embryonic stem cells. Optionally they are not totipotent.

In yet a further aspect of the present invention, a pharmaceutical composition comprising stem cells or other cells generated by any of the methods of the present invention, or fragments or products thereof, is provided. The pharmaceutical composition may be useful in a method of medical treatment. Suitable pharmaceutical compositions may further comprise a pharmaceutically acceptable carrier, adjuvant or diluent.

In another aspect of the present invention, stem cells or other cells generated by any of the methods of the present invention may be used in a method of medical treatment, preferably, a method of medical treatment is provided comprising administering to an individual in need of treatment a therapeutically effective amount of said medicament or pharmaceutical composition.

Stem cells and other cells obtained through culture methods and techniques according to this invention may be used to differentiate into another cell type for use in a method of medical treatment. Thus, the differentiated cell type may be derived from, and may be considered as a product of, a stem cell obtained by the culture methods and techniques described which has subsequently been permitted to differentiate. Pharmaceutical compositions may be provided comprising such differentiated cells, optionally together with a pharmaceutically acceptable carrier, adjuvant or diluent. Such pharmaceutical composition may be useful in a method of medical treatment.

Mesenchymal Stem Cells

In some preferred embodiments the stem cells are mesenchymal stem cells (MSCs), e.g. capable of differentiation into connective tissue and/or bone cells such as chondrocytes, osteoblasts, myocytes and adipocytes.

Mesenchymal stem cells (MSCs) were originally isolated from the bone marrow and are present as only 1 in 104-105 total bone marrow mononuclear cells (BMMNC) (Friedenstein et al. 1966). These cells are capable of producing colonies derived from single cell precursors, dubbed the CFU-F (colony forming unit fibroblast) population. MSCs have now been identified in many other tissues including adipose tissue (Gimble and Guilak 2003; Zuk et al. 2001), umbilical cord blood (Bieback et al. 2004; Erices et al. 2000; Goodwin et al. 2001; Kogler et al. 2004; Wagner et al. 2005) and muscle (Jiang et al. 2002).

The minimal criteria for multipotent human mesenchymal stromal cells (MSC) has been set out by the International Society for Cellular Therapy (Dominici et al Cytotherapy (2006) Vol. 8, No. 4, 315-317). They propose three criteria to define human MSC: adherence to plastic, specific surface antigen expression and multipotent differentiation potential. In particular they stated that "First, MSCs must be plastic-adherent when maintained in standard culture conditions using tissue culture flasks. Second, ≥95% of the MSC population must express CD105, CD73 and CD90, as measured by flow cytometry. Additionally, these cells must lack expression (52% positive) of CD45, CD34, CD14 or CD11b, CD79a or CD19 and HLA class II (HLA-DR). Third, the cells must be able to differentiate to osteoblasts, adipocytes and chondroblasts under standard in vitro differentiating conditions."

Dominici et al also stated that the biologic property that most uniquely identifies MSC is their capacity for trilineage mesenchymal differentiation into osteoblasts, adipocytes and chondroblasts using standard in vitro tissue culture-differentiating conditions. They confirmed that differentiation to osteoblasts can be demonstrated by staining with Alizarin red or von Kossa staining, adipocyte differentiation can most readily be demonstrated by staining with Oil red O and chondroblast differentiation can be demonstrated by staining with Alcian blue or immunohistochemical staining for collage type II. Dominici et al state that kits for such assays are commercially available and that demonstrating differentiation should be feasible for all investigators.

Dominici et al also recognise that novel surface markers may be identified in the future that could also be used to define human MSCs. Three such markers are now known: CD49a, SSEA-4 and STRO-1.

Rider et al reported that CD49a+ clones have enhanced expression of CD90 and CD105 compared to unsorted cells and demonstrated that CD49a+ clones readily underwent multilineage differentiation into fat, bone and cartilage compared to unsorted cells, supporting the use of alpha-1 integrin (CD49a) selection for the enrichment of mesenchymal stem cells and provided a strategy for selecting the most multipotent cells from a heterogenous pool of bone marrow mononuclear stem cells (Rider et al. J. Mol. Hist (2007) 38:449-458). Rider et al also report that CFU-F cells are associated with the expression of CD49a, that CD49a expressing CFU-F cells also co-express STRO-1, and CD49a can be used to isolate MSCs from rats and mice in addition to humans indicating that it may be conserved marker for enrichment.

Gang et al report that the stage specific embryonic antigen SSEA-4, commonly used as a marker for undifferentiated pluripotent human embryonic stem cells and cleavage to blastocyst stage embryos also identifies the adult human mesenchymal stem cell population and can be used to isolate MSCs (Gang et al., Blood 2007; 109:1743-1751). Gang et al also describe the use of a monoclonal antibody that binds the surface marker STRO-1 in the enrichment of clonogenic stromal cells (CFU-F)—so-called STRO-1+$^{bright}$.

Embryonic Stem Cells

Embryonic stem cells may be isolated from blastocysts of members of primate species (Thomson et al., Proc. Natl. Acad. Sci. USA 92:7844, 1995). Human embryonic stem (hES) cells can be prepared from human blastocyst cells using the techniques described by Thomson et al. (U.S. Pat. No. 5,843,780; Science 282:1145, 1998; Curr. Top. Dev. Biol. 38:133 ff., 1998) and Reubinoff et al, Nature Biotech. 18:399, 2000.

Briefly, human blastocysts may be obtained from human in vivo preimplantation embryos. Alternatively, in vitro fertilized (IVF) embryos can be used, or one cell human embryos can be expanded to the blastocyst stage (Bongso et al., Hum Reprod 4: 706, 1989). Human embryos are cultured to the blastocyst stage in G1.2 and G2.2 medium (Gardner et al., Fertil. Steril. 69:84, 1998). Blastocysts that develop are selected for embryonic stem cell isolation. The zona pellucida is removed from blastocysts by brief exposure to pronase (Sigma). The inner cell masses are isolated by immunosurgery, in which blastocysts are exposed to a 1:50 dilution of rabbit anti-human spleen cell antiserum for 30 minutes, then washed for 5 minutes three times in DMEM, and exposed to a 1:5 dilution of Guinea pig complement (Gibco) for 3 minutes (see Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps either by exposure to calcium and magnesium-free phosphate-buffered saline (PBS) with 1 mM EDTA, by exposure to dispase or trypsin, or by mechanical dissociation with a micropipette; and then replated on mEF in fresh medium. Dissociated cells are replated on mEF feeder layers in fresh embryonic stem (ES) medium, and observed for colony formation. Colonies demonstrating undifferentiated morphology are individually selected by micropipette, mechanically dissociated into clumps, and replated. Embryonic stem cell-like morphology is characterized as compact colonies with apparently high nucleus to cytoplasm ratio and prominent nucleoli. Resulting embryonic stem cells are then routinely split every 1-2 weeks by brief trypsinization, exposure to Dulbecco's PBS (without calcium or magnesium and with 2 mM EDTA), exposure to type IV collagenase (about 0.200 U/mL; Gibco) or by selection of individual colonies by micropipette. Clump sizes of about 50 to 100 cells are optimal.

Induced Pluripotent Stem Cells

Induced pluripotent stem cells, commonly abbreviated as iPS cells or iPSCs, are a type of pluripotent stem cell artificially derived from a non-pluripotent cell, typically an adult somatic cell, for example fibroblasts, lung or B cells, by inserting certain genes. PS cells are reviewed and discussed in Takahashi, K. & Yamanaka (Induction of pluripotent stem cells from mouse embryonic and adult fibroblast cultures by defined factors. Cell 2006; 126:663-676), Yamanaka S, et. al. (Yamanaka S, et al. Induction of Pluripotent Stem Cells from Adult Human Fibroblasts by Defined Factors. doi:10.1016/j.cell.2007.11.019, and Yamanaka S, et. al. Generation of germline-competent induced pluripotent stem cells. Nature 2007; 448:313-7), Wernig M, et. al. (n vitro reprogramming of fibroblasts into a pluripotent ES-cell-like state. Nature 2007; 448:318-24), Maherali N, et. al. (Directly reprogrammed fibroblasts show global epigenetic remodeling and widespread tissue contribution. Cell Stem Cell 2007; 1:55-70) and Thomson J A, Yu J, et al. (Induced Pluripotent Stem Cell Lines Derived from Human Somatic Cells. Science DOI: 10.1126/science.1151526) and Takahashi et al., (Induction of pluripotent stem cells from adult human fibroblasts by defined factors. Cell. (2007) 131(5):861-72.), all incorporated herein by reference.

iPS cells are typically derived by transfection of certain stem cell-associated genes into non-pluripotent cells, such as adult fibroblasts. Transfection is typically achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic infection.

Sources of Pluripotent Cells

Several methods have now been provided for the isolation of pluripotent stem cells that do not lead to the destruction of an embryo, e.g. by transforming (inducing) adult somatic cells or germ cells. These methods include:

1. Reprogramming by nuclear transfer. This technique involves the transfer of a nucleus from a somatic cell into an oocyte or zygote. In some situations this may lead to the creation of an animal-human hybrid cell. For example, cells may be created by the fusion of a human somatic cell with an animal oocyte or zygote or fusion of a human oocyte or zygote with an animal somatic cell.

2. Reprogramming by fusion with embryonic stem cells. This technique involves the fusion of a somatic cell with an embryonic stem cell. This technique may also lead to the creation of animal-human hybrid cells, as in 1 above.

3. Spontaneous re-programming by culture. This technique involves the generation of pluripotent cells from non-pluripotent cells after long term culture. For example, pluripotent embryonic germ (EG) cells have been generated by long-term culture of primordial germ cells (PGC) (Matsui et al., Derivation of pluripotential embryonic stem cells from murine primordial germ cells in culture. Cell 70, 841-847, 1992, incorporated herein by reference). The development of pluripotent stem cells after prolonged culture of bone marrow-derived cells has also been reported (Jiang et al., Pluripotency of mesenchymal stem cells derived from adult marrow. Nature 418, 41-49, 2002, incorporated herein by reference). They designated these cells multipotent adult progenitor cells (MAPCs). Shinohara et al also demonstrated that pluripotent stem cells can be generated during the course of culture of germline stem (GS) cells from neonate mouse testes, which they designated multipotent germline stem (mGS) cells (Kanatsu-Shinohara et al., Generation of pluripotent stem cells from neonatal mouse testis. Cell 119, 1001-1012, 2004).

4. Reprogramming by defined factors. For example the generation of iPS cells by the retrovirus-mediated introduction of transcription factors (such as Oct-3/4, Sox2, c-Myc, and KLF4) into mouse embryonic or adult fibroblasts, e.g. as described above. Kaji et al (Virus-free induction of pluripotency and subsequent excision of reprogramming factors. Nature. Online publication 1 Mar. 2009) also describe the non-viral transfection of a single multiprotein expression vector, which comprises the coding sequences of c-Myc, Klf4, Oct4 and Sox2 linked with 2A peptides, that can reprogram both mouse and human fibroblasts. iPS cells produced with this non-viral vector show robust expression of pluripotency markers, indicating a reprogrammed state confirmed functionally by in vitro differentiation assays and formation of adult chimaeric mice. They succeeded in establishing reprogrammed human cell lines from embryonic fibroblasts with robust expression of pluripotency markers.

Methods 1-4 are described and discussed by Shinya Yamanaka in Strategies and New Developments in the Generation of Patient-Specific Pluripotent Stem Cells (Cell Stem Cell 1, July 2007 a2007 Elsevier Inc), incorporated herein by reference.

5. Derivation of hESC lines from single blastomeres or biopsied blastomeres. See Klimanskaya I, Chung Y, Becker S, Lu S J, Lanza R. Human embryonic stem cell lines derived from single blastomeres. Nature 2006; 444:512, Lei et al Xeno-free derivation and culture of human embryonic stem cells: current status, problems and challenges. Cell Research (2007) 17:682-688, Chung Y, Klimanskaya I, Becker S, et al. Embryonic and extraembryonic stem cell lines derived from single mouse blastomeres. Nature. 2006; 439:216-219. Klimanskaya I, Chung Y, Becker S, et al. Human embryonic stem cell lines derived from single blastomeres. Nature. 2006; 444:481-485. Chung Y, Klimanskaya I, Becker S, et al. Human embryonic stem cell lines generated without embryo destruction. Cell Stem Cell. 2008; 2:113-117 and Dusko Ilic et al (Derivation of human embryonic stem cell lines from biopsied blastomeres on human feeders with a minimal exposure to xenomaterials. Stem Cells And Development—paper in pre-publication), all incorporated herein by reference.

6. hESC lines obtained from arrested embryos which stopped cleavage and failed to develop to morula and blastocysts in vitro. See Zhang X, Stojkovic P, Przyborski S, et al.

Derivation of human embryonic stem cells from developing and arrested embryos. Stem Cells 2006; 24:2669-2676 and Lei et al Xeno-free derivation and culture of human embryonic stem cells: current status, problems and challenges. Cell Research (2007) 17:682-688, both incorporated herein by reference.

7. Parthogenesis (or Parthenogenesis). This technique involves chemical or electrical stimulation of an unfertilised egg so as to cause it to develop into a blastomere from which embryonic stem cells may be derived. For example, see Lin et al. Multilineage potential of homozygous stem cells derived from metaphase II oocytes. Stem Cells. 2003; 21(2): 152-61 who employed the chemical activation of nonfertilized metaphase II oocytes to produce stem cells.

8. Stem cells of fetal origin. These cells lie between embryonic and adult stem cells in terms of potentiality and may be used to derive pluripotent or multipotent cells. Human umbilical-cord-derived fetal mesenchymal stem cells (UC fMSCs) expressing markers of pluripotency (including Nanog, Oct-4, Sox-2, Rex-1, SSEA-3, SSEA-4, Tra-1-60, and Tra-1-81, minimal evidence of senescence as shown by β-galactosidase staining, and the consistent expression of telomerase activity) have been successfully derived by Chris H. Jo et al (Fetal mesenchymal stem cells derived from human umbilical cord sustain primitive characteristics during extensive expansion. Cell Tissue Res (2008) 334:423-433, incorporated herein by reference). Winston Costa Pereira et al (Reproducible methodology for the isolation of mesenchymal stem cells from human umbilical cord and its potential for cardiomyocyte generation J Tissue Eng Regen Med 2008; 2: 394-399, incorporated herein by reference) isolated a pure population of mesenchymal stem cells from Wharton's jelly of the human umbilical cord. Mesenchymal stem cells derived from Wharton's jelly are also reviewed in Troyer & Weiss (Concise Review: Wharton's Jelly-Derived Cells Are a primitive Stromal Cell Population. Stem Cells 2008:26:591-599). Kim et al (Ex vivo characteristics of human amniotic membrane-derived stem cells. Cloning Stem Cells 2007 Winter; 9(4): 581-94, incorporated herein by reference) succeeded in isolating human amniotic membrane-derived mesenchymal cells from human amniotic membranes. Umbilical cord is a tissue that is normally discarded and stem cells derived from this tissue have tended not to attract moral or ethical objection.

9. Chung et al. [(2008) Human Embryonic Stem Cell Lines Generated without Embryo Destruction. Cell Stem Cell. 2(2) 113-117. Epub 2008 Jan. 10] describes the generation of human embryonic stem cell lines with the destruction of an embryo.

Induced pluripotent stem cells have the advantage that they can be obtained by a method that does not cause the destruction of an embryo, more particularly by a method that does not cause the destruction of a human or mammalian embryo. The method described by Chung et al (item 9 above) also permits obtaining of human embryonic stem cells by a method that does not cause the destruction of a human embryo.

As such, aspects of the invention may be performed or put into practice by using cells that have not been prepared exclusively by a method which necessarily involves the destruction of human or animal embryos from which those cells may be derived. This optional limitation is specifically intended to take account of Decision G0002/06 of 25 Nov. 2008 of the Enlarged Board of Appeal of the European Patent Office.

Cell Proliferation

The present invention is based in part on the finding that stem cell proliferation (i.e. growth rate) is inversely correlated with GSTT1 expression. 'Cell proliferation' as used herein refers to an increase in cell number by cell division.

The present inventors have unexpectedly found that stem cells having a lower level of GSTT1 expression proliferate faster (i.e. they have a higher growth rate). Cell proliferation/growth rate can be measured as the time taken for a cell to divide into two daughter cells—i.e. the cell doubling time.

Cell proliferation, cell doubling time and/or growth rates can be determined routinely by methods well known to those of skill in the art.

The stem cells having reduced GSTT1 gene expression and/or GSTT1 protein expression and/or GSTT1 activity, and having an increased growth rate have a cell doubling time which is less than a reference value for cell doubling time for that stem cell type.

A reference value may be a known and/or published cell doubling time for that stem cell type, or may be an average (i.e. a mean) cell doubling time for that stem cell type. In some embodiments, the reference cell doubling time may be or may have been determined empirically.

Cell proliferation, cell doubling time and/or growth rates can be compared between cells—e.g. between a stem cell having a homozygous wildtype genotype for GSTT1 and a stem cell not having a homozygous wildtype genotype for GSTT1—by in vitro cell culture under the same culture conditions, and counting of cells at defined time points.

In some embodiments, the reference cell doubling time may be the cell doubling time for a stem cell having the homozygous wildtype genotype for GSTT1 (GSTT1+/GSTT1+). In some embodiments, the stem cells having an increased growth rate have a cell doubling time which is less than 100%, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% of the reference cell doubling time.

Clonigenic Potential

The present invention is based in part on the finding that clonigenic potential of stem cells is inversely correlated with GSTT1 expression. That is, stem cells having reduced GSTT1 gene expression and/or GSTT1 protein expression and/or GSTT1 activity have increased clonigenic potential. 'Clonigenic potential' as used herein refers to the ability of a stem cell to self-renew.

For example, for MSC, clonigenic potential can be measured by analysis of colony-forming unit fibroblasts (CFU-F). For example, CFU-F analysis can be performed as follows:
  (i) seeding bone marrow mononuclear cells into 6-well culture plates at 0.3, 1.0, and $3.0 \times 10^5$ cells per well in α-MEM supplemented with 20% (v/v) FBS, 2 mM l-glutamine, 100 µM l-ascorbate-2-phosphate, 50 U/mL penicillin, 50 mg/mL streptomycin, and β-mercaptoethanol ($5 \times 10^{-5}$ M).
  (ii) incubating cells at 37° C. in 5% $CO_2$ and >90% humidity for 12 days;
  (iii) washing cells with PBS and fixing for 20 min in 1% (w/v) paraformaldehyde in PBS;
  (iv) staining fixed cells with 0.1% (w/v) toluidine blue (in 1% paraformaldehyde solution) for 1 h, and;
  (v) counting CFU-F;
  wherein aggregates of greater than 50 cells are scored as CFU-F.

The stem cells having increased clonigenic potential have an increased frequency of CFU-F as compared to a reference value for CFU-F for that stem cell type.

A reference value may be a known and/or published CFU-F frequency for that stem cell type, or may be an average (i.e. a mean) CFU-F frequency for that stem cell type. In some embodiments, the reference CFU-F frequency may be or may have been determined empirically.

In some embodiments, the reference CFU-F frequency may be the CFU-F frequency for a stem cell having the homozygous wildtype genotype for GSTT1 (GSTT1+/GSTT1+).

In some embodiments, the stem cells having and increased clonigenic potential have a CFU-F frequency which is an increase of 0.1%, 0.15% 0.2%, 0.25%, 0.3%, 0.35%, 0.4%, 0.5%, 0.75%, 1%, 1.25%, 1.5%, 1.75%, 2%, 2.5%, 3%, 3.5%, 4%, 4.5%, 5%, 5.5%, 6%, 6.5%, 7%, 7.5%, 8%, 8.5%, 9%, 9.5%, 10%, 12.5%, 15%, 17.5%, 20%, 25%, 30%, 40%, 50%, 60%, 70%, 80%, 90% or 100% or more over the reference CFU-F frequency.

CFU-F frequency can be compared between cells—e.g. between a stem cell having a homozygous wildtype genotype for GSTT1 and a stem cell not having a homozygous wildtype genotype for GSTT1—by the method described above or by other methods known to those of skill in the art.

In some embodiments, a high proportion of stem cells in culture having reduced GSTT1 gene expression and/or GSTT1 protein expression and/or GSTT1 activity maintain the multipotent or pluripotent characteristics of the parent stem cell (e.g. ability of the stem cell to differentiate into specific tissue types characteristic of the type of stem cell). For example, preferably one of at least 20%, 30%, 40%, 50%, 60%, 70%, 80%, 90%, 95%, 96%, 97%, 98%, 99% or 100% of stem cells in the culture exhibit the multipotent or pluripotent characteristics of the parent stem cells. This may be measured relative to the number of cells in the starting culture that are multipotent or pluripotent. In some embodiments the increase in proportion of multipotent or pluripotent cells may be compared against a control culture of stem cells subject to corresponding culture conditions.

Tissue Formation

The stem cells having enhanced growth rates and/or clonigenic potential accordingly have enhanced tissue forming potential. That is, stem cells having reduced GSTT1 gene expression and/or GSTT1 protein expression and/or GSTT1 activity have an enhanced ability to form tissue.

'Tissue forming potential' as used herein refers to the ability of a stem cell to form a tissue. This can be the amount of tissue, e.g. the three-dimensional volume and/or weight of a tissue, or may be the quality of a tissue, e.g. the density.

For example the tissue may be bone, cartilage, muscle, tendon, ligament, fat, meniscus or nerve tissue. In some embodiments, the stem cell is an MSC and the tissue is bone tissue.

In some embodiments, the stem cells having reduced GSTT1 gene expression and/or GSTT1 protein expression and/or GSTT1 activity have an enhanced ability to form tissue in vitro and/or in vivo.

Tissue forming potential can be evaluated routinely by methods known to those of skill in the art. Typically a stem cell or population of stem cells will be placed under conditions—in vitro or in vivo—which induce the stem cells differentiate the cells towards a lineage for a particular tissue.

For example, formation of bone ex vivo can be measured as described hereinbelow.

The stem cells having enhanced tissue forming potential will form more tissue per starting cell and within a defined amount of time as compared to a reference amount of tissue for that stem cell type under the same conditions. A reference amount of tissue may be a known and/or published, or may be an average (i.e. a mean) for that stem cell type. In some embodiments, the reference amount of tissue may be or may have been determined empirically.

In some embodiments, the reference amount of tissue may be the amount of tissue formed by a stem cell having the homozygous wildtype genotype for GSTT1 (GSTT1+/GSTT1+).

Tissue forming potential can be compared between cells—e.g. between a stem cell having a homozygous wildtype genotype for GSTT1 and a stem cell not having a homozygous wildtype genotype for GSTT1—by placing the same number of stem cells under the same conditions, for differentiation into the same tissue type and for the same amount of time. The resulting tissues can then be analysed.

In some embodiments, the stem cells having enhanced tissue forming potential form more than 1 times, more than 1.1 times, more than 1.2 times, more than 1.3 times, more than 1.4 times, more than 1.5 times, more than 1.6 times, more than 1.7 times, more than 1.8 times, more than 1.9 times, more than 2 times, more than 2.1 times, more than 2.2 times, more than 2.3 times, more than 2.4 times, more than 2.5 times, more than 2.6 times, more than 2.7 times, more than 2.8 times, more than 2.9 times, more than 3 times, more than 3.1 times, more than 3.2 times, more than 3.3 times, more than 3.4 times, more than 3.5 times, more than 3.6 times, more than 3.7 times, more than 3.8 times, more than 3.9 times, more than 4 times, more than 4.1 times, more than 4.2 times, more than 4.3 times, more than 4.4 times, more than 4.5 times, more than 4.6 times, more than 4.7 times, more than 4.8 times, more than 4.9 times, or more than 5 times the amount of tissue as compared to the amount of tissue formed by the reference stem cell.

Markers

The present inventors have identified further characteristics which are correlated with GSTT1 expression.

In some embodiments, stem cells having reduced GSTT1 gene expression and/or GSTT1 protein expression and/or GSTT1 activity (i) may have enhanced colony forming capacity;
(ii) may be smaller in size
(iii) may have a longer telomere, or a reduced rate of telomere shortening
(iv) may have increased expression of STRO-1, SSEA-4, CD146 and/or PDGFRβ
(v) may have increased secretion of FGF-2, VEGF, SDF-1α, fractalkine, PDGF-BB and/or MIP-1α;
(vi) may display an enhanced ability to suppress of T cells, and;
(vii) may have decreased expression of ALP, RUNX2 and/or BSP-II;
(viii) may have increased expression of TWIST-1 and DERMO-1;

than stem cells which are homozygous wildtype for GSTT1 (GSTT1+/GSTT1+), and/or the average (i.e. mean) for that stem cell type.

These properties can readily be investigated by the skilled person.

Stem cells having one or more of these properties are therefore useful for identifying stem cells having reduced GSTT1 gene expression and/or GSTT1 protein expression and/or GSTT1 activity. Accordingly, in some embodiments the methods of the invention may comprises a pre-screening step, wherein a population of stem cells or a sample obtained from an individual may be analysed for one or more of these characteristics prior to determination of GSTT1 gene expression and/or GSTT1 protein expression and/or GSTT1 activity, and/or GSTT1 genotype.

In some embodiments, the stem cells having reduced GSTT1 gene expression and/or GSTT1 protein expression and/or GSTT1 activity have a size which is less than 100%, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% of the size of a reference stem cell, wherein the reference cell may be a stem cell which is homozygous wildtype for GSTT1 (GSTT1+/GSTT1+), or the average (i.e. mean) size for that stem cell type.

In some embodiments, the stem cells having reduced GSTT1 gene expression and/or GSTT1 protein expression and/or GSTT1 activity have a rate of telomere shortening which is less than 100%, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, or less than 5% of the rate of telomere shortening of a reference stem cell, wherein the reference cell may be a stem cell which is homozygous wildtype for GSTT1 (GSTT1+/GSTT1+), or the average (i.e. mean) rate of telomere shortening for that stem cell type.

The rate of telomere shortening can be investigated e.g. as in Samsonraj et al., Telomere length analysis of human mesenchymal stem cells by quantitative PCR, Gene 2013.

In some embodiments, the stem cells having reduced GSTT1 gene expression and/or GSTT1 protein expression and/or GSTT1 activity have a relatively higher expression of growth factor receptors as compared to a reference stem cell, wherein the reference cell may be a stem cell which is homozygous wildtype for GSTT1 (GSTT1+/GSTT1+), or the average (i.e. mean) expression of growth factor receptors for that stem cell type.

For example, the stem cells having reduced GSTT1 gene expression and/or GSTT1 protein expression and/or GSTT1 activity may have relatively higher expression of one or more of STRO-1, SSEA-4, CD146 and/or PDGFRβ. In some embodiments, the level of expression may be more than 1 times, more than 1.1 times, more than 1.2 times, more than 1.3 times, more than 1.4 times, more than 1.5 times, more than 1.6 times, more than 1.7 times, more than 1.8 times, more than 1.9 times, more than 2 times, more than 2.1 times, more than 2.2 times, more than 2.3 times, more than 2.4 times, more than 2.5 times, more than 2.6 times, more than 2.7 times, more than 2.8 times, more than 2.9 times, more than 3 times, more than 3.1 times, more than 3.2 times, more than 3.3 times, more than 3.4 times, more than 3.5 times, more than 3.6 times, more than 3.7 times, more than 3.8 times, more than 3.9 times, more than 4 times, more than 4.1 times, more than 4.2 times, more than 4.3 times, more than 4.4 times, more than 4.5 times, more than 4.6 times, more than 4.7 times, more than 4.8 times, more than 4.9 times, or more than 5 times compared to the expression of a reference stem cell.

In some embodiments, a relatively higher proportion of cells having reduced GSTT1 gene expression and/or GSTT1 protein expression and/or GSTT1 activity will be positive for expression one or more of STRO-1, SSEA-4, CD146 and/or PDGFRβ as compared to a reference stem cell.

Expression of the growth factor receptors can be determined by various means known to those skilled in the art, for example by flow cytometry and/or gene expression analysis.

In some embodiments, the stem cells having reduced GSTT1 gene expression and/or GSTT1 protein expression and/or GSTT1 activity have a relatively higher secretion of factors involved in wound healing as compared to a reference stem cell, wherein the reference cell may be a stem cell which is homozygous wildtype for GSTT1 (GSTT1+/GSTT1+), or the average (i.e. mean) level of secretion of factors involved in wound healing for that stem cell type.

For example, the stem cells having reduced GSTT1 gene expression and/or GSTT1 protein expression and/or GSTT1 activity may secrete relatively higher amounts of FGF-2, VEGF, SDF-1α, fractalkine, PDGF-BB and/or MIP-1α. In some embodiments, the level of secretion may be more than 1 times, more than 1.1 times, more than 1.2 times, more than 1.3 times, more than 1.4 times, more than 1.5 times, more than 1.6 times, more than 1.7 times, more than 1.8 times, more than 1.9 times, more than 2 times, more than 2.1 times, more than 2.2 times, more than 2.3 times, more than 2.4 times, more than 2.5 times, more than 2.6 times, more than 2.7 times, more than 2.8 times, more than 2.9 times, more than 3 times, more than 3.1 times, more than 3.2 times, more than 3.3 times, more than 3.4 times, more than 3.5 times, more than 3.6 times, more than 3.7 times, more than 3.8 times, more than 3.9 times, more than 4 times, more than 4.1 times, more than 4.2 times, more than 4.3 times, more than 4.4 times, more than 4.5 times, more than 4.6 times, more than 4.7 times, more than 4.8 times, more than 4.9 times, or more than 5 times the secretion by a reference stem cell.

Expression of the factors involved in wound healing can be determined by various means known to those skilled in the art, for example by ELISA gene expression analysis.

In some embodiments, the stem cells having reduced GSTT1 gene expression and/or GSTT1 protein expression and/or GSTT1 activity have an enhanced ability to suppress T cells as compared to a reference stem cell, wherein the reference cell is a stem cell which is homozygous wildtype for GSTT1 (GSTT1+/GSTT1+), or the average (i.e. mean) ability to suppress T cells for that stem cell type. Assays for evaluating the ability to suppress T cells are well known to those of skill in the art. For example, T cell suppression can be measured by evaluating the ability to suppress T cell proliferation.

In some embodiments, the stem cells having reduced GSTT1 gene expression and/or GSTT1 protein expression and/or GSTT1 activity have reduced expression of osteogenic markers. For example, the stem cells may have decreased expression of ALP, RUNX2 and/or BSP-II than stem cells which are homozygous wildtype for GSTT1 (GSTT1+/GSTT1+), and/or the average (i.e. mean) expression for that stem cell type. In some embodiments, the level of expression may be less than 1 times, less than 0.9 times, less than 0.9 times, less than 0.8 times, less than 0.7 times, less than 0.6 times, less than 0.5 times, less than 0.4 times, less than 0.3 times, less than 0.2 times, or less than 0.1 times the level expression compared to the level of expression of a reference stem cell.

In some embodiments the stem cells having reduced GSTT1 gene expression and/or GSTT1 protein expression and/or GSTT1 activity have increased expression of mesodermal genes. For example, the stem cells may have increased expression of TWIST-1 and/or DERMO-1 as compared to stem cells which are homozygous wildtype for GSTT1 (GSTT1+/GSTT1+), and/or the average (i.e. mean) expression for that stem cell type. In some embodiments, the level of expression may be more than 1 times, more than 1.1 times, more than 1.2 times, more than 1.3 times, more than 1.4 times, more than 1.5 times, more than 1.6 times, more than 1.7 times, more than 1.8 times, more than 1.9 times, more than 2 times, more than 2.1 times, more than 2.2 times, more than 2.3 times, more than 2.4 times, more than 2.5 times, more than 2.6 times, more than 2.7 times, more than 2.8 times, more than 2.9 times, more than 3 times, more than 3.1 times, more than 3.2 times, more than 3.3 times, more than 3.4 times, more than 3.5 times, more than 3.6 times, more than 3.7 times, more than 3.8 times, more than 3.9 times, more than 4 times, more than 4.1 times, more than 4.2 times, more than 4.3 times, more than 4.4 times, more than 4.5 times, more than 4.6 times, more than 4.7 times, more than 4.8 times, more than 4.9 times, or more than 5 times the level expression compared to the level of expression of a reference stem cell.

Gene expression can be determined by various means well known to those skilled in the art, for example by quantitative real-time PCR (qRT-PCR).

Methods according to the present invention may be performed in vitro or in vivo. The term "in vitro" is intended to encompass experiments with materials, biological substances, cells and/or tissues in laboratory conditions or in culture whereas the term "in vivo" is intended to encompass experiments and procedures with intact multi-cellular organisms.

Modifying GSTT1 Expression

The present inventors have discovered that the growth rate and/or tissue forming potential of stem cells can be modified by changing the level of GSTT1 gene or protein expression, or GSTT1 function.

Accordingly, the present invention provides a method for modifying a stem cell or plurality of stem cells, the method comprising contacting a stem cell or plurality of stem cells with an agent capable of modifying a stem cell to reduce GSTT1 expression and/or function.

The skilled person is well able to identify agents capable of modifying a stem cell to reduce GSTT1 gene and/or protein expression and/or function.

In some embodiments, the agent capable of modifying a stem cell to reduce GSTT1 expression and/or function may effect reduced GSTT1 gene or protein expression and/or GSTT1 function by influencing GSTT1 transcription, mRNA processing (e.g. splicing), mRNA stability, translation, post-translational processing, protein stability, protein degradation and/or GSTT1 protein function/activity.

In some embodiments the agent may be an agent which effects the level of GSTT1 mRNA. For example, the agent may knockdown GSTT1 expression by RNA interference (RNAi).

In some embodiments, the agent may be an inhibitory nucleic acid. Inhibitory nucleic acids may be an antisense or small interfering RNA, including but not limited to an shRNA or siRNA.

In some embodiments the inhibitory nucleic acid is provided on a vector. For example, in some embodiments the agent may be a lentiviral vector encoding an shRNA for GSTT1.

In some embodiments the agent may be an agent capable of altering the genome of the stem cell to reduce GSTT1 gene or protein expression and/or GSTT1 function/activity by the stem cell. For example, the agent may be capable of disrupting and/or inactivating GSTT1, and/or may integrate a DNA sequence encoding a sequence encoding a molecule capable of reducing GSTT1 gene or protein expression and/or GSTT1 function/activity.

In some embodiments the agent may be an inhibitor of GSTT1 protein. For example, the agent may be a molecule capable of binding to GSTT1 protein and inhibiting GSTT1 function/activity. In some embodiments the agent may be an antibody directed against GSTT1. In some embodiments, the agent may be a competitive inhibitor of GSTT1 function/activity.

In some embodiments the method comprises: (i) optionally isolating a stem cell or plurality of stem cells from an individual, and; (ii) contacting an isolated stem cell or plurality of stem cells in vitro with an agent capable of modifying a stem cell to reduce GSTT1 expression and/or function.

The present invention also provides a stem cell or plurality of stem cells which have been modified to reduce endogenous GSTT1 expression and/or function. In some embodiments, the stem cell(s) have been modified with an agent GSTT1 gene or protein expression and/or GSTT1 function.

Also provided is a stem cell or plurality of stem cells, which contain an agent capable of reducing GSTT1 gene or protein expression and/or GSTT1 function.

Also provided is a stem cell or plurality of stem cells, which have been modified to have decreased GSTT1 expression and/or function relative to stem cells which are homozygous for wildtype GSTT1, and/or stem cells having the average (i.e. mean) level of GSTT1 expression and/or function for that stem cell type.

Uses

The stem cells having reduced GSTT1 gene expression and/or GSTT1 protein expression and/or GSTT1 activity, and having increased growth rates and/or tissue forming potential are useful in various applications which will be immediately apparent to the skilled person.

The stem may be useful in the generation of tissues in vitro and in vivo. As such, tissues may be generated in vitro which are suitable for implantation into patients or cells identified or selected by the methods of the invention may be administered or implanted into patients in order to provide a medical treatment, e.g. the regeneration of tissue.

Accordingly, the present invention provides a stem cell or plurality of stem cells according to the invention for use in a method of medical treatment.

The stem cell or plurality of stem cells according to the invention may also be used in the manufacture of a medicament for use in a method of medical treatment.

Furthermore, the present invention provides a method of regenerating tissue in a patient in need of such treatment, the method comprising administering to the patient a therapeutic number of stem cells according to the invention.

The stem cell or plurality of stem cells according to the invention are also provided for use in a method of treating a bone fracture, or in the repair of cartilage tissue, the method comprising administering the stem cells to tissue surrounding the fracture or to the site of the injury.

Prevention or treatment using stem cells having reduced GSTT1 gene expression and/or GSTT1 protein expression and/or GSTT1 activity may involve the repair, regeneration or replacement of tissue, particularly connective tissue such as bone, cartilage, muscle, fat, ligament or tendon.

In patients having a deterioration of one of these tissues, stem cells, preferably mesenchymal stem cells, having reduced GSTT1 gene expression and/or GSTT1 protein expression and/or GSTT1 activity administered to the site of deterioration may proliferate and differentiate into the appropriate connective tissue, thereby providing for replacement/regeneration of the damaged tissue and treatment of the injury.

Alternatively, connective tissue obtained from in vitro culture of mesenchymal stem cells having reduced GSTT1 gene expression and/or GSTT1 protein expression and/or GSTT1 activity may be collected and implanted at the site of injury or disease to replace damaged or deteriorated tissue. The damaged or deteriorated tissue may optionally first be excised from the site of injury or disease.

Accordingly, stem cells having reduced GSTT1 gene expression and/or GSTT1 protein expression and/or GSTT1 activity are useful in wound healing in vivo, including tissue repair, regeneration and/or replacement (e.g. healing of scar tissue or a broken bone) effected by direct application of stem cells, preferably mesenchymal stem cells, having reduced GSTT1 gene expression and/or GSTT1 protein expression and/or GSTT1 activity, to the patient requiring treatment. Stem cells having reduced GSTT1 gene expression and/or GSTT1 protein expression and/or GSTT1 activity is also useful in the in vitro generation of tissue suitable for implantation into a patient in need of tissue repair, regeneration and/or replacement.

Bone Fracture

In some aspects the present invention is concerned with the therapeutic use (human and/or veterinary) of stem cells having reduced GSTT1 gene expression and/or GSTT1 protein expression and/or GSTT1 activity to treat bone fracture.

Bone fracture is a medical condition. In this application "fracture" includes damage or injury to bone in which a bone is cracked, broken or chipped. A break refers to discontinuity in the bone. A fracture may be caused by physical impact, or mechanical stress or by medical conditions such as osteoporosis or osteoarthritis.

Orthopaedic classification of fractures includes closed or open and simple or multi-fragmentary fractures. In closed fractures the skin remains intact, whilst in an open fracture the bone may be exposed through the wound site, which brings a higher risk of infection. Simple fractures occur along a single line, tending to divide the bone in two. Multi-fragmentary fractures spilt the bone into multiple pieces.

Other fracture types include, compression fracture, compacted fracture, spiral fracture, complete and incomplete fractures, transverse, linear and oblique fractures and comminuted fractures.

In most subjects bone healing (fracture union) occurs naturally and is initiated following injury. Bleeding normally leads to clotting and attraction of white blood cells and fibroblasts, followed by production of collagen fibres. This is followed by bone matrix (calcium hydroxyapatite) deposition (mineralisation) transforming the collagen matrix into bone. Immature re-generated bone is typically weaker than mature bone and over time the immature bone undergoes a process of remodelling to produce mature "lamellar" bone. The complete bone healing process takes considerable time, typically many months.

Bones in which fractures occur and which may benefit from treatment with stem cells having reduced GSTT1 gene expression and/or GSTT1 protein expression and/or GSTT1 activity include all bone types, particularly all mammalian bones including, but not limited to, long bones (e.g. femur, humerus, phalanges), short bones (e.g. carpals, tarsals), flat bones (e.g. cranium, ribs, scapula, sternum, pelvic girdle), irregular bones (e.g. vertebrae), sesamoid bones (e.g. patella).

Bones in which fractures occur and which may benefit from treatment using stem cells having reduced GSTT1 gene expression and/or GSTT1 protein expression and/or GSTT1 activity include skeletal bone (i.e. any bone of the skeleton), bones of the cranio-facial region, bones of the axial skeleton (e.g. vertebrae, ribs), appendicular bone (e.g. of the limbs), bone of the pelvic skeleton (e.g. pelvis).

Bones in which fractures occur and which may benefit from treatment using stem cells having reduced GSTT1 gene expression and/or GSTT1 protein expression and/or GSTT1 activity also include those of the head (skull) and neck, including those of the face such as the jaw, nose and cheek. Stem cells having reduced GSTT1 gene expression and/or GSTT1 protein expression and/or GSTT1 activity may be used to assist in repair or regeneration of bone during dental or facial or cranial surgery, which may include reconstruction of bones (as distinct from teeth) of the face and/or mouth, e.g. including the jawbone.

Bone fracture also includes pathological porosity, such as that exhibited by subjects with osteoporosis.

Stem cells having reduced GSTT1 gene expression and/or GSTT1 protein expression and/or GSTT1 activity and pharmaceutical compositions and medicaments comprising such stem cells are provided for use in a method of treatment of bone fracture in a mammalian subject.

Treatment may comprise wound healing in bone. The treatment may involve repair, regeneration and growth of bone. Stem cells having reduced GSTT1 gene expression and/or GSTT1 protein expression and/or GSTT1 activity facilitates fracture repair by facilitating new bone growth. Stem cells having reduced GSTT1 gene expression and/or GSTT1 protein expression and/or GSTT1 activity acts to improve the speed of fracture repair enabling bone healing to occur faster leading to improved recovery time from injury. Treatment may lead to improved bone strength.

Treatment may also include treatment of osteoporosis or osteoarthritis.

Administration of stem cells having reduced GSTT1 gene expression and/or GSTT1 protein expression and/or GSTT1 activity is preferably to the tissue surrounding the fracture. This may include administration directly to bone tissue in which the fracture has occurred. Administration may be to connective tissue surrounding the bone or fracture or to vasculature (e.g. blood vessels) near to and supplying the bone. Administration may be directly to the site of injury and may be to a callus formed by initial healing of the wound.

Medicaments and pharmaceutical compositions according to the present invention may be formulated for administration by a number of routes.

Administration is preferably of a "therapeutically effective number" of stem cells having reduced GSTT1 gene expression and/or GSTT1 protein expression and/or GSTT1 activity, being sufficient to improve healing of the bone fracture compared to a corresponding untreated fracture. The actual number and time-course of administration will depend on the nature and severity of the fracture. Prescription of treatment is within the responsibility of general practitioners and other medical doctors, and will typically take account of the nature of the fracture, the condition of the individual patient, the site of delivery, the method of administration and other factors known to practitioners. Single or multiple administrations of stem cells having reduced GSTT1 gene expression and/or GSTT1 protein expression and/or GSTT1 activity may be administered in accordance with the guidance of the prescribing medical practitioner.

Stem cells having reduced GSTT1 gene expression and/or GSTT1 protein expression and/or GSTT1 activity may be used to treat bone fracture alongside other treatments, such as administration of pain relieving or anti-inflammatory medicaments, immobilisation and setting of the bone, e.g. immobilising the injured limb in a plaster cast, surgical intervention, e.g. to re-set a bone or move a bone to correct displacement, angulation or dislocation. If surgery is required stem cells having reduced GSTT1 gene expression and/or GSTT1 protein expression and/or GSTT1 activity may be administered directly to (e.g. applied to) the fracture during the surgical procedure.

Methods for Selecting a Stem Cell Donor

In another aspect of the present invention, methods for selecting a stem cell donor are provided. "Selecting a stem cell donor" may comprise identifying a suitable donor of bone marrow for obtaining stem cells.

In some embodiments, the methods comprise determining the genotype for GSTT1 in a nucleic acid containing sample obtained from an individual. In some embodiments, the sample may be, or may be derived from, e.g. a tissue or liquid sample obtained from an individual (e.g. a buccal swab, blood or skin punch sample). In some embodiments, they comprise a step of preparing or extracting nucleic acid from the sample.

In some embodiments, the nucleic acid may be DNA, e.g. genomic DNA. In some embodiments, the nucleic acid may be RNA. In such embodiments, the methods may comprise preparing cDNA from the RNA, e.g. by reverse transcription.

In some embodiments, the methods comprise detecting and/or quantifying a GSTT1 nucleic acid in the sample.

A GSTT1 nucleic acid as used herein refers to a nucleic acid which is comprised in, or transcribed from, the GSTT1 gene locus. In some embodiments, a GSTT1 nucleic acid may be a nucleic acid which encodes a GSTT1 protein. That is, a GSTT1 nucleic acid may be a nucleic acid which can be transcribed and subsequently translated into a GSTT1 protein, or a nucleic acid which can be translated into a GSTT1 protein, as defined hereinabove.

In some embodiments, the methods comprise detecting the absence of a GSTT1 nucleic acid in the sample.

In some embodiments, the methods comprise contacting a nucleic acid containing sample with one or more oligonucleotides suitable for use in the detection and/or quantification of a GSTT1 nucleic acid in a nucleic acid containing sample. In some embodiments, the methods comprise contacting a nucleic acid containing sample with one or more oligonucleotides suitable for use in the detection of the absence of a GSTT1 nucleic acid in a nucleic acid containing sample.

In some embodiments, the method comprises detecting the presence of a GSTT1 allele in the nucleic acid containing sample. In some embodiments, the GSTT1 allele is one or more of the wildtype GSTT1 allele, a GSTT1 allele which is known and/or which would be predicted to result in decreased expression of GSTT1 relative to the wildtype GSTT1 allele, and the GSTT1 null (i.e. deletion) allele. In some embodiments, the methods comprise contacting a nucleic acid containing sample with oligonucleotides for use to detect a GSTT1 allele in the nucleic acid containing sample.

In some embodiments, the oligonucleotides (e.g. primers) are capable of amplifying DNA fragment only where a particular GSTT1 allele is present in the sample. For example, oligonucleotides for detecting the presence of the wildtype GSTT1 allele may anneal to DNA sequences which are absent from a DNA sequence comprising the GSTT1 null (deletion) allele. For example, oligonucleotides for detecting the presence of the GSTT1 deletion allele may anneal to DNA sequences which do not produce an amplification product from a DNA sequence comprising the wildtype GSTT1 allele. Amplification products of a PCR amplification reaction can be analysed by means well known to the skilled person, for example, by gel electrophoresis of PCR amplification reaction products and visualisation of amplified DNA.

In some embodiments, the oligonucleotides used in the method may comprise one or more of the primers for the detection of GSTT1 disclosed in Buchard et al., J Mol Diagn, (2007) 9(5): 612-617 (hereby incorporated by reference in its entirety), at Tables 1 and 2 on pages 613 and 614. In some embodiments, the oligonucleotides may comprise one or more of the following oligonucleotides:

| Primer set | Forward Primer | Reverse Primer |
|---|---|---|
| GSTT1_Gene | 5'-TCTTTTGCATAGAGACCATGACCAG-3' | 5'-CTCCCTACTCCAGTAACTCCCGACT-3' |
| GSTT1_Deletion | 5'-GAAGCCCAAGAATGGGTGTGTGTG-3' | 5'-TGTCCCCATGGCCTCCAACATT-3' |

In some embodiments the methods comprise performing a PCR reaction. In some embodiments, the methods comprise performing reverse transcription PCR (RT-PCR).

In some embodiments, the methods comprise a step of detecting and/or quantifying a GSTT1 nucleic acid in the sample.

In some embodiments, the methods comprise analysis of GSTT1 expression. In some embodiments, the methods comprise detecting and/or quantifying GSTT1 nucleic acid in a cDNA sample prepared from a nucleic acid containing sample obtained from an individual. In some embodiments, the methods comprise analysis of GSTT1 expression by RT-PCR. In some embodiments, analysis is performed using oligonucleotides (e.g. primers and probes) suitable for detecting expression of GSTT1 by RT-PCR using the TaqMan RT-PCR platform.

In some embodiments, the methods comprise selecting an individual determined to have (i) a GSTT1 genotype which is known, and/or which would be predicted, to result in decreased expression of GSTT1 relative to individuals homozygous for wildtype GSTT1, or (ii) expression of GSTT1 which is known, and/or which would be predicted to be reduced relative to GSTT1 expression by individuals homozygous for wildtype GSTT1; as a stem cell donor.

In a related aspect, the present invention provides methods for assessing the quality of stem cells produced by an individual. The methods comprise determining the GSTT1 genotype or expression of GSTT1, as described above. In such embodiments, a GSTT1 genotype which is known, and/or which would be predicted, to result in decreased expression of GSTT1 relative to individuals homozygous for wildtype GSTT1, or (ii) expression of GSTT1 which is known, and/or which would be predicted to be reduced relative to GSTT1 expression by individuals homozygous for wildtype GSTT1; is indicative of high quality stem cells.

In another aspect, the present invention provides a method for selecting a stem cell donor using a kit according to the present invention.

Kits

In some aspects of the present invention a kit for detection of GSTT1 or a GSTT1 genotype is provided. In some embodiments the kit may be suitable for selecting a stem cell donor an may include reagents or buffers suitable to process a tissue or cell sample for use in an assay for which the kit is intended. Such kits may be useful for identifying suitable donors of bone marrow for obtaining stem cells. The kits may be suitable for assessing the quality of stem cells produced by an individual.

Accordingly, a kit for determining GSTT1 expression is provided. The kit may have at least one container having a predetermined quantity of one or more reagents for determining GSTT1 expression in a sample. In some embodiments, the kit may comprise one or more reagents necessary for the quantitative or qualitative determination of the level of GSTT1 expression in a sample. In some embodiments, the kit may comprise one or more reagents for determining the level of expression of GSTT1 in a stem cell or plurality of stem cells in a sample isolated from an individual.

The skilled person is readily able to identify reagents suitable for determining the level of GSTT1 expression in a sample. Suitable reagents may include one or more, e.g. a pair of, oligonucleotide primers each having a nucleotide sequence that is complementary to a nucleotide sequence region of a GSTT1 encoding nucleic acid, e.g. DNA, mRNA, cDNA.

As such, a suitable kit may include at least one container having a predetermined quantity of one or more oligonucleotide primers useful in amplification of a GSTT1 encoding nucleic acid, e.g. by the polymerase chain reaction method (PCR), and a container (optionally the same container) having a predetermined quantity of one or more thermostable enzymes, e.g. a Taq polymerase, optionally together with a suitable buffer or solvent, optionally including one or more detectable labels and optionally also including one or more sterile reaction vessels suitable for performing the amplification experiment.

Alternatively, suitable reagents may include one or more binding agents specific for GSTT1, e.g. an antibody or aptamer, and optionally a detectable label, the reagents suitable to bind GSTT1 protein and the bound complexes suitable for detection by the conjugation to the label. For example, the kit may be suitable to perform a sandwich detection assay and may include a first GSTT1 binding agent, e.g. antibody, optionally immobilised on a solid support, a second GSTT1 binding agent, capable of binding to GSTT1 when complexed with the first GSTT1 binding agent, one or more detection reagents suitable to label or detect the complex of first binding agent:GSTT1:second binding agent; and optionally a substrate for the detection reagent and optionally a buffer.

In some embodiments, the kit contains all of the components necessary and/or sufficient to perform an assay for the determination of the level of GSTT1 expression in a sample, including all controls, instructions/directions for performing assays, and any necessary software for analysis and presentation of results.

Also provided is a kit for determining GSTT1 genotype. The kit comprises reagent(s) for determining GSTT1 genotype in a sample. In some embodiments, the kit comprises reagent(s) for determining the genotype for GSTT1 in a DNA-containing sample isolated from an individual. The skilled person is readily able to identify reagents suitable for determining GSTT1 genotype in a sample. In some embodiments, the reagents may include one or more oligonucleotide primers. In some embodiments, the kit contains all of the components necessary and/or sufficient to perform an assay for determining GSTT1 genotype in a sample, including all controls, instructions/directions for performing assays, and any necessary software for analysis and presentation of results.

In particular embodiments, the kit is capable of detecting the presence of a GSTT1 allele in the nucleic acid containing sample. In some embodiments, the GSTT1 allele is one more of the wildtype GSTT1 allele, a GSTT1 allele which is known and/or which would be predicted to result in decreased expression of GSTT1 relative to the wildtype GSTT1 allele, and the GSTT1 null (i.e. deletion) allele.

In some embodiments, the kit is capable of detecting the wildtype and deletion GSTT1 alleles, e.g. by PCR amplification. In some embodiments, the kit comprises oligonucleotides for the detection of wildtype and deletion GSTT1 alleles.

In some embodiments, the kit is suitable for detecting the presence or absence of the GSTT1 gene in a nucleic acid containing sample. In some embodiments, the sample may be obtained from an individual. In some embodiments, the nucleic acid containing sample may be, or may be derived from, e.g. a tissue or liquid sample obtained from an individual (e.g. a buccal swab, blood or skin punch sample). In some embodiments, the nucleic acid may be DNA, e.g. genomic DNA.

In some embodiments, the kit contains oligonucleotides for the detection of the wildtype and deletion GSTT1 alleles in genomic DNA.

In some embodiments, the kit comprises oligonucleotides (e.g. primers) which are capable of amplifying DNA fragment only where a particular GSTT1 allele is present in the sample. For example, oligonucleotides for detecting the presence of the wildtype GSTT1 allele may anneal to DNA sequences which are absent from a DNA sequence comprising the GSTT1 deletion allele. For example, oligonucleotides for detecting the presence of the GSTT1 deletion allele may anneal to DNA sequences which do not produce an amplification product from a DNA sequence comprising the wildtype GSTT1 allele.

In some embodiments, the kit comprises one or more of the oligonucleotide primers for the detection of GSTT1 disclosed in Buchard et al., J Mol Diagn, (2007) 9(5): 612-617, at Tables 1 and 2 on pages 613 and 614. In a particular embodiment, the kit comprises one or more oligonucleotides of the "GSTT1_Gene" and "GSTT1_Deletion" primer sets described above.

In some embodiments, the kit is capable of detecting both wildtype and deletion GSTT1 alleles in a single PCR amplification reaction (if present in a sample). In some embodiments, the kit comprises oligonucleotides suitable for use to detect wildtype and deletion GSTT1 alleles in a multiplex format.

In some embodiments, the oligonucleotides (e.g. primers and probes) are suitable for use with the TaqMan platform (Life Technologies), which is well known to the skilled person. For example, the oligonucleotides may have properties (e.g. length, composition, annealing temperature etc.) suitable for use with the TaqMan platform. In some embodiments, the oligonucleotides are suitable for detection of one or more of the wildtype GSTT1 allele, a GSTT1 allele which is known and/or which would be predicted to result in decreased expression of GSTT1 relative to the wildtype GSTT1 allele, and the GSTT1 null (i.e. deletion) allele. In some embodiments, the oligonucleotides are suitable for detection of the wildtype GSTT1 and deletion GSTT1 alleles in genomic DNA.

In some embodiments, the oligonucleotides are suitable for detection of GSTT1 in a cDNA sample prepared from a nucleic acid containing sample obtained from an individual. Accordingly, in some embodiments, the oligonucleotides are suitable for use to detect GSTT1 expression by RT-PCR. In some embodiments, the oligonucleotides (e.g. primers and probes) are suitable for detection by RT-PCR using the TaqMan RT-PCR platform.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which:

(FIG. 1A) Classification of the GST superfamily based on sequence homology and structure. (FIG. 1B) GST enzymes catalyze the conjugation of glutathione to xenobiotics.

Frequency of GSTT1 homozygous deletion across several populations.

FIG. 3.

Continuous monitoring of cell proliferation for fast and slow growing MSC lines. The number of viable cells in a culture well was assessed (Cell Index) over 5 days (time shown in hours) on the xCELLigence system. Results are shown for 2 independent cell lines representing each group, with 3 technical replicates of each. Line starting below and then crossing over and remaining above the other line=fast-growing; the other line=slow-growing.

FIGS. 4A-4D.

(FIG. 4A) Normalized microarray beadchip signal. All the slow growers (B, D and F) express GSTT1 at a modest level, while two of the fast growers (A and C) have negligible expression. (FIG. 4B) Genotyping of GSTT1. BM-MSC lines A and C are nulls (GSTT1-/-) and the remaining are positive (B, D, E, F: GSTT1+/-; 10R, 11R: GSTT1+/+). (FIG. 4C) Expression analysis by qRT-PCR. GSTT1 level is correlated with copy number of alleles. (FIG. 4D) Protein expression analysis. The expression was consistent with the 'trimodal effect'.

Figure 5A:
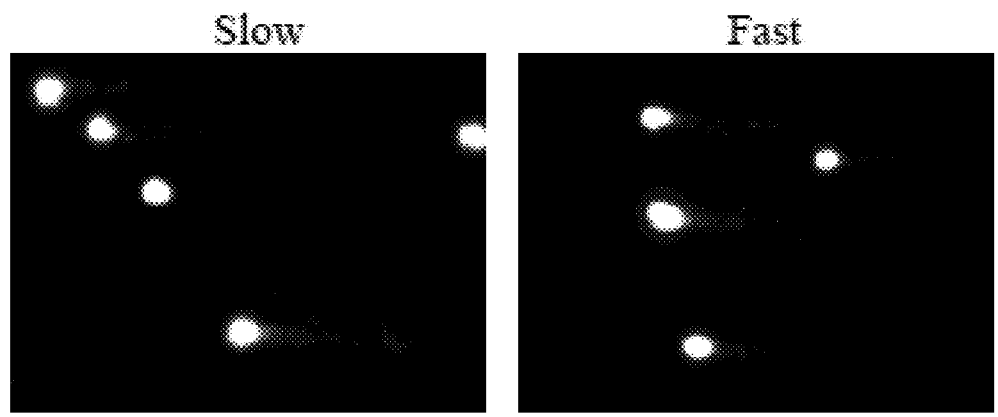
Figure 5B:
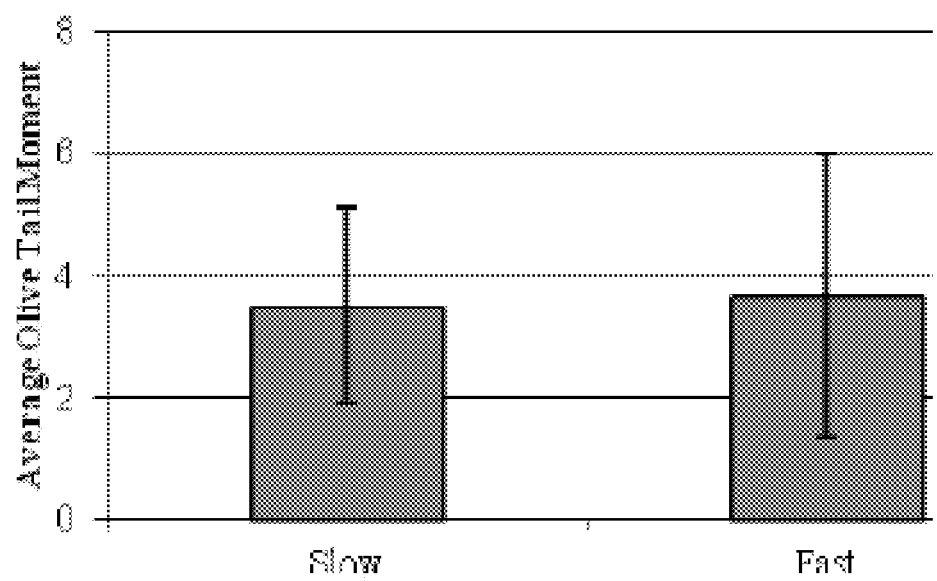

FIGS. 5A and 5B.

Evaluation of DNA damage by comet assay. Lysis and electrophoresis were performed on cells embedded in low melting point agarose on microscope slides. (FIG. 5A) Comet images after comet assay. DAPI-stained nuclei of slow and fast growers have similar extent of tail length. (FIG. 5B) Quantification of DNA lesion by olive tail moment detected inconsiderable damage in both groups.

Figure 6A:
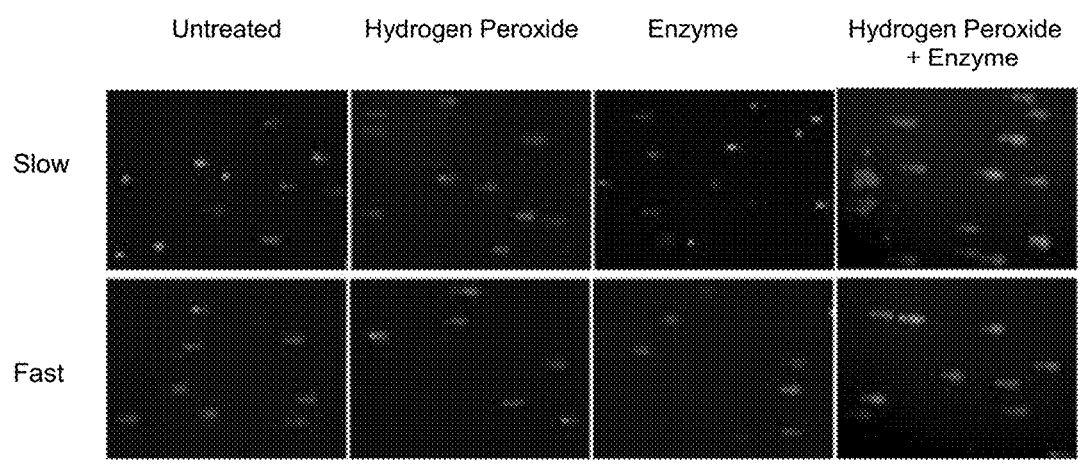
Figure 6B:
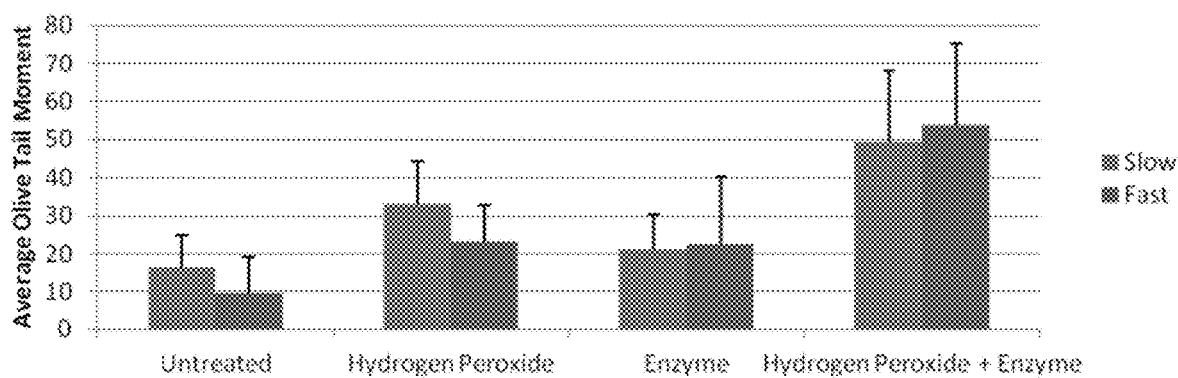

FIGS. 6A and 6B.

Evaluation of DNA damage after oxidative stress by comet assay. Embedded cells were treated with 10 μM hydrogen peroxide for 20 min before lysis and hOGG1 treatment, followed by electrophoresis. Controls: untreated, mutagen only and enzyme only. (FIG. 6A) Comet images after comet assay. The tail length increases upon hydrogen peroxide and enzyme treatments, but comparable tail lengths between the fast and slow growers. (FIG. 6B) Olive tail measurement of DNA damage. No difference detected between the groups under the various treatments.

Figure 7A:
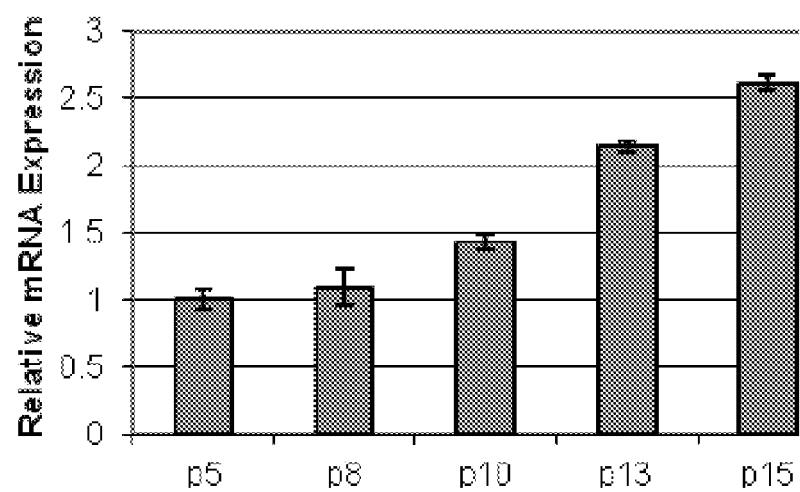
Figure 7B:
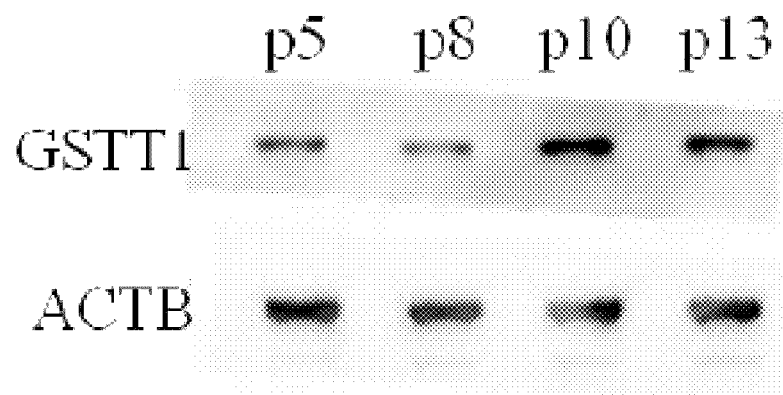

FIGS. 7A and 7B.

GSTT1 expression analysis across passages by qRT-PCR (FIG. 7A) and western blot (FIG. 7B). Expression of GSTT1 increases with passage.

FIGS. 8A-8D.

(FIG. 8A) GSTT1 knockdown efficiency. Lentiviral infection of slow growers with shRNA for GSTT1 results in decline of mRNA level by 70% compared to nonsilencing control. (FIG. 8B) Viable cell count. 80% increase in cell number seen in the knockdown in comparison to control. (FIG. 8C) EdU labeling assay. Analysis by flow cytometry after 18 h incubation of cells with 10 μM EdU and reaction with copper sulfate and 647-azide reaction. Significant increase in the population of dividing cells with the knockdown. (FIG. 8D) Real-time proliferation measurement on the xCELLigence system. Knockdown has shorter doubling time.

FIGS. 9A-9C.

Clonogenic potential assessment by CFU-F assay. 150 cells plated in 10 cm format were maintained in culture for 2 weeks, fixed and stained with Geimsa. (FIG. 9A) Giemsa-stained plates. Knockdown has larger and higher number of colonies than control. (FIG. 9B) Quantification of CFU-F frequency. Higher frequency of CFU-F detected with knockdown. (FIG. 9C) Measurement of colony size. Knockdown has an increase in colony size.

FIGS. 10A-10D.

(FIG. 10A) GSTT1 overexpression analysis. Transfection of expression vector in fast growers (null) found GSTT1 level increasing by about 50 000 fold of control at 3 days post-transfection. (FIG. 10B) Viable cell count. 40% decrease in cell number in the overexpression system compared to control. (FIG. 10C) EdU labeling assay. Flow cytometric analysis following labeling show decline in the number of dividing cells with overexpression. (FIG. 10D) xCELLigence system run. Increase in growth rate with overexpression.

FIGS. 11A-11F.

Characterisation of BMMNCs isolated from donors A-F. (FIG. 11A) microscopy of BMMCs isolated from donors. (FIG. 11B) Bar chart showing CFU-F efficiency and colony size. (FIG. 11C) Left panel: bar chart showing proportions of 'small' cells. Right panel: scatterplot showing. (D) Graph and bar charts showing cell numbers through passages. (E, F) Graph and bar chart showing telomere length through passages (FIG. 11E) and $R^2$ value [correlation coefficient] (FIG. 11F).

FIG. 12.

Scatterplot showing surface phenotypic profiles of hMSCs. A panel of twenty-four CD markers were checked for their expression on hMSCs. Cells from all the donors satisfied the minimal criteria set by the ICST by demonstrating >95% expression for CD103, CD73, and CD90, and, <2% expression for haematopoietic markers. The dotted reference line corresponds to 2%. The cells showed variability in the expression of growth factor receptors and additional hMSC-related markers such as CD146, STRO-1, and SSEA-4.

FIG. 13.

Bar chart showing cytokines and growth factors produced by hMSCs from donors A-F.

FIG. 14.

Bar chart showing production of growth factors by hMSCs from donors A-F.

FIGS. 15A-15B.

Analysis of ability of MSC to inhibit T-cell proliferation (FIG. 15A) Bar chart showing dose-dependent suppression of T cell proliferation under antibody stimulation by hMSCs. (FIG. 15B) Table summarising the results. *P<0.05.

FIGS. 16A-16C.

Figure 16A:
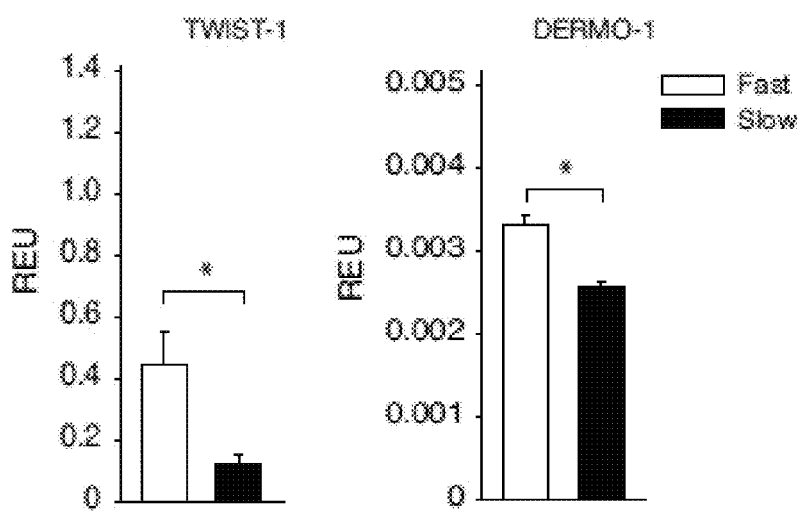

Gene expression by fast-growing and slow-growing hMSCs (FIG. 16A) Bar charts showing TWIST-1 and DERMO-1 expression by fast-growing and slow-growing hMSCs. (FIG. 16B) Representation of differentially expressed genes. (FIG. 16C) Plots showing expression of RUNX2, ALP, BSP-II, SOX9, COL2, CEBPα and PPARγ by fast-growing and slow-growing hMSCs isolated from donors A-F. *P<0.05

FIGS. 17A-17C.

Multilineage differentiation ability by fast-growing and slow-growing hMSCs isolated from donors A-F. (FIG. 17A) Plots showing expression of RUNX2, BSP-II, ALP, COL2A1, SOX9 CEBPα and PPARγ by fast-growing and slow-growing hMSCs isolated from donors A-F. (FIG. 17B) Images showing von Kossa, Alizarin red, Alician blue and Oil red O staining of cells isolated from donors A-F. (FIG. 17C) Plots showing quantification of stainings of (B). *P<0.05, **P<0.01.

FIGS. 18A-18E.

Figure 18A:
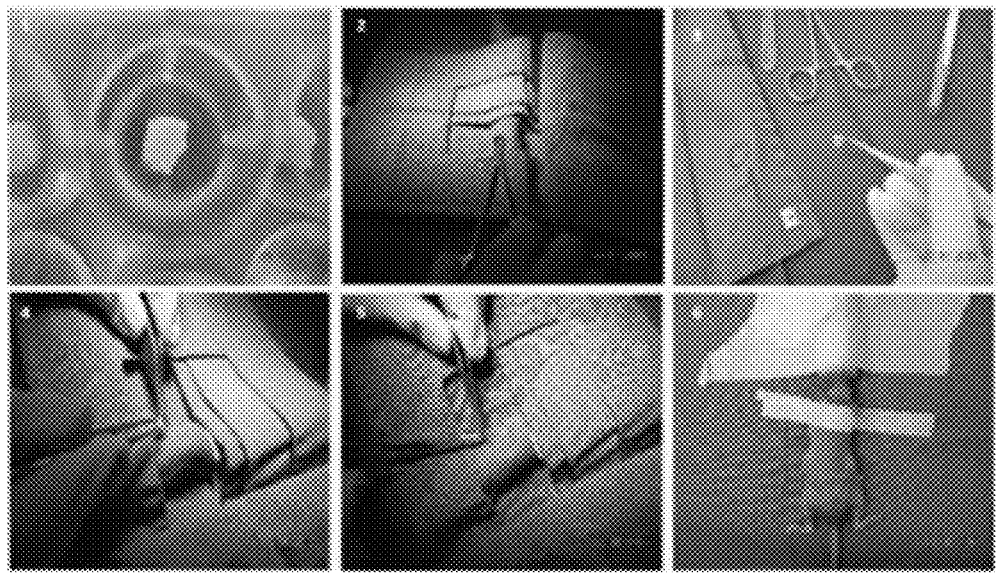
Figure 18A:
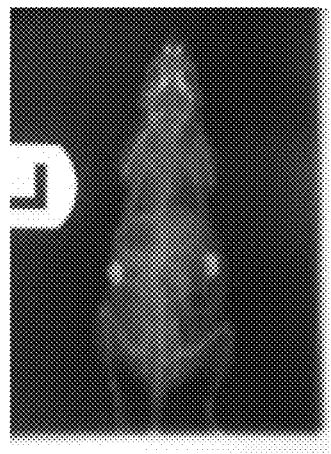
Figure 18B:
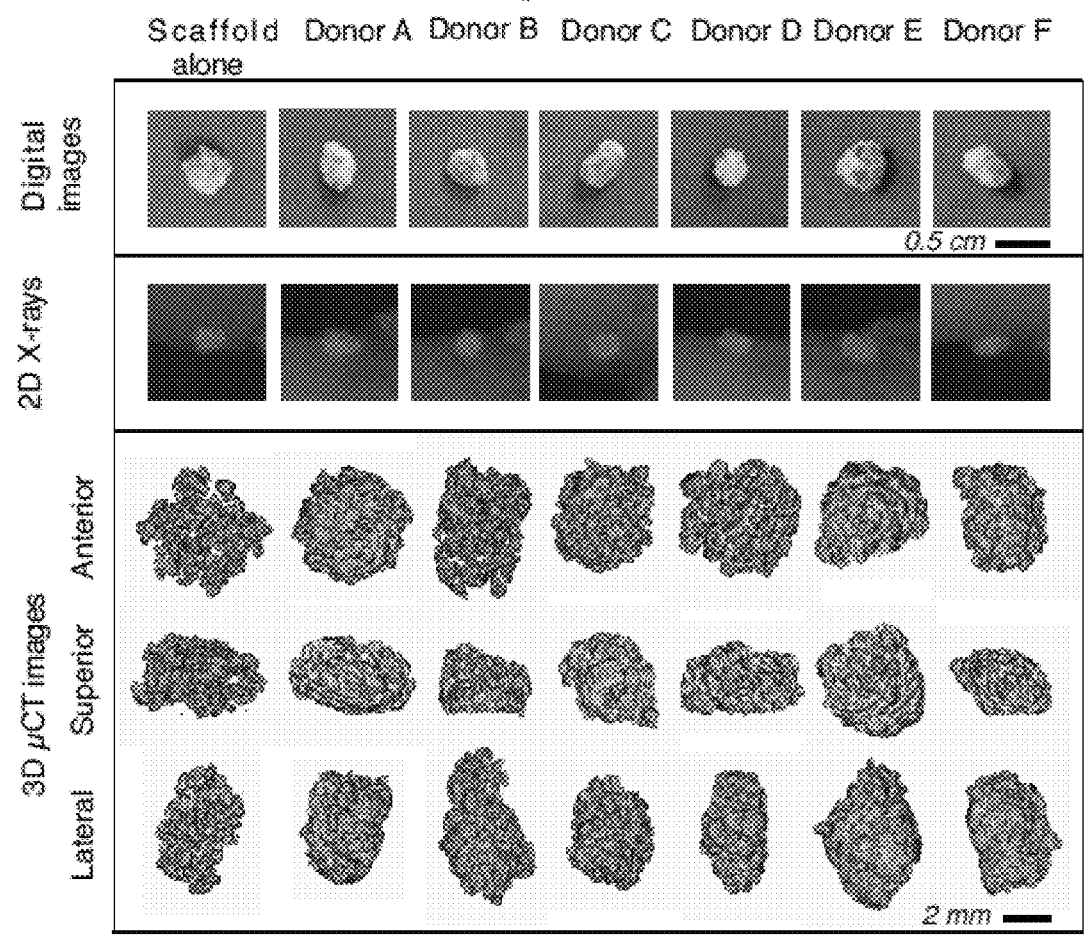
Figure 18C:
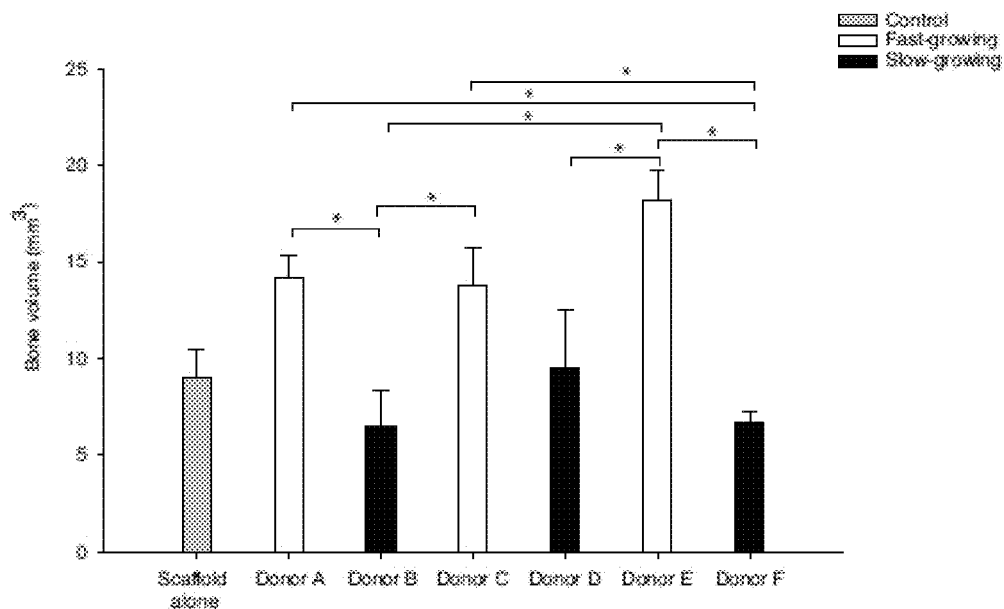
Figure 18D:
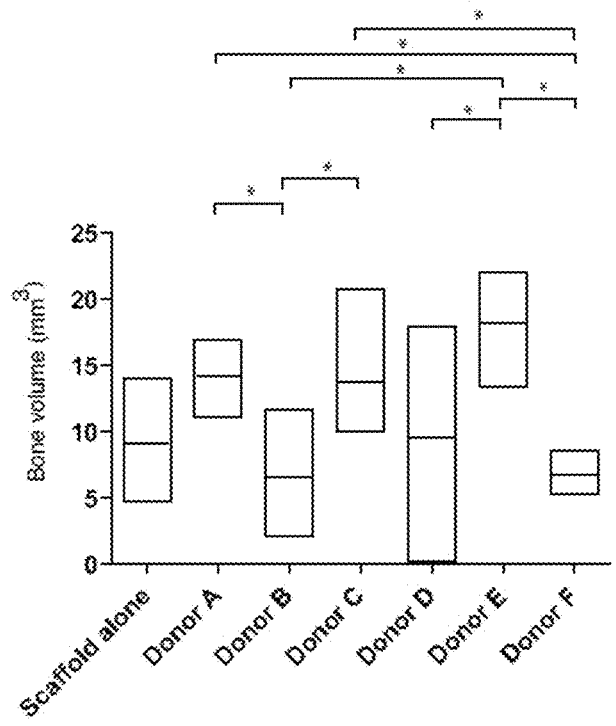
Figure 18E:
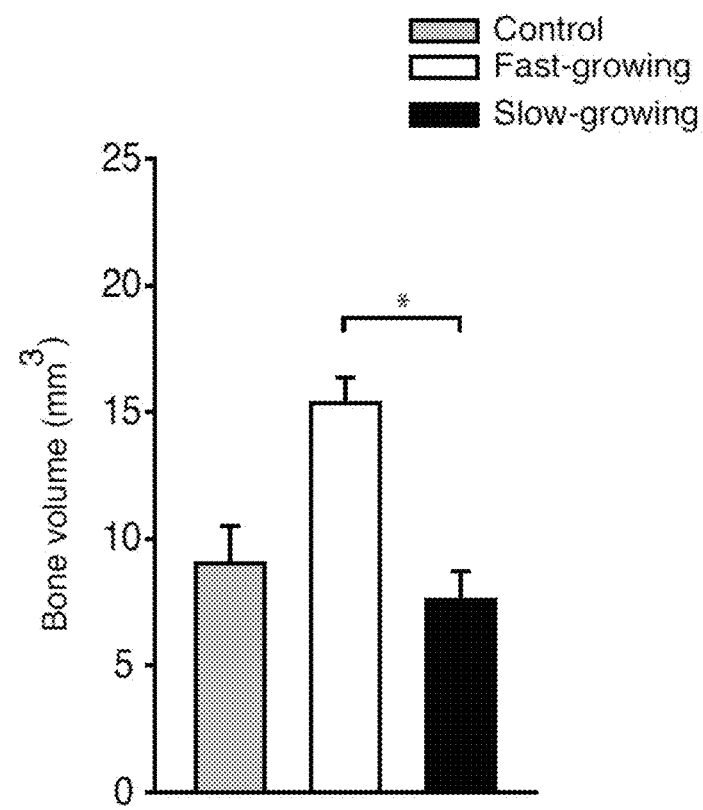

Ectopic bone formation by hMSC isolated from donors A-F in mice in vivo (FIG. 18A). (FIG. 18B) Images, x-rays and 3D μCT images of bone formed by hMSC isolated from donors A-F (FIG. 18C) Bar charts and (FIG. 18D) box plot showing bone volume formed by hMSC isolated from donors A-F; *P=0.002, ANOVA (post-test, Fisher LSD). (FIG. 18E) Bar chart showing bone volume formed by fast- and slow-growing hMSC; *P=<0.001 (t-test).

FIGS. 19A-19B.

Figure 19A:
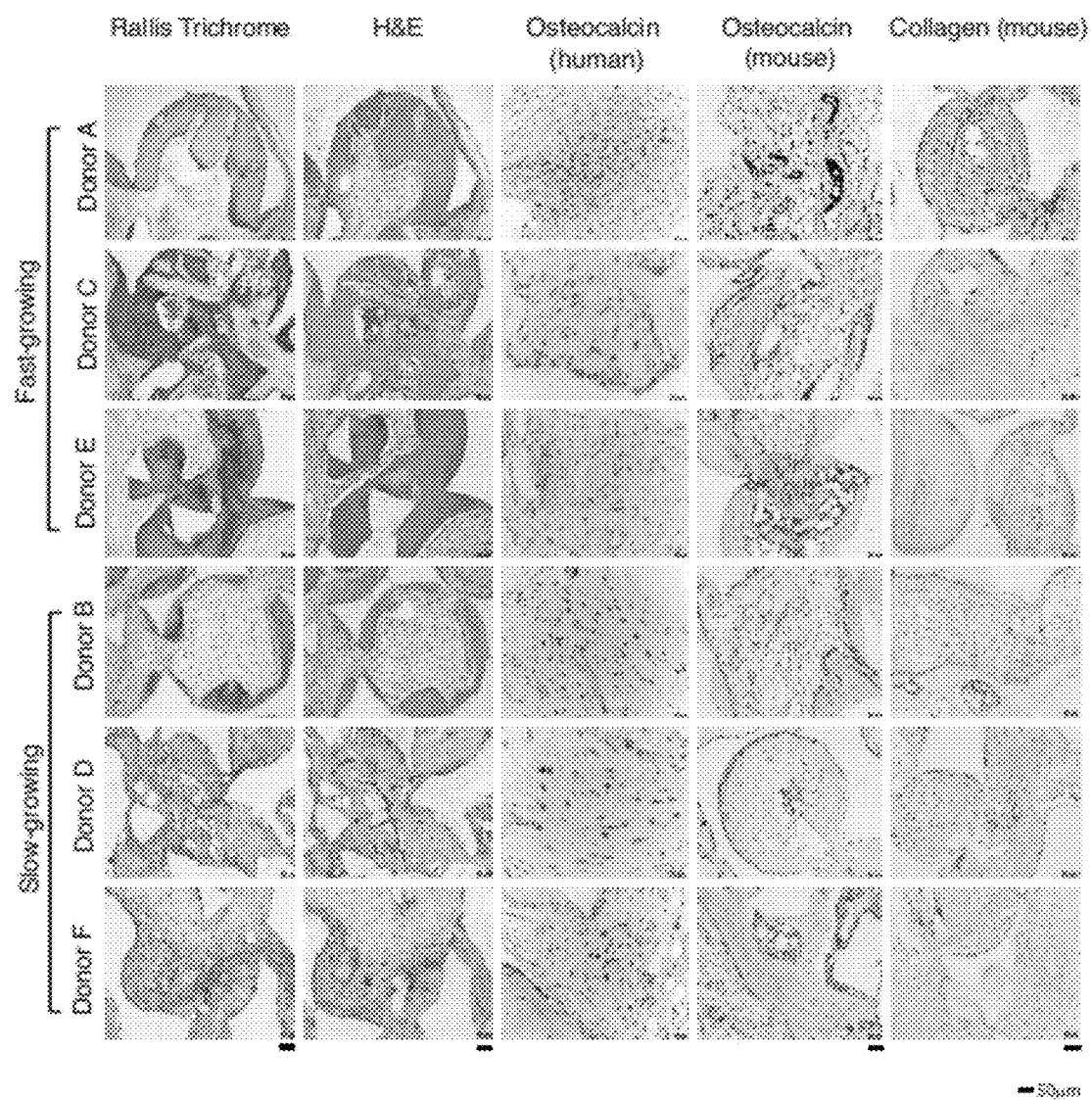

(FIG. 19A) Immunohistochemical analysis of sections harvested from in vivo implants of hMSC fast-growing and slow-growing hMSCs isolated from donors A-F. (FIG. 19B) Histological analysis. Representative images on a scale of least (left) to highest (right) bone formation. For each donor, first three panels=H&E staining, last three panels=Rallis trichrome staining. Lighter staining=fibrous tissue, darker staining=bone tissue.

FIG. 20.

Photographs showing colonies of hMSCs formed when plating bone marrow mononuclear cells from donors A-F.

FIG. 21.

Representative schematic of CFDA-SE assay. T cells and hMSCs from a representative fast-growing donor (donor A) or representative slow-growing donor (donor F) were co-cultured in varying proportions of T cell: MSC. The percentage of T cells proliferating can be derived from the CFSE-read out (read by the FITC channel) where peaks show successive cell divisions. The scatter plots (SSC vs FITC) indicate the percentage of cells positive for FITC. Differences in the size of the proliferating T cell colonies are visualized by the T cell micrographs of individual wells of a 96-well plate. Positive controls (no hMSCs) and negative control (no antibody) are also included.

FIG. 22.

Scanned images of 6-well plates showing differences between the staining intensity of induction (top wells) and control cultures (bottom wells) stained by the von Kossa method and with Alizarin Red to detect mineralization during osteogenesis, and Oil red O to detect lipid formation during adipogenesis. Sections of pellets stained with Alcian blue showing differences in glycosaminoglycan formation during chondrogenesis.

FIG. 23.

Schematic diagram showing the genomic location of GSTT1 and the deletion responsible for the null allele (reproduced from Teixeira et al., (2013) Tuberculosis—Current Issues in Diagnosis and Management; Chapter 6: Tuberculosis Pharmacogenetics: State of the Art). The null allele of GSTT1 results from a 50 kbp deletion that encompasses the entire gene on chromosome 22. The null genotype is common (20-58%) in human populations.

FIG. 24.

Schematic diagram of the assay for the detection of the deleted and wildtype GSTT1 alleles. In the presence of GSTT1, the GSTT1_Deletion primer set will not amplify a product since the distance between the forward and reverse primer is too long for amplification, and only the GSTT1_Gene primer set will generate a product. Amplification by the GSTT1_Deletion will only occur in the absence of the gene.

EXAMPLES

Example 1—GSTT1 is a Prognostic Biomarker of Function Mesenchymal Stem Cells for Bone Regeneration The gene encoding Glutathione-S-transferase isoform T1 (GSTT1) is commonly deleted in the human population. The present inventors have found that the GSTT1 genotype significantly affects the proliferation and bone-forming potential of BM-MSC derived from patients. In particular, the null allele of GSTT1 renders BM-MSC with greater proliferation in vitro and improved bone forming activity, relative to BM-MSC that retain a functional allele of GSTT1.

This finding is clinically applicable as it provides a means to pre-screen and select donors based on their genotype thus improving the efficacy of bone repair with BM-MSC transplantation.

1.1 Variation in Proliferation Rate Between Fast and Slow Growers

Bone marrow-derived mesenchymal stem cells (BM-MSC) from several donors have been were characterised according to proliferation rate either as 'fast-growers' or 'slow-growers'.

Genome-wide expression analysis by microarray was performed to find transcriptome-level differences between the two groups. The goal was to determine if there are inherent molecular variations, and also find genetic differences that contribute to the phenotypic differences. Gene ontology of the resulting data shows several biological processes linked to cell cycle to be upregulated in the fast growers, while differentiation/development associated processes were down compared to slow growers, which correlates with the phenotype.

Figures 1A, 1B:
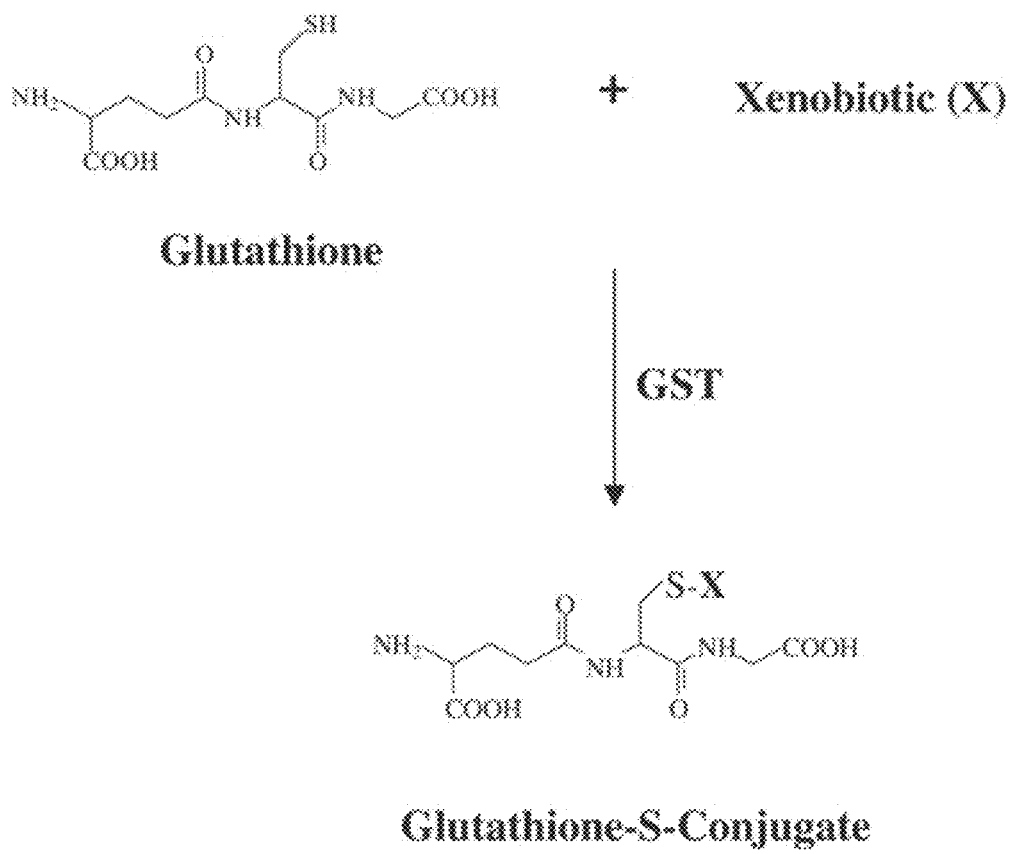
FIGS. 1A and 1B.
Figures 2, 3:
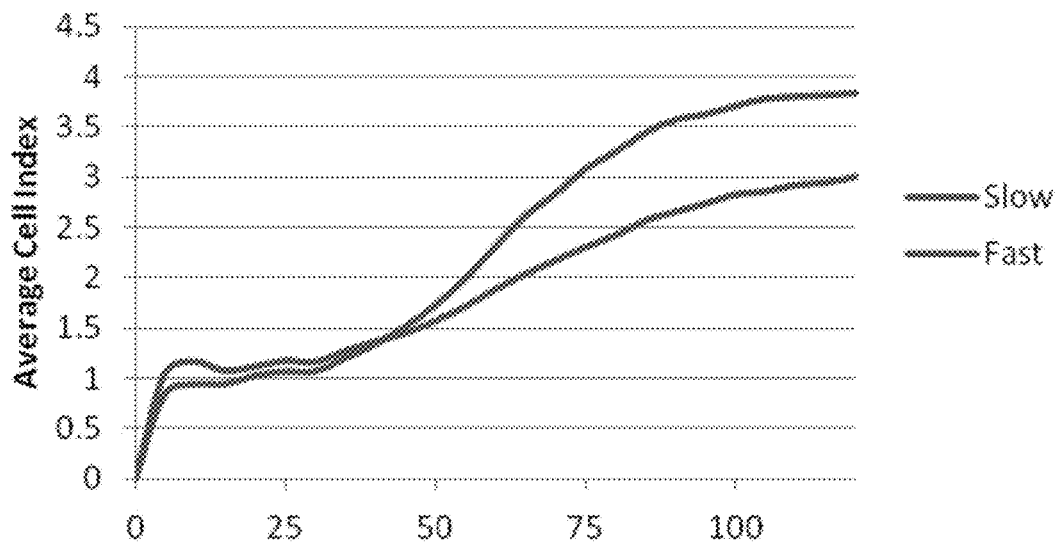
FIG. 2.

Assessment of proliferation rate on the xCELLigence system showed the variance in growth rate in real time between the fast and slow growers (FIG. 3). The cell doubling times of fast growers on average was 35 h, while it was more than double at 75 h for slow growers. This corroborates the difference in proliferation between the two groups observed by the other growth assays (Samsonraj et al., manuscript in preparation).

1.2 Slow Growers Express GSTT1 and Most Fast Growers Lack it

Characterization for proliferation and clonogenic potential for the donor derived lines found BM-MSC from donors A, C and E to be fast growers, while those from donor B, D, F and 10R and 11R were slow growers. Microarray analysis of the BM-MSC lines showed GSTT1 as the most differentially expressed gene between the two groups with the slow growers highly expressing the gene in comparison to fast growers (FIG. 4A).

Figures 4A, 4B:
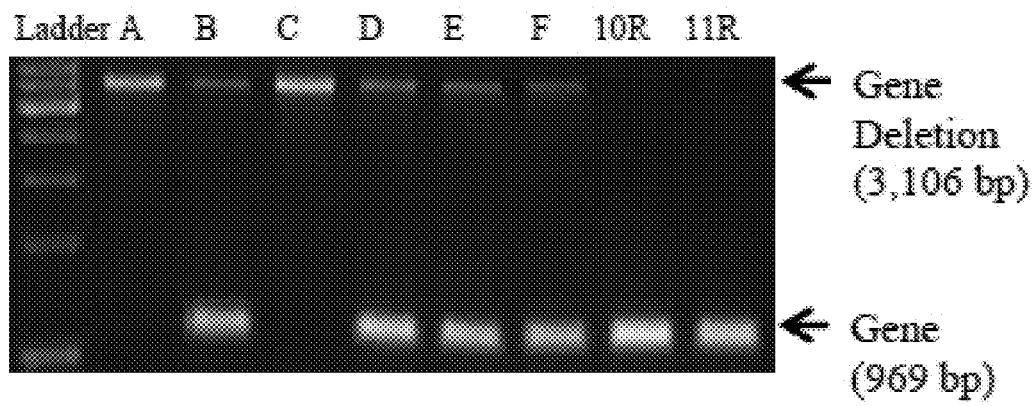
Figure 4C:
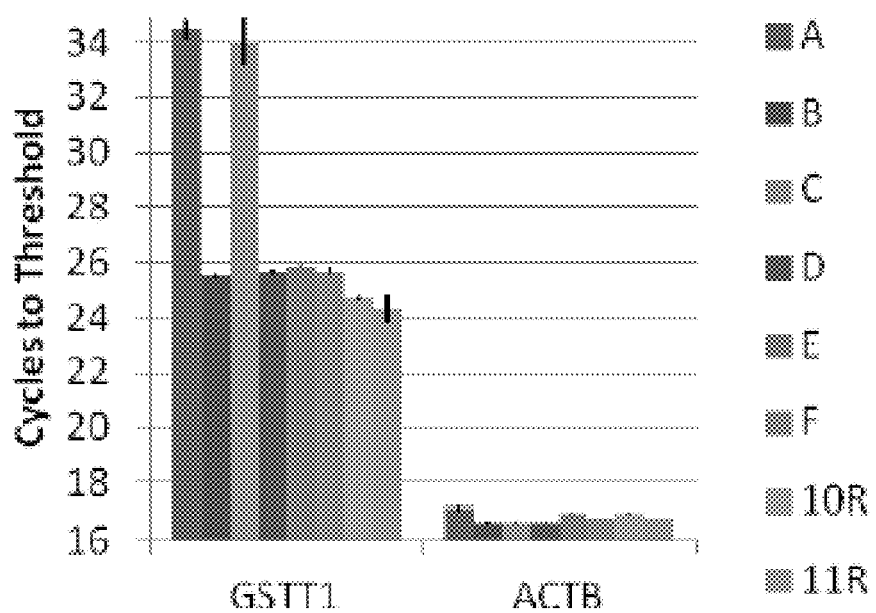
Figure 4D:
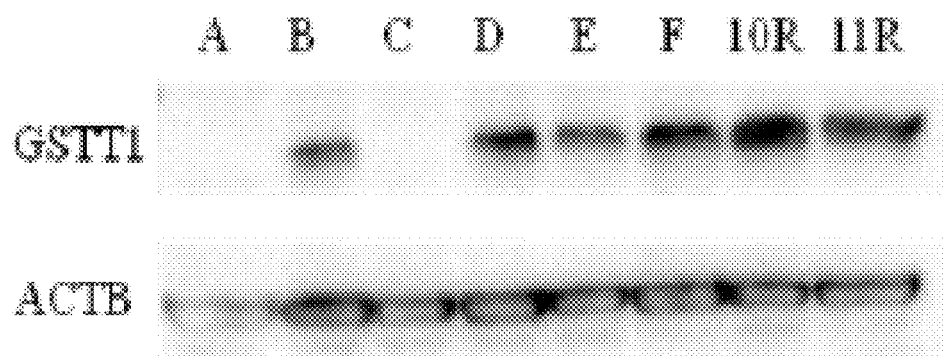

Genotyping for GSTT1 revealed two of the three fast growers (A and C) to have homozygous deletions of the gene, while the slow growers were positive, either as heterozygotes (B, D and F) or homozygous positives (10R and 11R) (FIG. 4B). RNA and protein expression analysis by qRT-PCR and western blot respectively showed the lack of expression of GSTT1 by the lines A and C, and expression by the other lines, consistent with the genotyping result (FIGS. 4C and 4D). The homozygote positives also had a higher expression of the gene than the heterozygotes, agreeing with the trimodal effect seen with copy number of alleles.

1.3 No DNA Damage Difference Between Fast and Slow Growers

Aberrations in DNA repair mechanism are often associated with accelerated proliferation due to faulty cell cycle checkpoints. This may lead to accumulation of DNA damage which can be studied through assays that detect DNA lesions such as comet assay (also known as single cell electrophoresis assay). The fast and slow growers were studied using this method to check their extent of DNA damage to ensure the proliferation difference was not due to the malfunctioning of the DNA damage surveillance mechanism. The comet tails were mostly undamaged for both groups, and the comet tails, if any, were very slight (FIG. 5A). Quantification of the comets also showed almost negligible level of DNA damage for the groups (FIG. 5B), confirming normal intact state of the DNA. The cell cycle control of DNA repair/damage seems in check for the fast growers.

1.4 Similar Oxidative Stress Response of Fast and Slow Growers

The GST superfamily of enzymes plays a major role in oxidative stress response since it removes reactive oxygen species (ROS) by glutathione conjugation. No convincing data is available for the effect of GSTT1 loss on oxidative stress response. To assess whether the GSTT1 genotype affects oxidative stress response, the fast and slow growers were treated with hydrogen peroxide, followed by hOGG1 (DNA glycosylase) treatment which cleaves at oxidized purines before being analyzed by comet assay. For both groups, the hydrogen peroxide and enzyme treated samples had significantly higher level of oxidized DNA damage than the untreated control (FIG. 6). Furthermore, the extent of DNA lesion was comparable between the groups, indicating no variation in the stress response despite the difference in genotype. So, the loss of GSTT1 does not affect the removal of oxidative factors, indicating that the presence of the other GST enzymes is sufficient to cope with the stress.

1.5 GSTT1 Expression Increases with Passage

Genes associated with cell cycle are commonly modulated with prolonged passaging, an effect believed to mimic aging. It is known that GSTT1 increases with aging, although it is unknown why this happens. MSC can be maintained in culture at optimal state up to passage 8, beyond which their proliferation slows down and they show signs of senescence. In order to investigate the effect of passaging on GSTT1, slow-growers were maintained in culture, and passaged when 70% confluent. At certain passages, cells were harvested for expression analysis by qRT-PCR and western blot. Both methods found the expression level of GSTT1 to increase with passage (FIG. 7), suggesting its role in cell cycle regulation. Similar expression is seen between p5 and p8, but beyond p10 the expression consistently increased. By p15, the mRNA level was 2.5 fold higher than that of early passages.

1.6 GSTT1 Knockdown Increases Proliferation and Clonogenic Potential

Figure 8A:
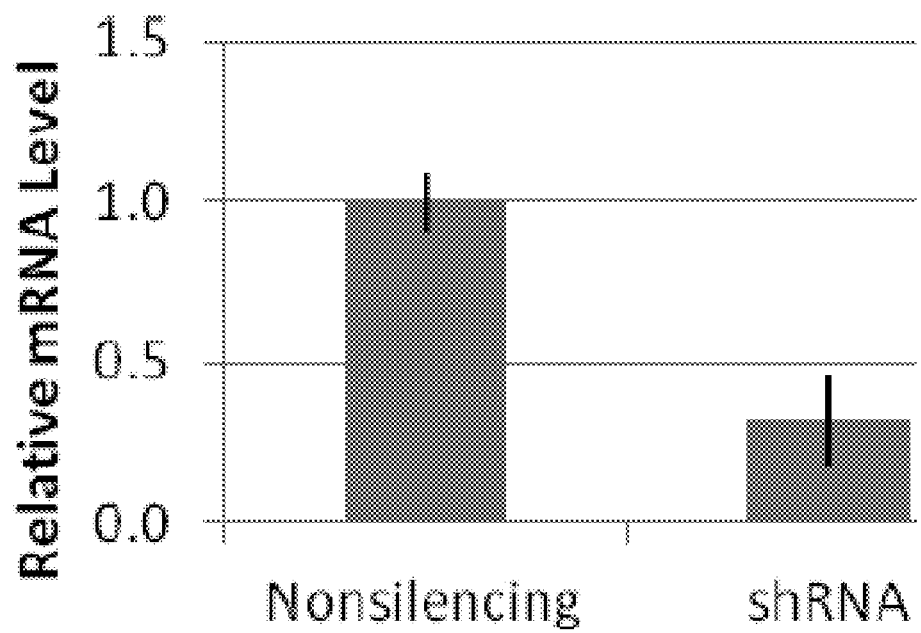

In order to assess whether it is the GSTT1 genotype that contributes to the enhanced proliferation observed with the fast growers (GSTT1 null) relative to slow-growers (GSTT1 positive), GSTT1 stable knockdown was performed and proliferative potential was studied. GSTT1 expression was suppressed up to 0.30 (SD±0.14) fold of that of nonsilencing control (FIG. 8A).

Figure 8B:
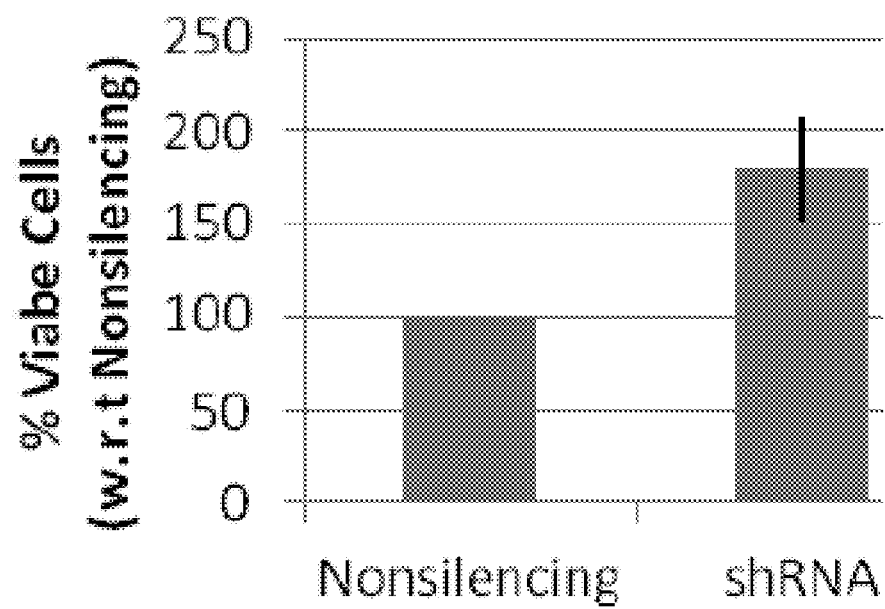
Figure 8C:
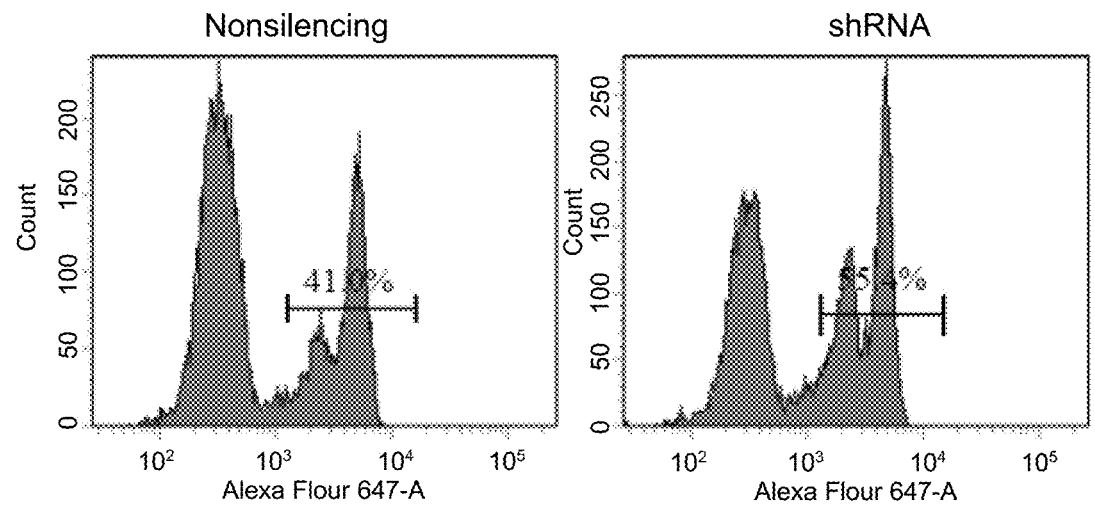
Figure 8D:
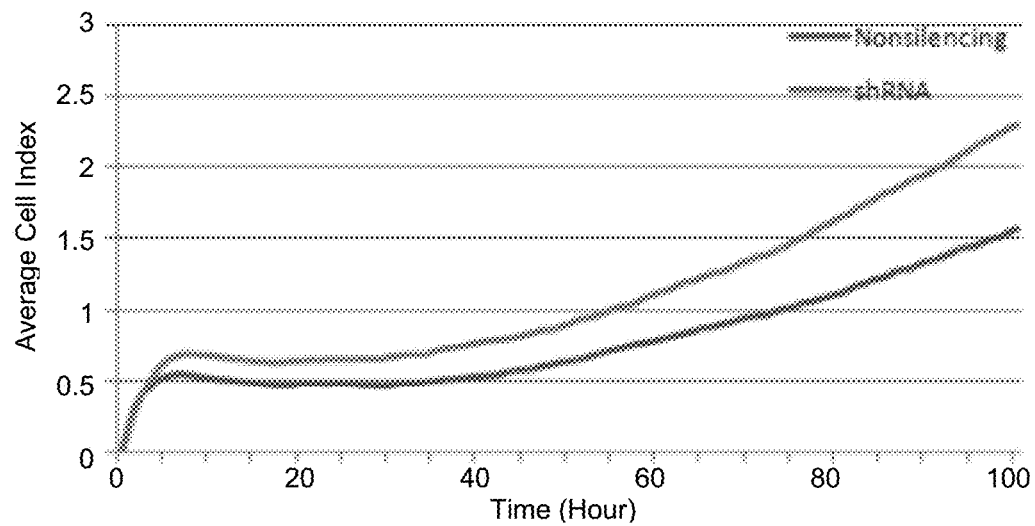

For both treatments, cells seeded at the same density were stained with trypan blue and quantified at 5 days post-seeding. The viable cell count was significantly higher for the knockdown by approximately 80% (SD±28.28%) with respect to nonsilencing (FIG. 8B). The percentage of dividing cells in the span of 24 h was also higher as measured by the incorporation of 5-ethynyl-2'-deoxyuridine (EdU) (FIG. 8C). Real-time monitoring of proliferation by the xCELLigence system also confirmed the accelerated proliferation of the knockdown. The proliferate rate of the knockdown is about 34 h, which is close to 10 h difference of the doubling time of the nonsilencing at 43 h (FIG. 8D). Overall, the proliferation assays show an increase of growth rate with a decline in GSTT1. Infection of GSTT1 null BM-MSC line with the lentivirus packaged with shRNA did not affect their proliferation as assessed by the various techniques (data not shown), indicating specificity of the shRNA for GSTT1.

Clonogenic potential was also measured to determine whether the self-renewal of the BM-MSC is affected by the knockdown of GSTT1 expression. The clonogenic potential of MSC is defined by colony-forming-units-fibroblasts (CFU-F). The knockdown and nonsilencing control were plated a low density and maintained for 2 weeks before they were fixed and counterstained by Giemsa.

Figure 9A:
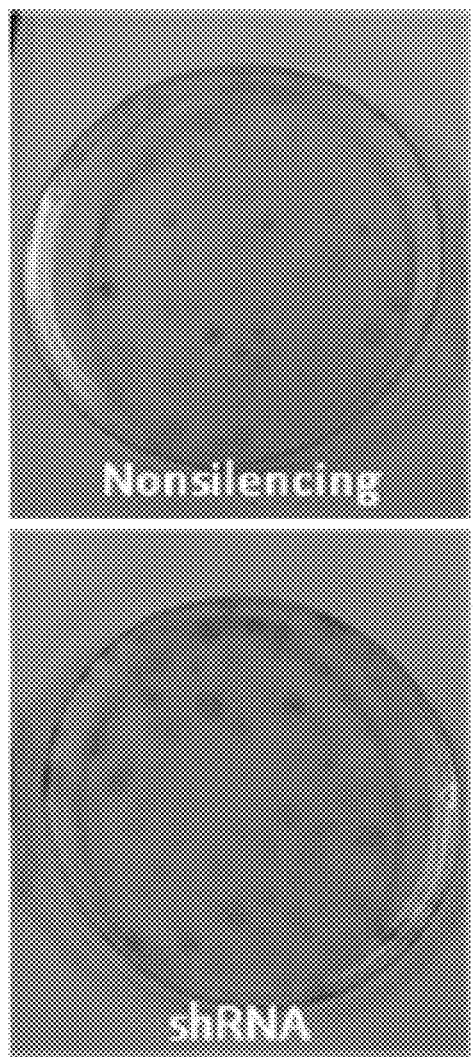
Figure 9B:
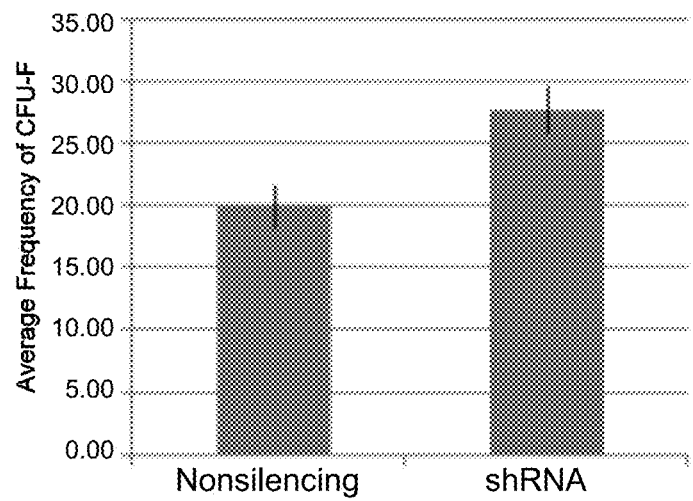
Figure 9C:
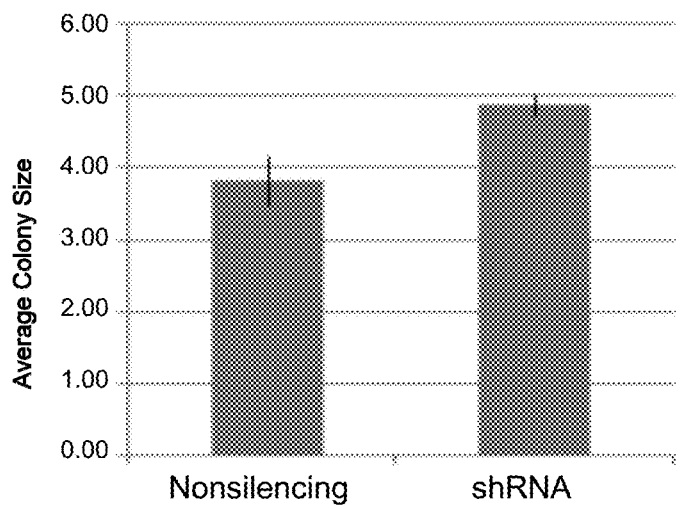

Visual inspection showed a larger number of colonies formed by the knockdown which were also bigger than the control (FIG. 9A). Quantification of the results found an average of 7% increase in the frequency of CFU-F (FIG. 9B) and an increase in the colony size by approximately 1 mm (FIG. 9C). The data shows an improved clonogenic potential with lower GSTT1 expression, indicating its influence on self-renewal property of BM-MSC.

1.7 Overexpression of GSTT1 Decreases Proliferation

Figure 10A:
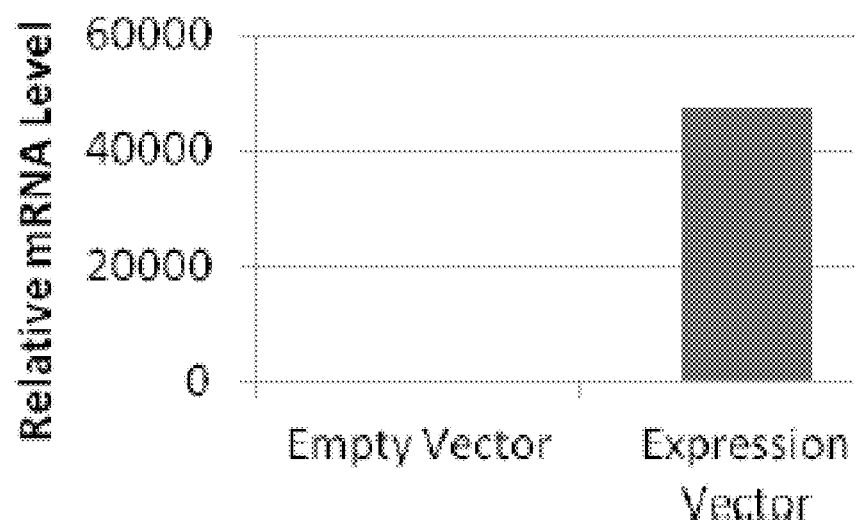

GSTT1 expression seems to be inversely correlated to proliferation in BM-MSC. To investigate if the overexpression of the gene will lead will have the opposite effect as the knockdown, the gene was transiently overexpressed in the fast growers that are GSTT1 null. Within 3 days of transfection, the expression level was close to 50 000 fold compared to the empty vector transfected cells (FIG. 10A). The proliferation assessments were performed between 1 to 2 weeks post-transfection.

Figure 10B:
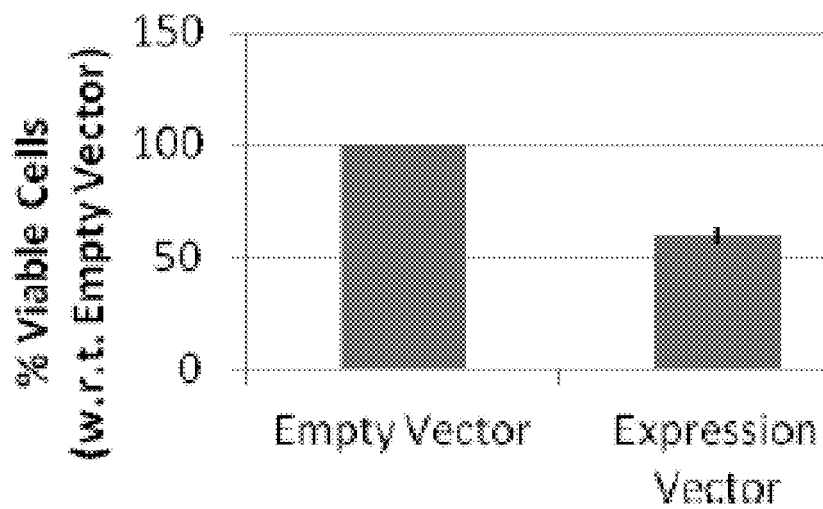
Figure 10C:
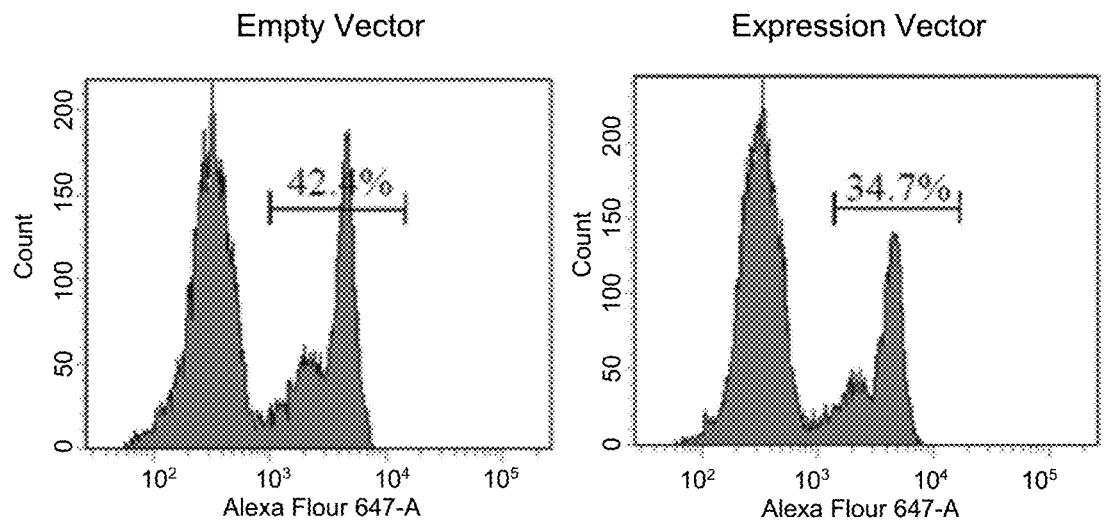
Figure 10D:
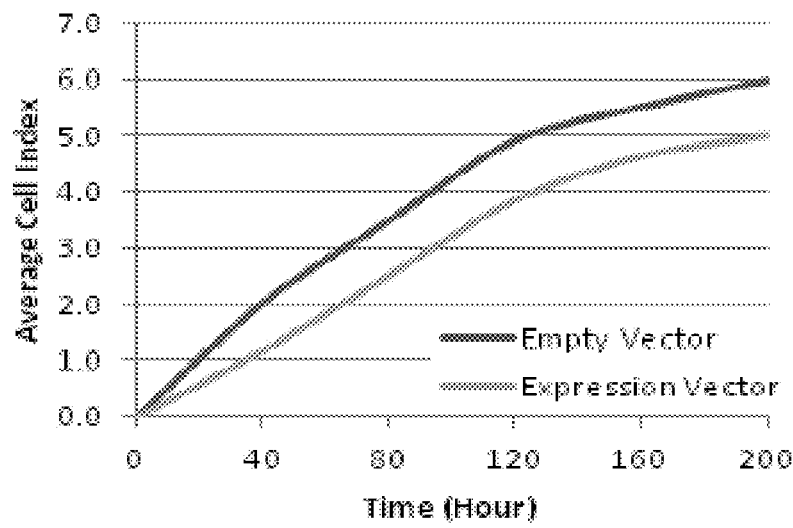

Viable cell count using trypan blue at day 5 post-seeding at a certain density showed the population of overexpression transgenic cells had a reduced percentage of cells at 60% (SD±3.79) with respect to the empty vector transfected cells (FIG. 10B). EdU labeling of dividing cells over the period of 24 h also found a decline in the proportion of mitotic cells by about 8% (FIG. 10C). Real-time measurement of growth rate was consistent with the other proliferation assays. The overexpression cell lines had a longer doubling time of 63 h, in comparison to the 53 h of the control. Overall, the overexpression of GSTT1 slowed the growth of the cells. The data confirms the involvement of GSTT1 in cell proliferation, with inverse relation to proliferation.

1.8 Conclusions

Microarray data on slow-growing and fast-growing BM-MSC identify GSTT1 is most differentially expressed between the two groups. The slow-growers expressed GSTT1, while the fast-growers had negligible expression. Genotyping for GSTT1 confirmed the slow-growers possessed a functional alelle and the fast-growers were null for GSTT1.

The fast-growers (GSTT1 null) generated more bone mass in our ectopic animal study. Thus, we show that the GSTT1 genotype predicts bone formation from BM-MSC isolated from patients.

The finding that GSTT1 genotype influences proliferation and differentiation of BM-MSC is in agreement with previous studies showing that oxidative stress induces an increase in GSTT1 expression possibly through the p38 signaling pathway, suggesting its involvement in cell cycle control. The expression studies prove association of GSTT1 with proliferation, and also show that the loss of GSTT1 does not affect oxidative stress response, which is important for the normal physiology of the cell.

Example 2—Correlation of hMSC Behaviour In Vitro with Efficacy In Vivo 2.1 Introduction The present inventors establish a set of benchmarks for the selection of hMSCs with high efficacy. The confirm that in vitro differentiation potential is not of itself a reliable indicator of stem cell potency, and sought to reassess the minimum criteria to better define an hMSC, and to directly benchmark them to in vivo efficacy. They found that, in addition to the markers defined by the ISCT (2006), Stro-1, CD146, CD140b best correlated with the ability to form bone in vivo. It was also found that cells expressing these extra markers also displayed faster population doubling times, a smaller cell phenotype, and a secretome comparatively rich in FGF2, VEGF165 and PDGF-BB. The present inventors thereby identify a combination which constitutes a stem cell signature that is highly predictive of successful in vivo outcomes.

2.2 Isolation and Culture of Human Bone Marrow-Derived Mesenchymal Stem Cells

Human MSCs (Lonza, Walkersville, MD) were isolated from bone marrow mononuclear cells (BMMNCs) (Table 1) by plating down the mononuclear cell fractions in maintenance media comprising of Dulbecco's Modified Eagles medium (DMEM-low glucose, 1000 mg/l) supplemented with 10% fetal calf serum (FCS; Hyclone), 2 mM L-glutamine, 50 U/ml penicillin, and 50 U/ml streptomycin (Sigma-Aldrich), as described previously (Rider et al, 2008). Cells from passage 4 were used for all experiments unless otherwise stated. Cells from individual donors were characterized and treated as a separate hMSC population throughout. For the CFU-F assays, BMMNCs were plated at 0.5-3.0×10$^6$ cells/T75 flask, allowed to adhere and form colonies, and stained with 0.5% crystal violet (Sigma-Aldrich, USA) after 14 days. Visible colonies were then enumerated only when they were greater than or equal to 50 cells in number and were not in contact with another colony.

TABLE 1

| Donor information | | | | |
|---|---|---|---|---|
| Donor ID | Sex | Age | Race | Source |
| Donor A | Male | 21 | Hispanic | Lonza, Walkersville Inc., MD |
| Donor B | Male | 20 | Caucasian | Lonza, Walkersville Inc., MD |
| Donor C | Male | 20 | Hispanic | Lonza, Walkersville Inc., MD |
| Donor D | Male | 26 | Caucasian | Lonza, Walkersville Inc., MD |
| Donor E | Male | 20 | Black | Lonza, Walkersville Inc., MD |
| Donor F | Male | 23 | Caucasian | Lonza, Walkersville Inc., MD |

2.3 Donor Variability in Colony Formation, Cell-Size, Growth and Telomere Lengths 2.3.1 Cell-Size Analysis Single cell suspensions of hMSCs were stained with Annexin V, washed and resuspended in MACS buffer (2 mM EDTA, 0.5% BSA in PBS, pH 7.2) before analysis with a FACSArray™ Bioanalyzer. After gating out the Annexin V– cells, a quadrant gate was applied to the live population and the fraction of very low FSC/SSC events estimated to obtain the relative percentage of small-sized cells.

Figure 11A:
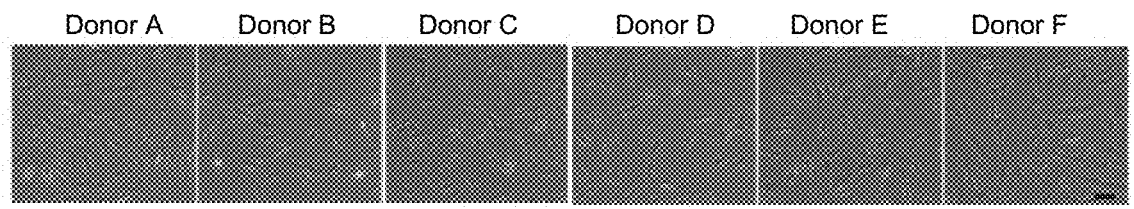
Figure 11B:
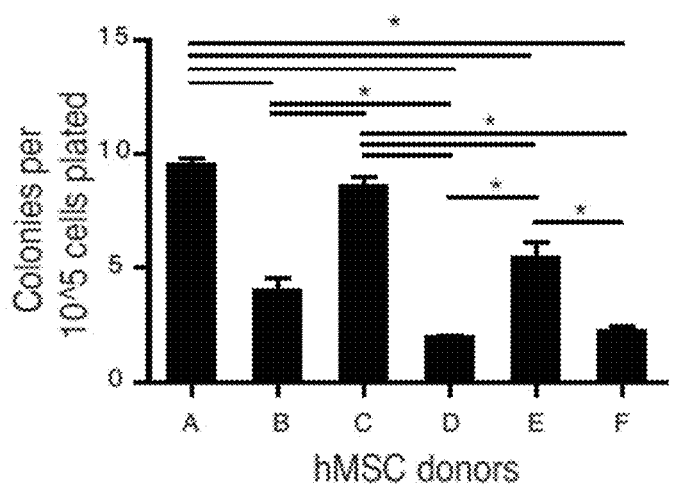

All donor BMMNCs adhered quickly to tissue culture plastic and gave rise to colonies that readily expanded in culture (FIG. 11A). Comparison between the donors revealed significant differences in CFU-F efficiency and size of the colonies. Donors A, C, and E showed relatively higher colony formation efficiency (7.4±1.7) than donors B, D, and F (3.2±1.1) (FIG. 11B). No differences in morphology were observed at earlier passage numbers (FIG. 11A), although at later passages, hMSCs from donors with high CFU-F efficiency showed smaller, compact, spindle shaped morphology, whereas hMSCs from donors with low CFU-F efficiency appeared larger, and more elongated (data not shown). All donors, by virtue of plastic-adherence and colony formation, thus satisfied the ISCT criteria for identification as mesenchymal stem cells.

Figure 11C:
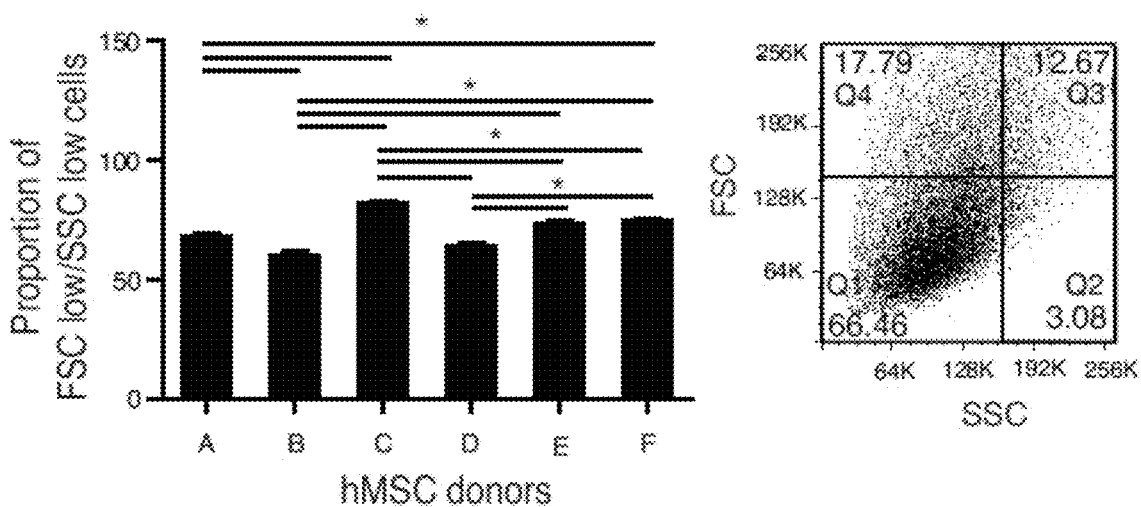

Cell size was analysed. In addition to the abundant spindle-shaped and large flattened cells, the heterogeneous populations also contained small, round cells that could be identified as rapidly self-renewing (RS) (Colter et al., 2001 Proceedings of the National Academy of Sciences of the United States of America 98:7841-7845; Sekiya et al., 2002 Stem Cells 20:530-541; Smith et al., 2004 Stem Cells 22:823-831), characterizable by flow cytometry as low forward scatter ($FSC^{lo}$) and low side scatter ($SSC^{lo}$) of light. Donors A, C, E, which the higher colony-forming ability, consisted of, on average, 74.4% smaller-sized cells (identified as $FSC^{lo}/SSC^{lo}$ in quadrant 1, FIG. 11C), whereas donors B, D, F, with lower colony-forming ability, consisted of only 66.4% small cells. Thus there was a positive correlation between CFU-F efficiency and the proportion of smaller cells present (FIG. 11B, 11C).

2.3.2 Cumulative Growth and Telomere Length Analysis

To compare hMSC growth between donors, cells were seeded at 5,000 cells/cm$^2$ and cultured under maintenance conditions. At 70-80% confluency, cells were enzymatically removed by 0.125% trypsin/Versene and viable cells counted using the Guava ViaCount® Assay with Guava EasyCyte™ Plus Sytem/CytoSoft™ software (Millipore™) Cells were re-plated at the same density and progressively sub-cultured to estimate cumulative cell numbers and population doublings over 13-15 passages or until senescence. Genomic DNA at different passages was isolated and telomere length analysis performed. Using human embryonic stem cells (hES3, ES International, Singapore) as the reference, telomere lengths of hMSCs were determined relative to the reference cell line and expressed in units of relative telomere lengths (RTLs) as described previously (Samsonraj et al., 2013 Gene). The hMSC sample DNA (12 ng/reaction) and reference DNA (across the various dilutions) were used as templates in SYBR Green-based real time PCR set-up with specific telomere (Tel) and 36B4 (single copy gene) primers.

Figure 11D:
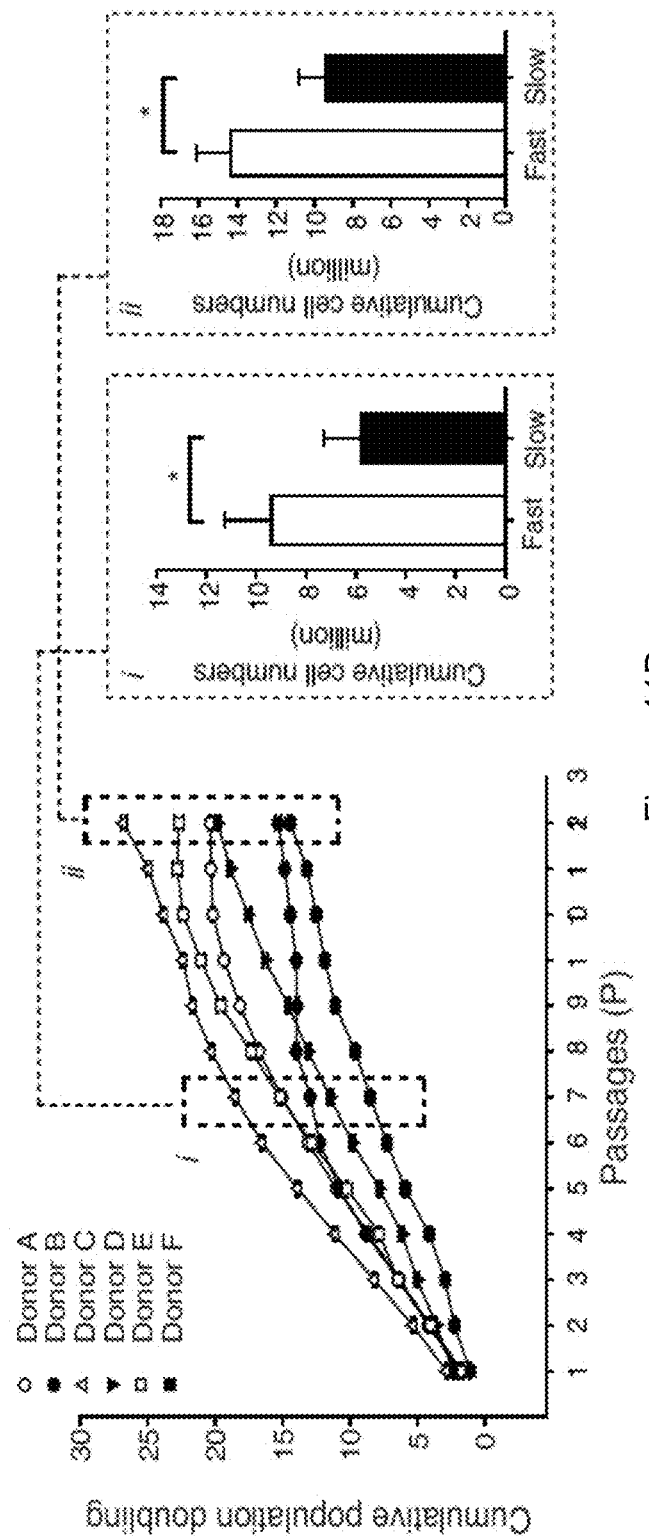
Figure 11E:
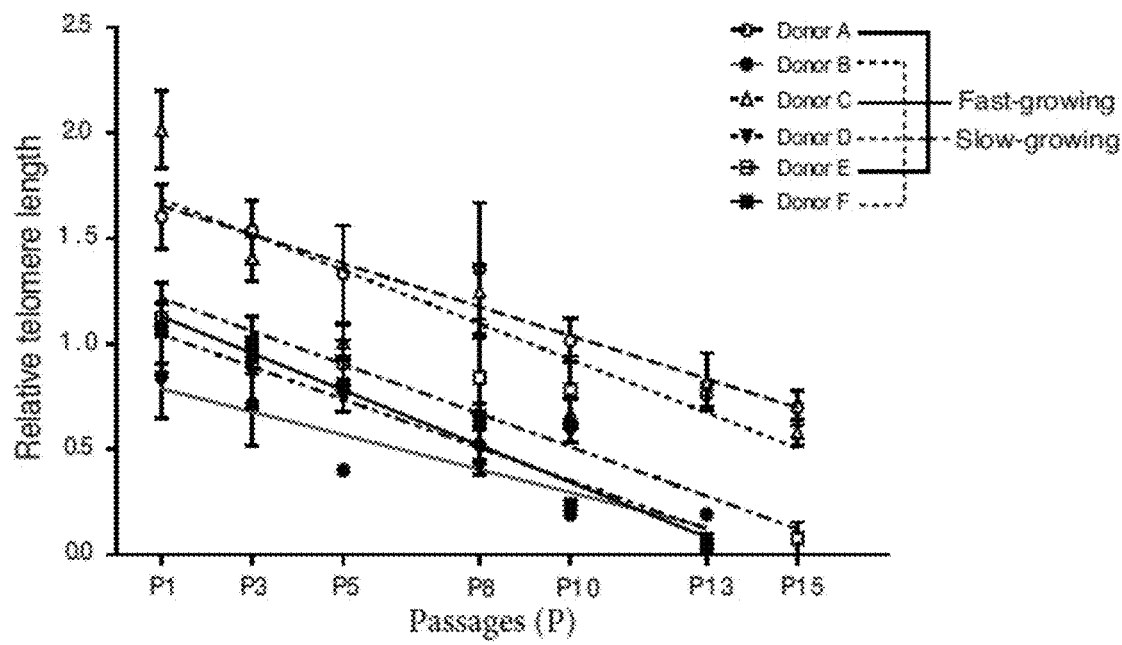
Figure 11F:
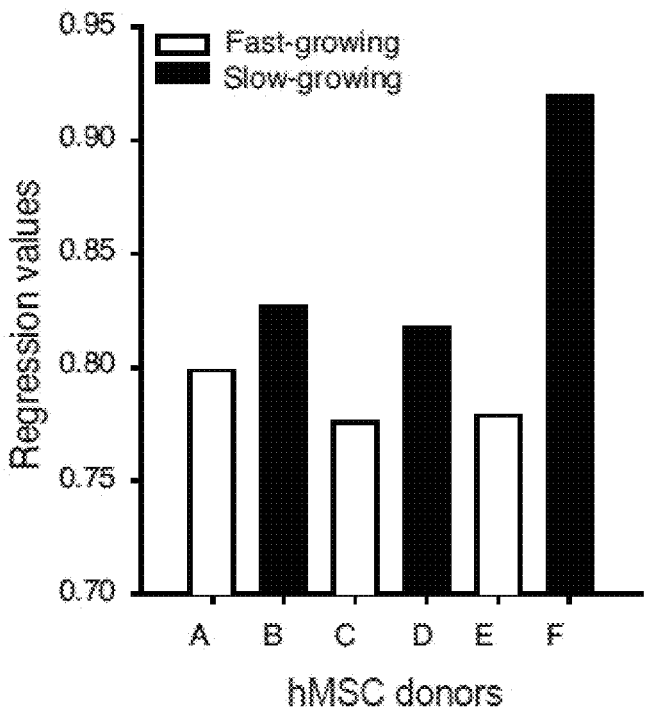
Figure 20:
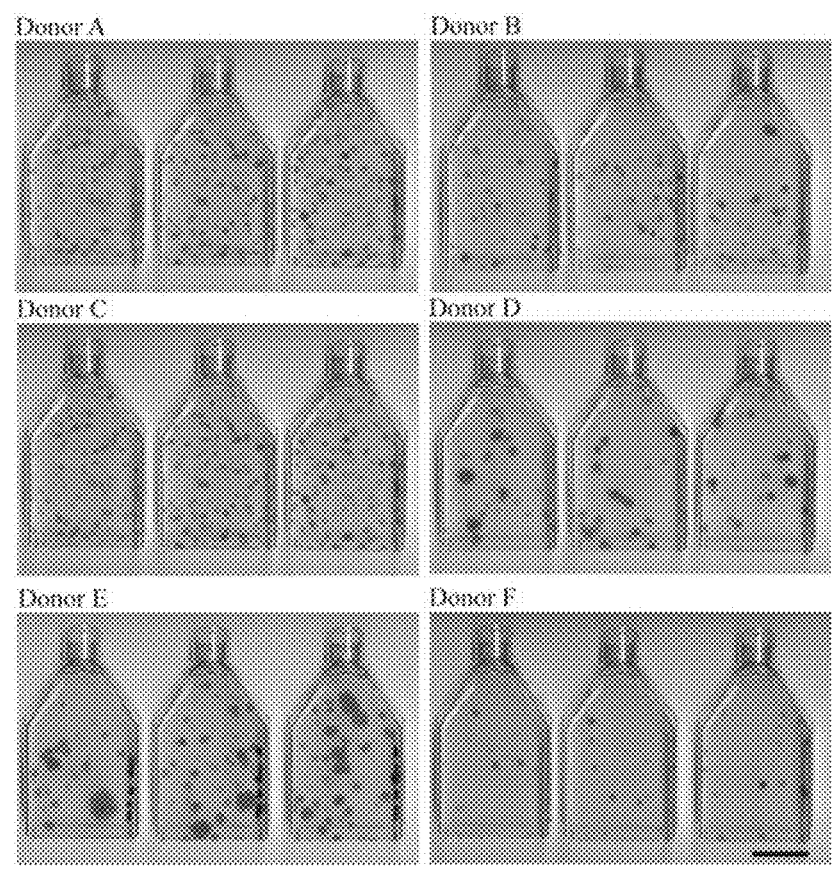

Growth is a key metric of MSC quality because the ability to self-renew is a defining trait. MSCs are known to undergo phenotypic changes with long-term expansion, eventually losing proliferative capacity. Cell growth was monitored for extended periods (8-10 weeks) in culture. Cumulative cell numbers and the extent of population doubling assayed over several passages revealed significant differences in proliferative potential. Donor C displayed the maximum growth, with donor F showing the minimum (FIG. 11D). On average, cells from (fast-growing) donors A, C, and E achieved 33% more cumulative cell numbers than (slow-growing) donors B, D, and F (P<0.05). These donors also showed a greater efficiency for colony formation (FIG. 11B) with higher percentages of smaller cells (FIG. 11C), signifying a correlation between cell growth, colony formation, and size. Taken together these results allowed us to group donors A, C, and E as fast-growing hMSCs and B, D, and F as slow-growing hMSCs. Real-time assessment of proliferation rates demonstrated that fast-growing cells have shorter population doubling times (~35 h) than slow-growing cells (~75 h), so confirming the growth differences between the two groups as observed in long-term expansion (FIG. 20).

As telomeres are tightly linked to cell divisions, the telomere status of these cells was checked. Analysis from initial seeding (P1) until senescence (P13-P15) at seven different passages showed progressive decreases in the relative lengths as the cells underwent divisions. The rate of telomere shortening occurred in a linear fashion, as indicated by the negative slope of the curves (FIG. 11E), albeit at different rates, as shown by the straight line gradients and the $R^2$ value (correlation coefficient) (FIG. 11F). Regression plots of donors A, C, and E showed substantially lower regression ($R^2$) values than donors B, D, and F suggesting that fast-growing hMSCs reduced their telomeres at rates less than that of slow-growing hMSCs (FIG. 11F). In addition, slow-growing hMSCs reached senescence after 13 passages whereas the fast-growing hMSCs underwent cell divisions until 15 passages.

Given that the age of the donors (between 20-30Y) was within a narrow limit, taken together our results confirm that donors whose cells gave rise to more colonies possessed higher proportions of small-sized cells with increased growth rates and relatively longer telomeres.

2.4 Immunophenotypic Characterization by Flow Cytometry

Flow cytometry was performed to compare surface immunophenotypic profiles of hMSCs. Single-cell suspensions were stained with phycoerythrin (PE)- or fluorescein isothiocyanate (FITC)-conjugated anti-human CD105, CD73, CD90, CD45, CD34, CD49a, CD29, EGF-R, IGF-IRα (CD221), NGF-R (CD271), PDGF-Rα and β (CD140a and CD140b), CD11b, HLA-DR, CD19, CD14, CD106, CD146, SSEA-4, STRO-1 antibodies or isotype-matched controls IgG1, IgG1κ, IgG2a κ, IgG2b κ, IgM(p) and IgG3, and analyzed on BD FACSArray™ Bioanalyzer and FlowJo software. All antibodies were purchased from BD Biosciences except IgM (μ) (Caltag laboratories) and STRO-1 (kindly provided by Prof Stan Gronthos, Institute of Medical and Veterinary Sciences, University of Adelaide, Australia).

2.4.1 Immunophenotypic Profiles of hMSCs

Figure 12:
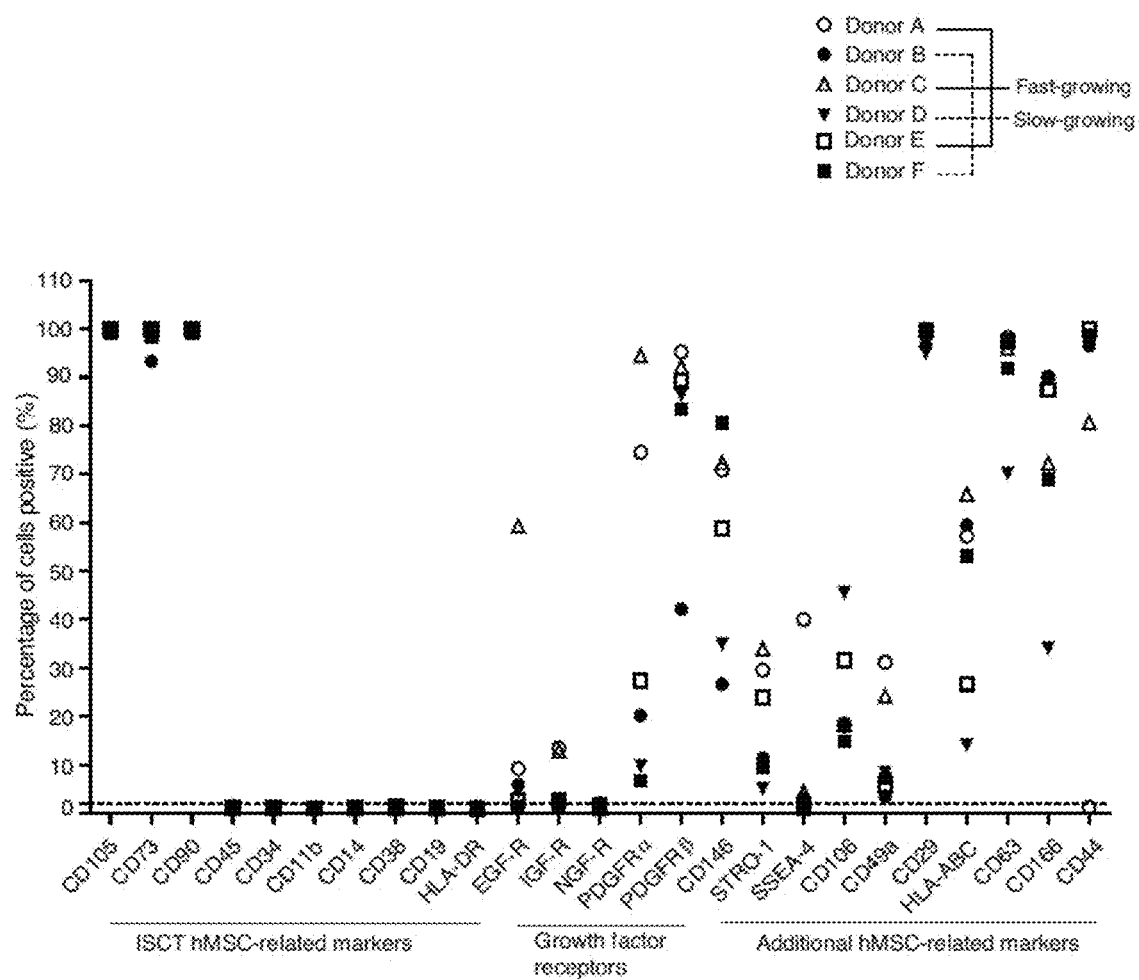

The next step was to verify the presence of CD markers. A set of 27 markers including those described by the ISCT as definitive for MSCs was analysed (Dominici et al., 2006 Cytotherapy 8: 315-317). Culture-expanded hMSCs from all the donors were uniformly and strongly positive for CD105, CD73, and CD90 (greater than 95%) and negative for the hematopoietic markers CD45, CD34, CD11b, CD14, CD38, CD19, CD31 and HLA-DR (FIG. 12). Donor variability was seen in the expression of markers that have been recently proposed to identify MSCs. Growth factor receptors such as EGFR, IGFR, PDGFRα/β had variable expression as evident by the spread of data in the profile. Other recently described markers such cell adhesion molecules CD106, CD146, CD166 were also differentially expressed, although with little correlation with growth. PDGFRα levels, which correlate with osteogenic potential (Tokunaga et al., JBMR 2008), were higher in slow-growing hMSCs. Notably, fast-growing hMSCs had significantly higher expression of STRO-1, SSEA-4, CD146, and PDGFRβ P<0.05, t-test). From our profiling, it is evident that the ISCT criteria is inadequate and MSC identification should include checking the levels of STRO-1, SSEA-4, CD146, and PDGFRβ

2.5 Quantitative Multiplex Detection of Cytokines

Media conditioned by cells seeded at 3,000 cells/cm$^2$ in maintenance media were collected after 4 days. To release matrix bound proteins, cell layers were treated with 2M NaCl in 20 mM HEPES (pH 7.4) for 5-10 sec. Conditioned media and salt wash were analyzed separately using Millipore's MILLIPLEX® MAP—Human Cytokine/Chemokine kit (Cat. No. MPXHCYTO-60K) for simultaneous quantification of fourteen different growth factors, according to the manufacturer's instructions. Results are presented as concentrations of total growth factors, in picograms/ml normalized to cell numbers, which included factors secreted into media and factors that were matrix-bound.

2.5.1 Cytokine Secretion Profiles of hMSCs

Figure 13:
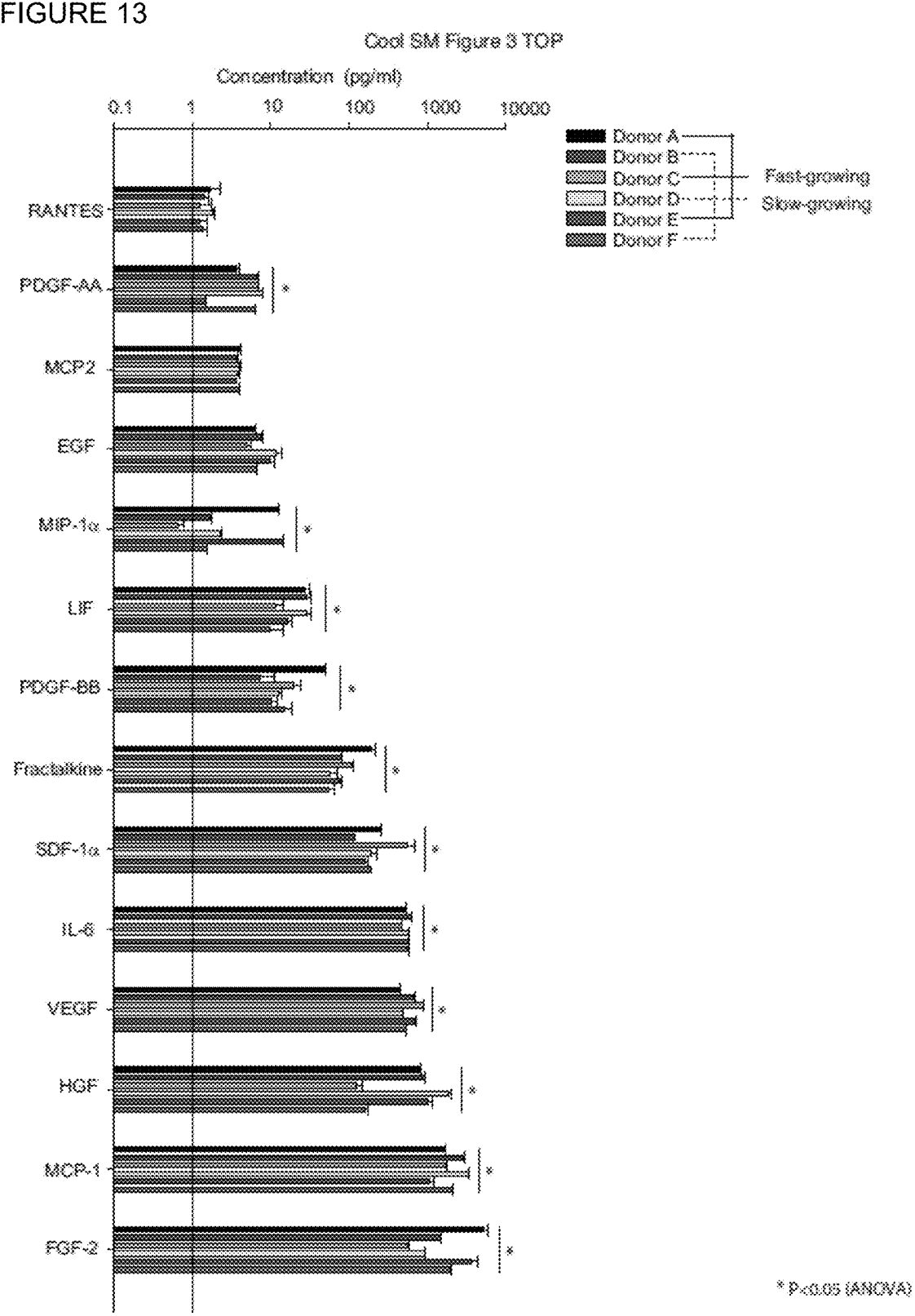
Figure 14:
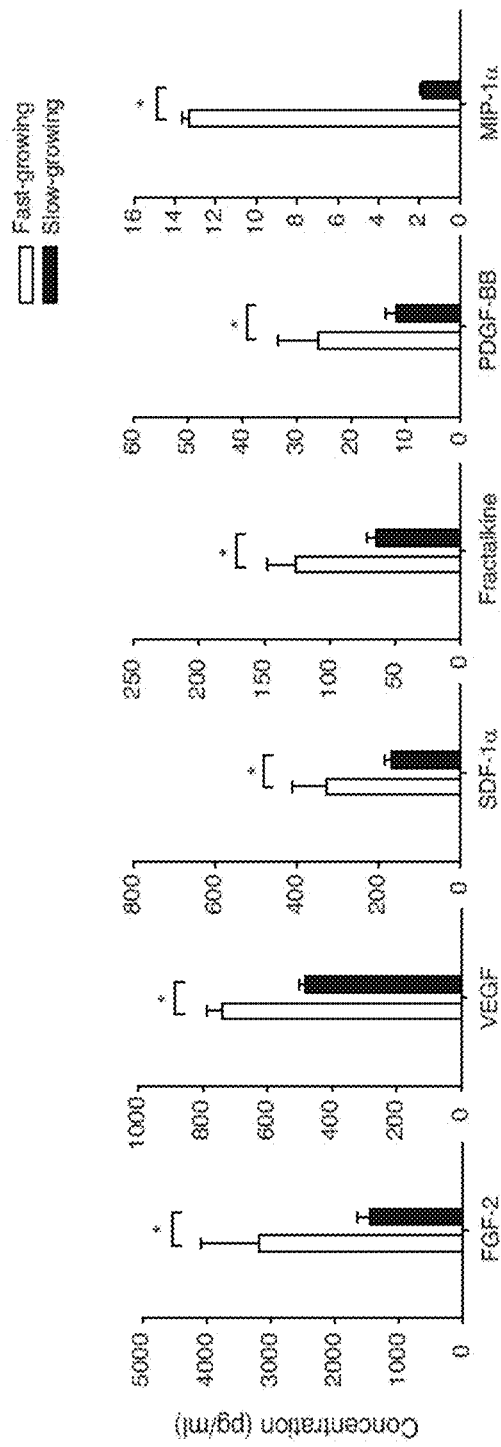

Levels of cytokines and growth factors produced by hMSCs were assayed as an indicator of possible in vivo efficacy. Significant donor variability was observed for majority of the growth factors. Fibroblast growth factor-2 (FGF-2) was the most highly secreted factor (500-6000 pg/ml) (FIG. 13), followed by MCP-1 which is known to play important roles in both cell migration and angiogenesis. PDGF-BB, a central connector between cellular components and contributors of the osteoblast differentiation program (Caplan and Correa, 2011), was at levels significantly greater than those of PDGF-AA. Overall, when grouping the factors based on growth it is notable that the amounts of FGF-2, VEGF, SDF-1α, fractalkine, PDGF-BB, and MIP-1α were significantly higher in fast growing hMSCs (FIG. 14). It is notable that key factors involved in wound healing such as mitogenic factor FGF-2, pro-angiogenic molecule VEGF, chemokines SDF-1α and fractalkine, pro-inflammatory chemokine MIP-1α, and PDGF-BB—a potent angiogenic, mitogenic and chemotactic factor—are upregulated in fast-growing cells. Our results highlight the importance of assaying the levels of these growth factors which could be central to predicting in vivo efficacy of hMSCs, and thus serve as key parameters that facilitate MSC selection for potential clinical use.

2.6 Immunosuppression of Activated T-Cells

Peripheral blood mononuclear cells (PBMCs) from whole adult blood were obtained using Ficoll-Paque PLUS (GE Healthcare). CD4+ T-cells were isolated from PBMCs using EasySep negative selection human CD4+ T cell enrichment kit (Stem Cell Technologies, Canada) and labeled with carboxy-fluorescein diacetate succinimidyl ester (CFSE; Vybrant® CFDA SE cell tracer kit). CD4+ CFSE+ cells ($0.5-1\times10^5$) were stimulated by anti-CD3 and anti-CD28 MACSiBeads (Miltenyi Biotec, Germany) at a ratio of four beads per T cell, to which hMSCs were added at different T cell:MSC ratios and incubated at 37° C. Proliferation of CD4+ CFSE+ cells was measured after 7 days by flow cytometry and the percentage inhibition of T cell proliferation by hMSCs was determined.

2.6.1 Immunosuppressive Ability of hMSCs

Figure 21:
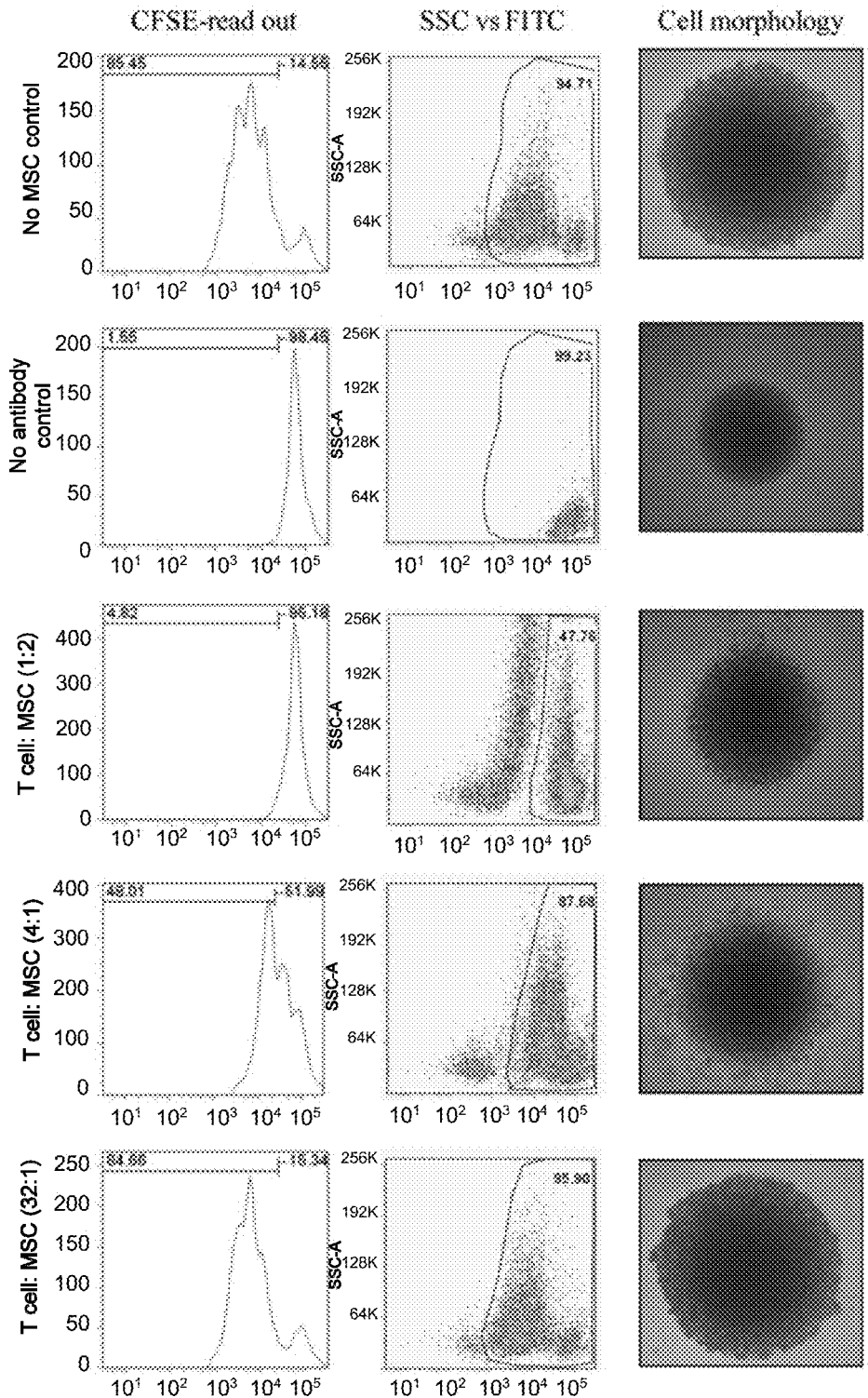

To test the ability of MSCs to secrete immunomodulatory factors capable of suppressing ongoing immune responses by virtue of an inhibition of T-cell proliferation in either mixed-lymphocyte culture or under mitogenic stimulation, cells from one representative from both the fast-growing (donor A), and slow-growing (donor F) pools were examined (FIG. 21; Table 2). Analysis of cell divisions via flow cytometry showed that T cell proliferation under antibody stimulation was suppressed by hMSCs in a dose-dependent manner (FIG. 15). At a T cell:MSC ratio of 32:1, no suppression was observed, and the percentage of cells proliferating under such conditions were equal to that of the 'no hMSC' control group. Inhibition was the highest at the 1 T cell: 2 hMSC ratio, with the proliferation percentage comparable to T cell growth without antibody stimulation. The fast-growing hMSCs consistently showed significantly greater suppression of T cells (*P<0.05). Notably, fast-growing hMSCs consistently showed significantly higher suppression of T cells (*P<0.05). This functional assay of immunosuppression highlights the supremacy of fast-growing cells in being efficacious for therapy.

Table 2.

Dose-dependent suppression of T cell proliferation. T cells and hMSC were co-cultured in varying proportions. A ratio of $:1 (T cell:hMSC) resulting in 50% suppression of T cell proliferation.

| T cell:hMSC ratio | Proliferation of T cells in co-culture with hMSCs (%) | |
|---|---|---|
| | Fast-growing (Donor A) | Slow-growing (Donor F) |
| 1:2 | 5.42 | 4.96 |
| 1:1 | 7.49 | 18.1 |
| 2:1 | 21.34 | 34.51 |
| 4:1 | 47.92 | 58.53 |
| 8:1 | 68.4 | 73.77 |
| 16:1 | 79.3 | 82.41 |
| 32:1 | 85.26 | 83.45 |

2.7 Gene Expression Studies

2.7.1 Quantitative Real Time Polymerase Chain Reaction (PCR):

Total RNA was isolated using the Nucleospin RNA II kit (Macherey Nagel, Bethlehem, PA) according to the manufacturer's instructions and quantified by NanoDrop™ 1000 (Thermo Fisher Scientific Inc.). After conversion to cDNA (Superscript VILO, Invitrogen Corporation, CA), expression of mesodermal genes TWIST-1 and DERMO-1, osteogenic markers RUNX2, ALP and BSP-II, adipogenic markers PPARγ and CEBPα and chondrogenic genes COL2A1 and SOX9 was assessed using the TaqMan® Gene Expression assay on an Applied Biosystems 7500 Fast Real Time PCR System (Table 3). $C_T$ values were normalized to β-actin and results plotted as relative expression units (REU).

TABLE 3

TaqMan® Gene Expression assays for real-time PCR

| Gene Symbol | Target gene | Context sequence | Assay ID | Amplicon length |
|---|---|---|---|---|
| RUNX2 | runt-related transcription factor 2 | TCGGGAACCCAGA AGGCACAGACAG | Hs00231692_m1 | 116 |
| ALP | alkaline phosphatase, liver/bone/ kidney | TACAAGCACTCCC ACTTCATCTGGA | Hs01029144_m1 | 79 |
| BSP II (IBSP) | integrin-binding sialoprotein | TCCAGTTCAGGGC AGTAGTGACTCA | Hs00173720_m1 | 95 |

TABLE 3-continued

TaqMan® Gene Expression assays for real-time PCR

| Gene Symbol | Target gene | Context sequence | Assay ID | Amplicon length |
|---|---|---|---|---|
| PPARγ | peroxisome proliferator-activated receptor gamma | TCTCATAATGCCAT CAGGTTTGGGC | Hs01115513_m1 | 90 |
| CEBPα | CCAAT/enhancer binding protein (C/EBP), alpha | TCGTGCCTTGTCAT TTTATTTGGAG | Hs00269972_s1 | 77 |
| TWIST-1 | twist homolog 1 | GCCGGAGACCTAG ATGTCATTGTTT | Hs00361186_m1 | 115 |
| DERMO-1 | twist homolog 2 | ACGTGCGCGAGCG CCAGCGCACCCA | Hs02379973_s1 | 154 |
| COL2A1 | collagen, type II, α1 | TGGTCTTGGTGGA AACTTTGCTGCC | Hs00264051_m1 | 124 |

2.7.2 Microarray and Gene Ontology Analysis:

RNA extracted at P5 was amplified for microarray using a TotalPrep RNA amplification kit according to the manufacturer's instructions (Ambion Inc., USA). The resulting purified biotin-labeled complementary RNA (cRNA) was normalized and hybridized onto a HumanHT-12 version 4 beadchip (Illumina Inc., USA) using its direct hybridization assay facility. The chip was then washed, blocked and Cy3-streptavidin bound to the hybridized cRNA. An Illumina BeadArray Reader using the Illumina BeadScan software was used to image the chip and the image data was converted into expression profile by GenomeStudio (Illumina Inc., USA). Background was subtracted and the data was submitted to GeneSpring (Agilent, USA). The replicates were averaged and a pairwise analysis was done followed by Student's-test unpaired statistical analysis with p<0.05 and fold change ≥1.5. Two donor samples representing each group with two technical replicates were analyzed. The gene lists generated were uploaded using Entrez gene ID onto DAVID for functional annotation clustering by GOTERM_BP_FAT with medium classification stringency. Only biological processes with p≤0.05 were considered.

2.7.3 Gene Expression Analysis

Figure 16B:
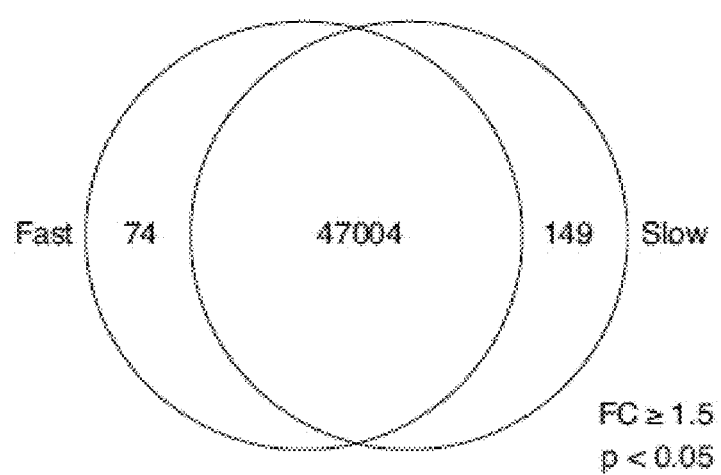
Figure 16C:
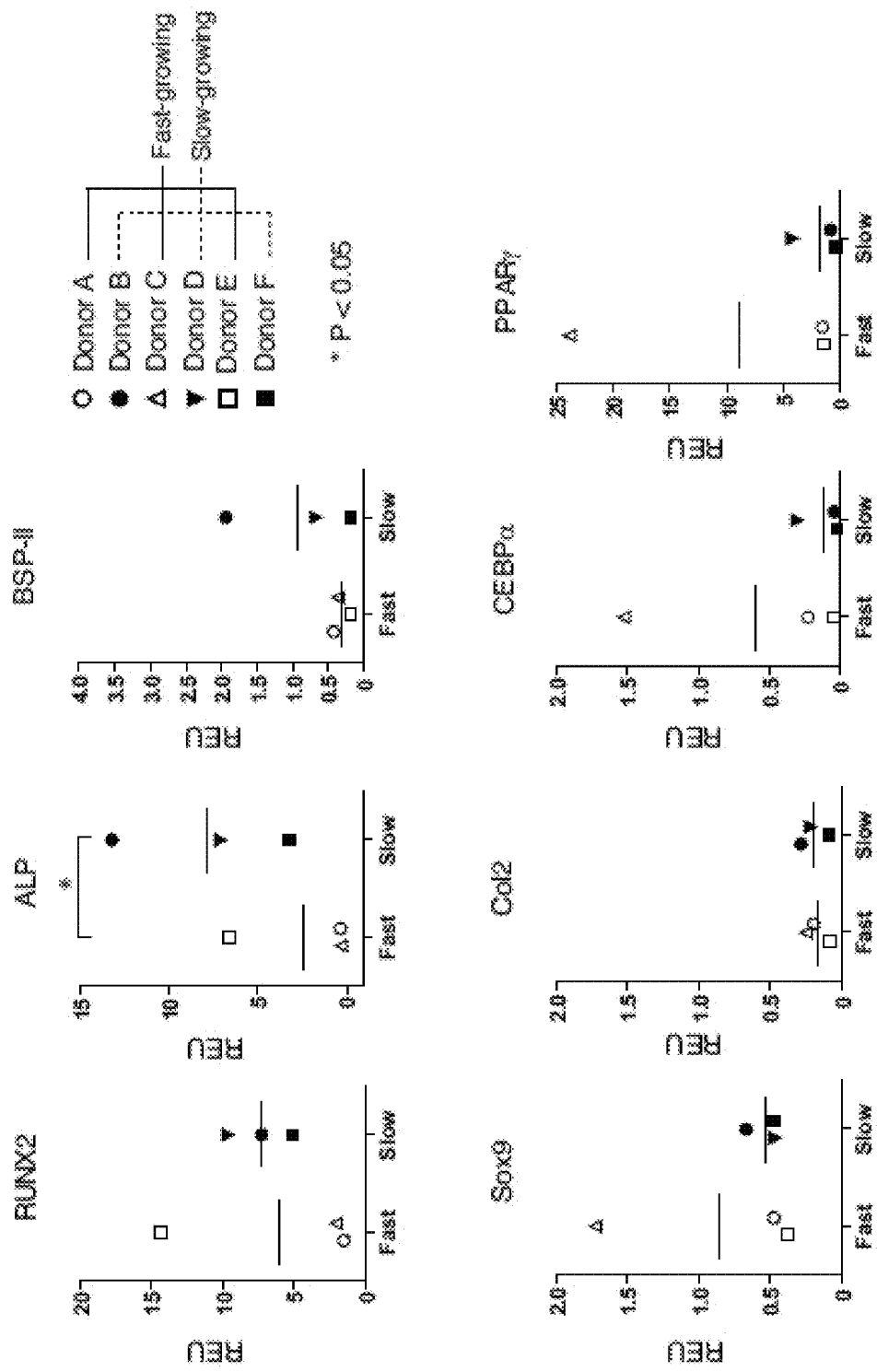

The phenotypic differences between the fast- and slow-growing cells may be due to systematic differences in gene expression. To identify such persistent differences at the transcriptome level, qPCR was done to check the levels of mesoderm-related markers Twist-1 and Dermo-1. Fast-growing hMSCs demonstrated higher transcript levels of these markers. Upon identifying such differences, a global gene expression analysis by microarray was performed on the two groups. A fold change cut-off of 1.5 and p-value <0.05 delineated a small set of transcripts differentially expressed between the two groups, with 74 significantly enriched in the fast-growers and 149 in the slow-growers (FIG. 16B). The limited size of the gene sets indicate that the two groups are largely similar, and that the trait variation could be attributed these genes.

Gene ontology (GO) analysis by DAVID functional annotation clustering was performed on the gene lists generated to identify biological processes enriched in the fast and slow groups. Genes regulating cell adhesion, the cytoskeleton and organelles were significantly upregulated (p-value ≤ 0.05) in the fast group (Table 4), with the latter indicative of a faster rate of turnover. Adhesion to the extracellular matrix and neighboring cells correlates with cell cycle progression (2,3). Genes enriched in the slow-growing cells tend to be cell morphogenetic and to do with development of mesenchyme-derived organs (Table 4).

Table 4.

Gene ontology (GO) analysis. GO analysis was performed using DAVID functional annotation terms (subset: GOTERM_BP_FAT) on the sets of genes enriched in fast-growing (Table 4A) and slow-growing hMSCs (Table 4B). Descendant GO terms are represented by the parent term.

TABLE 4A

Biological processes enriched in fast growers.

| GO ID | GO Description | p-value | Genes |
|---|---|---|---|
| GO:0051493 | Regulation of cytoskeleton organization | 0.008 | BRCA1, SKA3, PDGFA, SCIN |
| GO:0033043 | Regulation of organelle organization | 0.028 | BRCA1, SKA3, PDGFA, SCIN |
| GO:0007155 | Cell adhesion | 0.051 | TEK, CDH4, OPCML, OMD, PCDH19, THRA |

TABLE 4B

Biological processes enriched in slow growers.

| GO ID | GO Term | p-value | Genes |
|---|---|---|---|
| GO:0009991 | Response to extracellular stimulus | 0.002 | ALPL, BMP2, LEPR, LIPG, MGP, RBP4, SLC22A3 |
| GO:0001763 | Morphogenesis of a branching structure | 0.010 | BMP2, ERMN, EYA1, MGP |
| GO:0001501 | Skeletal system development | 0.012 | ALPL, BMP2, CYTL1, EYA1, MGP, OSR2, RBP4 |

TABLE 4B-continued

Biological processes enriched in slow growers.

| GO ID | GO Term | p-value | Genes |
|---|---|---|---|
| GO:0000902 | Cell morphogenesis | 0.020 | KAL1, S100A4, ANK1, BMP2, DCLK1, HGF, NRXN3 |
| GO:0042445 | Hormone metabolic process | 0.026 | CPE, DHRS9, HSD17B6, RBP4 |
| GO:0001656 | Metanephaors development | 0.028 | BMP2, EYA1, ITGA8 |
| GO:0001655 | Urogenital system development | 0.028 | BMP2, EYA1, ITGA8, RBP4 |
| GO:0060485 | Mesenchyme development | 0.039 | S100A4, BMP2, HGF |
| GO:0009611 | Response to wounding | 0.039 | BMP2, ENTPD1, SCG2, SERPINA1, SERPINA3, SERPINB2, TFPI, TNFAIP6 |
| GO:0022604 | Regulation of cell morphogenesis | 0.044 | ERMN, PALM, PALMD, RHOJ |

In order to investigate the upregulation/downregulation of genes involved in MSC differentiation, transcript levels of the markers were assayed under non-induced conditions by qPCR. Individual donors demonstrated variability in the baseline expression of these genes, however no significant differences in the tri-lineage differentiation markers were observed between the two groups.

2.8 In Vitro Multilineage Differentiation

Evaluation of the differentiation potential of hMSCs for the osteogenic, adipogenic, and chondrogenic lineages was performed as described previously (Rider et al, 2008). Average intensities of stained plates/wells were analyzed using Quantity One® software (Bio-Rad Laboratories), and recorded and expressed as relative intensity units, that is, fold-increase of intensity in treatment wells compared to their respective control wells. In these measurements, a darker stain implies higher density value.

2.8.1 Multilineage Differentiation Ability

Figure 17A:
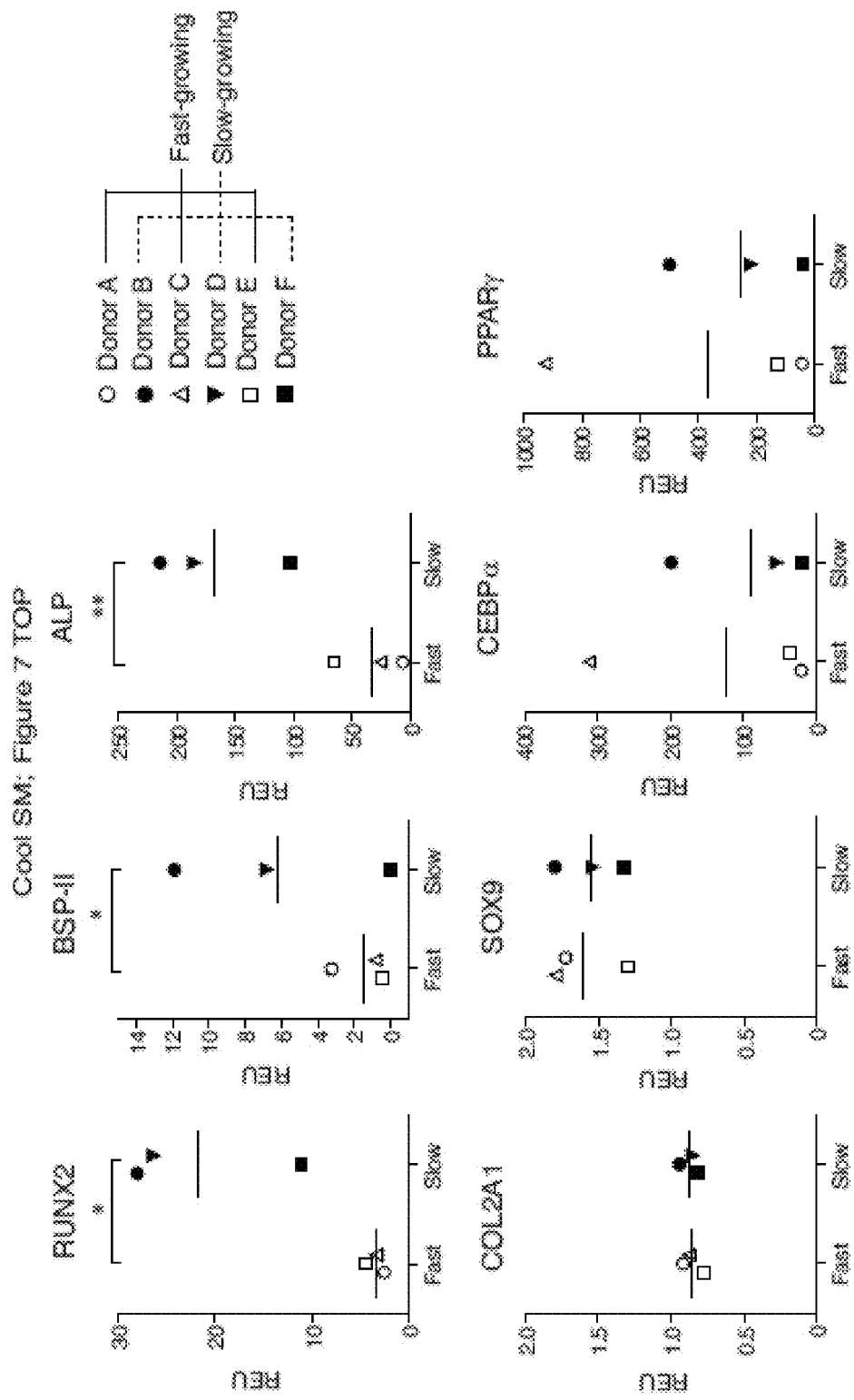
Figure 17B:
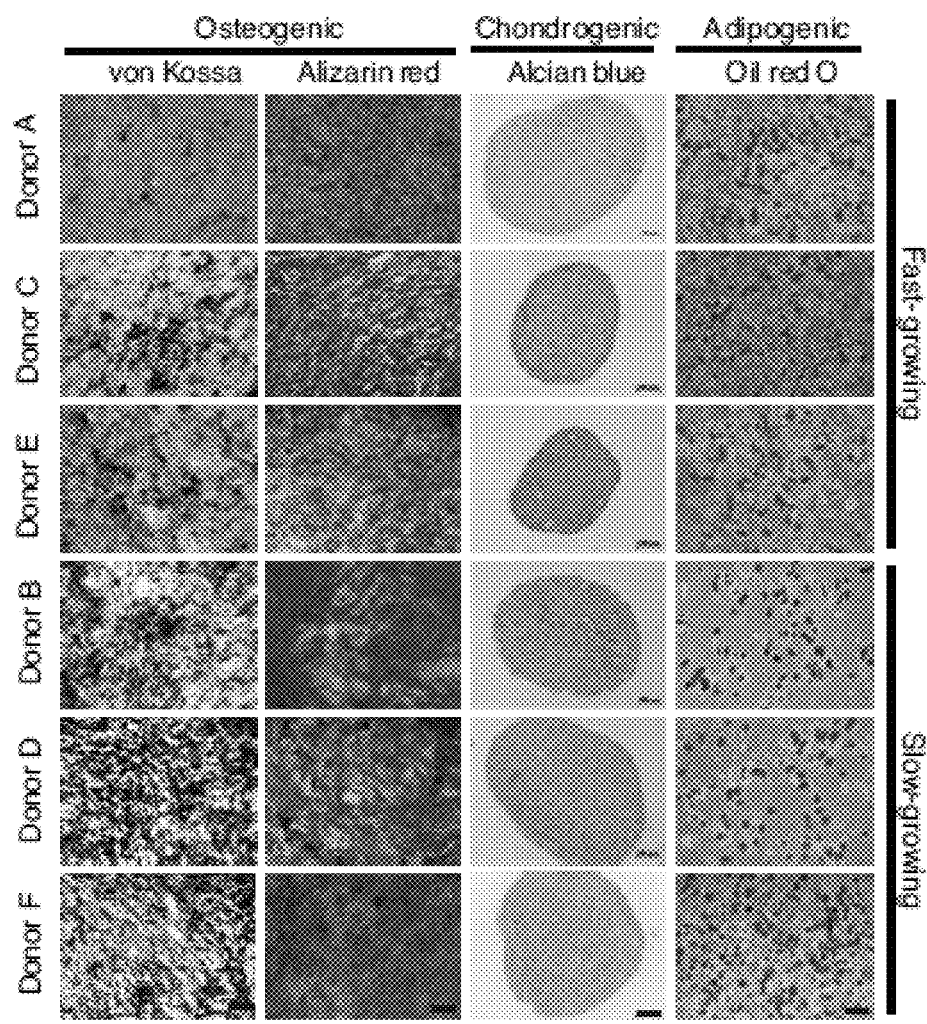
Figure 22:
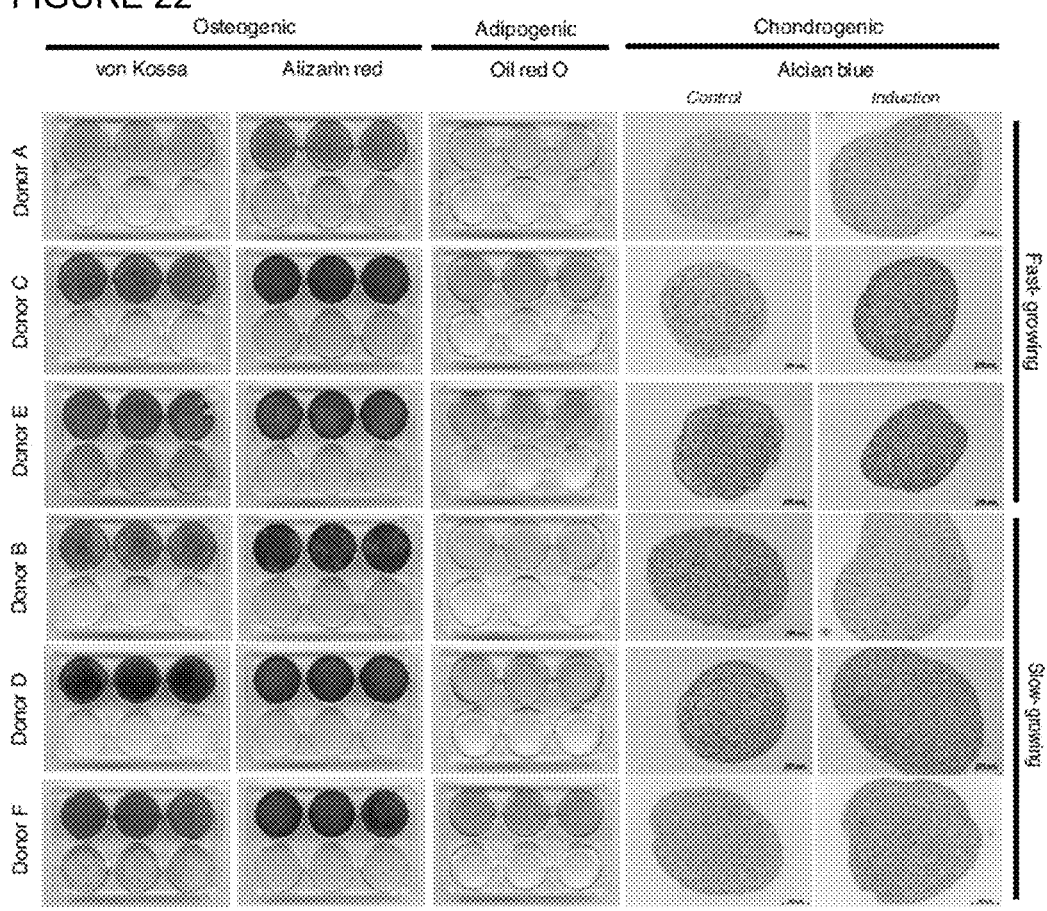
Figure 23:
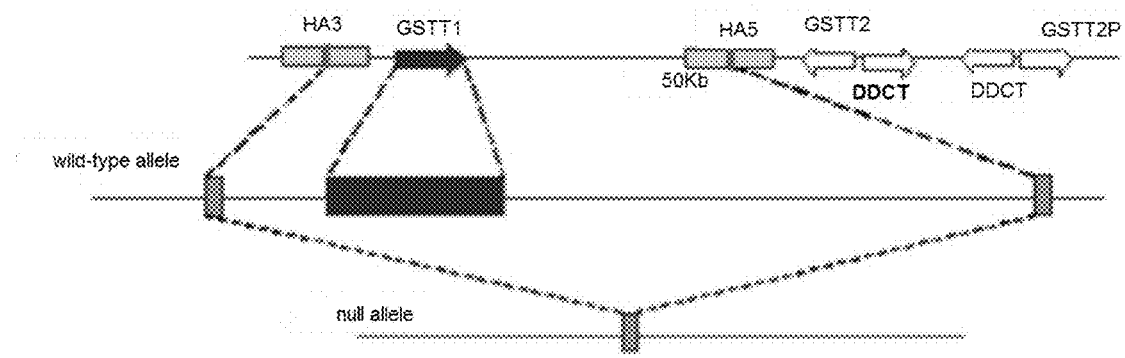

To assess the multipotency of the hMSCs, the cells were induced to differentiate down the osteogenic, adipogenic, and chondrogenic lineages by culturing them with defined media components and culture conditions (FIG. 22). All the donor hMSCs satisfied the minimal criteria to be designated as 'mesenchymal stem cells', as they could all both self-renew and differentiate, albeit with differing capacities. Fast-growing cells which had the highest proportion of potential precursors as evident from the TWIST and DERMO levels displayed variability associated with the expression of RUNX2, ALP, and CEBPα. High-expressing Twist-1 and Dermo-1 hMSCs were found to exhibit the most proliferative potential; thus higher expression of TWIST correlates with both decreased capacity for osteogenic differentiation and increased capacity for self renewal (FIG. 17A). Looking at a comparison of the means differences are observed, with no other significant effects noted. As the deposition of matrix is a more functional readout, the staining of the cell layers was analysed. Significant differences in calcium deposition under induced conditions between the fast and slow-growing cells was observed (FIGS. 17B,17C). It is notable that the ALP mRNA levels were correspondingly higher in slow-growing cells. This indicates that there is a possibility that these cells are already primed to differentiate down the osteogenic lineage. Certainly, for the bone lineage, the gene expression levels are tightly clustered among the fast-growing donors. Genes involved in adipogenesis showed upregulation of PPARγ and CEBPα in adipogenic cultures. Significant differences were not observed at the transcript levels but in the normalized staining intensity between the two groups of hMSCs (P<0.05) (FIG. 17C). In general, there was less variability among the fast-growing donors under osteogenic and chondrogenic differentiation. Under chondrogenic conditions, no differences were observed between the two groups.

Given that the differences may not be biologically relevant, it is notable that all the donors demonstrate tri-lineage differentiation potential. As our study focuses on identifying clinical correlates, our results on differentiation provided a fulsome assessment of a set of criteria for MSC identification. At this stage, this cannot be taken as sufficient evidence that fast-growing cells are better cells for differentiation, albeit their slight different efficiencies. Nevertheless, all individual donors demonstrated tri-lineage differentiation potential and have thus satisfied the ISCT criteria for the identification of MSCs.

2.9 Ectopic Bone Formation Assay

Ex-vivo passage 4 cells were expanded and ~3-5×10$^6$ seeded onto MasterGraft Matrix scaffolds (Medtronic, Inc. USA) before their implantation into subcutaneous pockets of 8 week-old immunodeficient mice (NIH-bg-nu-xid, Harlan Sprague-Dawley) as described previously (Zannentino et al, 2010). Surgeries were performed according to specifications of an ethics-approved small animal protocol (IACUC: #110651). X-rays were taken immediately post-transplantation and at 8 weeks using Shimadzu MobileArt MUX-101 Standard (Shimadzu Corporation, Japan) and a DÜRR MEDICAL—CR 35 VET Image Plate Scanner. Micro-CT was performed on the animals at weeks 4 and 8 using a SkyScan CT-Analyser, and datasets were reconstructed and analyzed by CTAn (SkyScan) and Mimics software to compute bone volume by applying appropriate threshold settings. Implants were recovered from the animals after 8 weeks, de-calcified, embedded in paraffin, and stained with hematoxylin/eosin and Rallis Trichrome. Immunohistochemistry was done by incubating tissue sections with appropriate concentrations of primary antibodies to mouse osteocalcin (M188, 1:100, Takara Bio Inc.), human osteocalcin (ab76690, 1:50, Abcam), mouse collagen I (NBP1-77458, 1:200, Novus Biologicals) or the same concentration of mouse IgG (MG100, Caltag Lab, USA; as negative controls) in blocking buffer overnight at 4° C. Sections were washed and incubated with rat-absorbed biotin-labeled antimouse IgG (Vector Lab Inc, USA) for 1 h, followed by the addition of avidin-biotin-peroxidase complex (ABC) solution (Immunopure ABC preoxidase staining kit, Vector Lab. Inc) for 1 h. Peroxidase activity was detected using 3,3-diaminobenzidiine-tetrahydrochloride (DAB; DAKO, USA). Sections were washed, mounted and examined under a Zeiss Axiolmager (Z1) upright microscope.

2.9.1 In Vivo Ectopic Bone Forming Efficacy of hMSCs

Figure 19B:
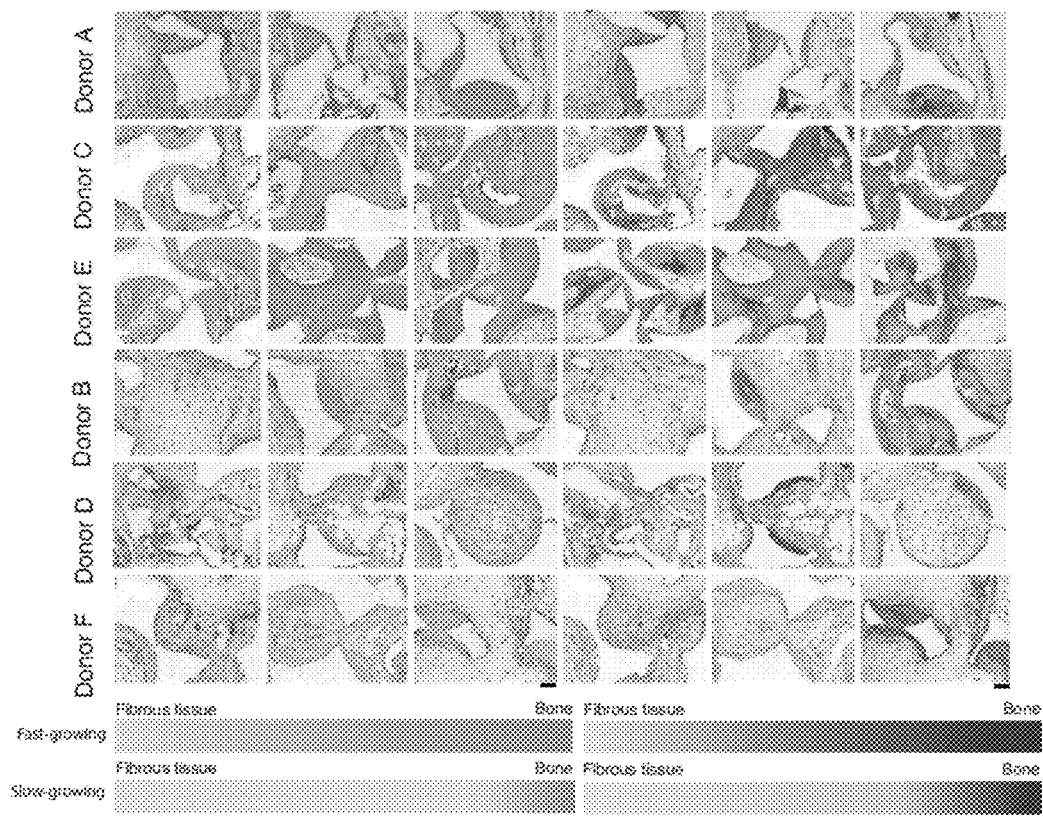

The in vitro characterization of hMSCs was followed by a functional in vivo assay. Amongst the most important assays for MSC efficacy is the ability to form bone after implantation at ectopic sites. MSCs from all donors demonstrated a capacity to form bone, albeit with significant variability in extent. Compiled analyses of the implants show that fast-growing hMSCs exhibited a two- to three-fold greater ability to form ectopic bone than the slow-growing, as quantified by μCT (FIGS. 18A-18E). Sections of implants stained with H&E and Rallis Trichrome showed the morphology, the extent of bone formation and fibrous tissue as indicated by the color gradient bar (FIG. 19B). Sections of the harvested implants were stained with species-specific antibodies against osteocalcin in order to determine whether the bone formed was of human or mouse origin. This enabled determination of whether transplanted hMSCs had differentiated into human osteoblasts to form bone at ectopic sites, or if they had supported host tissue to form bone. Immunohistochemical analysis revealed the presence of human osteocalcin at levels greater than mouse osteocalcin (FIG. 19A) Osteoblast-like cells observed to be depositing bone in the pores of the scaffold were of human origin as indicated by the staining for human osteocalcin. Donors A, C, and E triggered greater amounts of osteocalcin deposition than donors B, D, and F, correlating with the µCT analysis. Scaffolds with no hMSCs also revealed some bone deposition, in keeping with the osteoconductive property of the carrier. Mouse collagen was predominant in all the implants, with fast-growing hMSCs showing higher collagen 1 deposition than slow-growing cells.

All hMSC populations studied were able to display bone forming ability in vivo, albeit at different levels. Correlating in vitro parameters with the above in vivo results, hMSCs were found to exhibit increased proliferative potential, longer telomeres, and higher secretion levels of growth factors were more potent in forming bone at ectopic sites.

2.10 Conclusions

The correlation of in vitro and in vivo attributes of human bone-marrow derived mesenchymal stem cells revealed that cells from donors with high CFU-F efficiency are on average smaller in size, show increased growth, and have longer telomeres compared to slow-growing cells; biomarkers of multipotency (CD profiling) are similarly high in donors with a higher proportion of small-sized hMSCs; secretion of trophic factors FGF-2, VEGF, PDGF-BB, SDF-1α, fractalkine, is elevated in hMSCs showing enhanced proliferative potential, and that bone formation at a subcutaneous ectopic site is positively correlated with the transplantation of hMSCs in culture having higher secretion levels of trophic factors, higher proliferative potential, and relatively longer telomeres. Monitoring the benchmarks of FGF-2 levels, telomere length and growth rate described in this study should enable the selection of potent cells for therapy, saving time and resources involved in hMSC transplantation. Selection of hMSCs that show higher efficiency for the above characteristics should heighten in vivo efficacy. These findings lay the foundation for developing future strategies to direct and enhance the growth and developmental of culture expanded MSC for tissue engineering applications by enabling the selection of best-in-class hMSCs.

By correlating in vitro findings with the in vivo, the present inventors conclude that hMSCs with faster doubling times, a higher proportion of rapidly self-renewing cells with longer telomeres, and greater secretion levels of certain key growth factors, particularly FGF-2, VEGF, PDGF-BB, and SDF-1α, are more efficacious in vivo for the formation of new bone at ectopic sites. Somewhat paradoxically, fast-growing hMSCs that yielded the greater new bone formation displayed the least mineralization capacity in vitro. The enrichment of proliferation-associated and maturation-related processes in the fast and slow growers respectively suggests a physiological basis that may underpin their phenotypic divergence. As the BM-MSCs were derived and propagated from donors according to standardized procedures, with as minimal handling variation as possible, differences in the physiology of the cells might be due to this underlying transcriptome variation.

To date, no systematic correlation between the properties of hMSCs in vitro and their effects on treatment in vivo has been demonstrated, primarily because there is no universally accepted in vitro method for predicting the therapeutic capacity of MSCs (REF). A key study by Janicki et al. (2011), in attempts to provide clinically-relevant potency assays, demonstrated that the doubling time of hMSCs correlates well with in vivo bone formation; here the present inventors have greatly extended that concept to other in vitro parameters factors that correlate with ectopic tissue formation, including assays for mitogenic and cytokine factor secretion. Retrospectively analysis of the CFU-F efficiency of donors yielding fast-growing hMSCs, confirmed that hMSCs able to complete more than 15 cumulative population doublings within seven passages possessing a superior ability to induce bone formation in vivo.

It had been previously reported that rapidly self-renewing cells express higher levels of CXCR4 and CX3R1 for SDF-1α and fractalkine respectively (Lee et al., 2006), receptors implicated in haematopoiesis, vasculogenesis, and the efficient trafficking of immune cells, which were also observed. Rapidly self-renewing progenitor cells with increased expression of chemokine receptors are also known to engraft better into murine neurospheres (REF). The greater twist-1 and dermo-1 expression in the fast-growing hMSCs, genes known to be crucial for mesenchymal stem cell growth and development, also tend to corroborate the functional studies done by Isenmann et al. (2009), who demonstrated that such MSCs had a decreased capacity for osteogenic/chondrogenic differentiation and an enhanced tendency to undergo adipogenesis.

2.10.1 Correlating In Vitro hMSC Characteristics with In Vivo Efficacy

It is not known why hMSC growth is a predictor of outcome in the ectopic model, where osteoinductive growth factors, mechanical stimuli and a supporting bone-environment must also be in play. Perhaps high anabolism is needed to create an active, blood-rich microenvironment at the site of transplantation. Helledie et al. (2012) showed that hMSCs with longer telomeres survived longer when transplanted into critical-sized bone defects in nude rats.

In vitro, there were significant differences in the expression of osteogenic genes between fast- and slow-growing hMSCs. The slow-growing hMSCs showed better mineralization in vitro upon osteogenic induction, but were poor performers in vivo. This suggests that the high proliferation rate of a large fraction of MSCs within a population outcompeted the possible advantage yielded by the fraction of cells that may already have started to become osteoblasts. The deposition of bone in the scaffold pores suggests that the capacity to deposit a mineralised matrix is spatially controlled, and that the most adaptable hMSC to achieve this may be the faster proliferating, rather than slow-growing, pre-differentiated cells. That the standard in vitro osteogenic assay yields a poor prognosis is in accord with a previous study from our group, and with work others showing that ex vivo matrix mineralisation assays lack specificity, and show little or no concordance with true bone formation (Watson, 2004; Rai et al., 2010).

Fast-growing hMSCs consisted of a higher proportion of small-sized cells from within the heterogeneous population, with high clonogenicity and multipotentiality. This correlation is interesting as it connects three aspects of hMSC behaviour: secretion of trophic factors, proportion of RS cell subpopulations, and bone forming-efficacy.

Figures 15A, 15B:
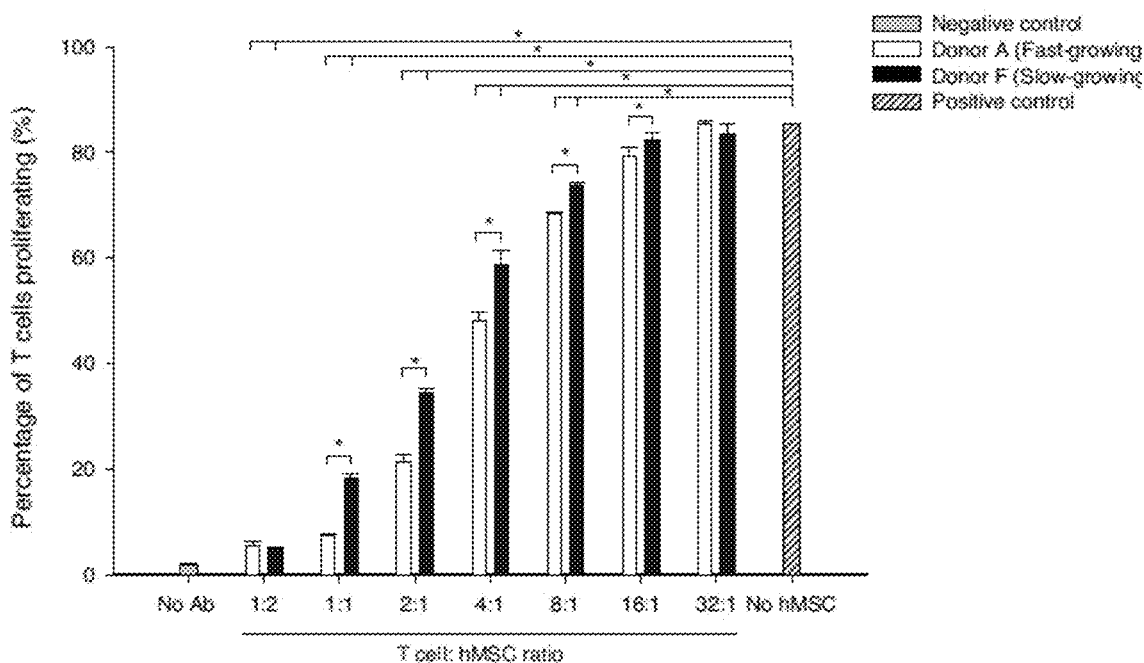

Among the many growth factors regulating bone metabolism, FGF-2 is recognized as a particularly potent mitogen for mesenchymal cells. It is produced by cells within the osteoblastic lineage, accumulates in bone matrix, and acts as an autocrine/paracrine factor for bone cells (REF). FGF-2 stimulation of osteoblast differentiation and bone formation is mediated in part by modulation of the Wnt pathway (Kasten et al., 2008; Fei et al., 2011). The exogenous application of FGF-2 has stimulatory effects on bone formation by facilitating BMP-2-induced ectopic bone formation, through alteration of the expression of BMPRs on the surface of bone-forming progenitor cells, an effect now thought to be the major pharmacological action of FGF-2 in vivo (Nakamura et al., 2005), and a plausible reason why hMSCs are better at giving rise to ectopic bone formation than pre-differentiated osteoblasts (FIG. 15B). VEGF belongs to the PDGF superfamily of growth factors, and is a key regulator of angiogenesis, a process crucial for all tissue healing (Zentilin et al., 2006; Schipani et al., 2009). VEGF also acts as a strong mitogenic stimulus for endothelial cells (Han et al., 2009), and osteoblasts (Hiltunen et al., 2003), as well as MSCs (Huang et al., 2010). The present inventors also demonstrate that VEGF was secreted by hMSCs; it is possible that the fast-growing cells produced superior bone in part because of their superior ability to stimulate of endothelial cell recruitment, as supported by the histology. Angiogenesis involves the recruitment of capillary-forming endothelial cells, that are in turn stimulated by pro-angiogenic factors to induce the further migration and proliferation of neovascularising cells (Abboud, 1993). As bone healing is closely associated with angiogenesis, the increases in levels of VEGF and MCP-1 correlate well with earlier reports (Zisa et al., 2009).

Despite the immense amount of work done over the last decade, MSCs are still relatively poorly understood, heterogenous cell mixtures with unpredictable properties. As pointed out by Mendicino et al. 2014 in their recent review, there is bewildering diversity in how sponsors have defined, manufactured, and described MSCs in their regulatory submissions to the US FDA, not only in terms of tissue sourcing, but also methods of in vitro propagation, cell surface marker expression and product manufacturing. They confirmed from their survey of FDA submissions that seven cell surface markers are routinely utilized for MSC-based product IND submissions (CD105, CD73, CD90, CD45, CD34, CD14, and HLA class II), which is consistent with the marker set specified by the ISCT in their 2006 position paper (Dominici et al., 2006 Cytotherapy 8: 315-317). However, it is clear that this marker set is far from definitive, and encompasses a vast majority of cells without true, "stem-like" qualities; it has recently been shown that special conditions are required in culture, including specific HS content, to maintain and even increase the fraction of bone marrow-derived adherent cells that are capable of true self-renewal (Helledie et al., 2012). Thus it is still an open question which particular set of markers truly describes this heterogeneous cell class.

MSC bioactivity may also be dependent on cues in the microenvironment, clinical indication, and route of administration. The most-targeted clinical indications for MSCs are cardiovascular, neurological, orthopaedic and metabolic disease, in particular diabetes. Nearly a quarter looking to ameliorate immune-mediated disease, particularly Graft versus Host Disease. Multiple routes of administration have been employed, including intravenous, direct injection (mostly cardiac) and topical application (REF). Proof-of-concept animal studies variably seek to monitor such complex aspects of cell behaviour as phenotype, proliferative ability, distribution, and survival post-administration, and even combinations thereof, despite the lack of convincing means to assess exactly how the cells are exerting their biological activity.

It seems clear that more work of the kind described here will be needed to better understand the phenotypic stability and impact of subpopulations on MSC-based therapies. This may be even more true for non-bone marrow-derived MSC-based therapies, where even less information is available. Markers predictive of therapeutic benefit can be expected to yield multiplicative effects for the clinical translation of MSC-based products.

Example 3—Development of Techniques Based on GSTT1

3.1 Developing a Biomarker Kit—Designing a Test for GSTT1 Genotype for Use in Clinical Settings An affordable PCR diagnostic kit will be designed to detect the 2 major GSTT1 alleles, wildtype and the GSTT1 deletion allele.

The simplest, fastest and cheapest means will be to adopt a diagnostic test to the TaqMan RT-PCR platform, which is widely used in the diagnostics community. RT-PCR primers will be designed for both alleles that will work well in this TaqMan format. For commercialization considerations, the kit will be optimized for use with peripheral blood drawn from prospective donors.

The kit will be versatile and able to start with DNA extracted from the non-adherent cells from bone marrow preparations typically discarded during the isolation of MSC. Primers and probes will be selected that have suitable properties (e.g. annealing temperature) for use with the TaqMan platform.

10-20 primer pair combinations will be designed using an optimised primer design algorithm, and tested for ability to detect GSTT1 alleles. The best pairs will then be tested pair wise to identify a suitable matched set for use in multiplex format for the detection of GSTT1 alleles in a single reaction.

A simple DNA-based kit has been designed, which allows screening of patients or prospective donors for the presence or absence of GSTT1 before making a decision on whether or not to harvest stem cells.

Various tissues can be utilized to detect the presence or absence of GSTT1 such as buccal swabs, blood and skin punches. The kit will be used primarily to test cells harvested from buccal swabs of consenting donors. Depending on tissue availability, other tissue materials will also be considered as an alternative to buccal swabs.

Genomic DNA (gDNA) will be extracted from samples using standard extraction procedures. Primers designed by Buchard et al. for detecting the copy number of the GSTT1 gene will be utilized to probe the gDNA samples (FIG. 24)—see Buchard et al. et al., J Mol Diagn, (2007) 9(5): 612-617:

| Primer set | Forward Primer | Reverse Primer |
|---|---|---|
| GSTT1_Gene | 5'-TCTTTTGCATAGAGACCATGACCAG-3' | 5'-CTCCCTACTCCAGTAACTCCCGACT-3' |
| GSTT1_Deletion | 5'-GAAGCCCAAGAATGGGTGTGTGTG-3' | 5'-TGTCCCCATGGCCTCCAACATT-3' |

Figure 24:
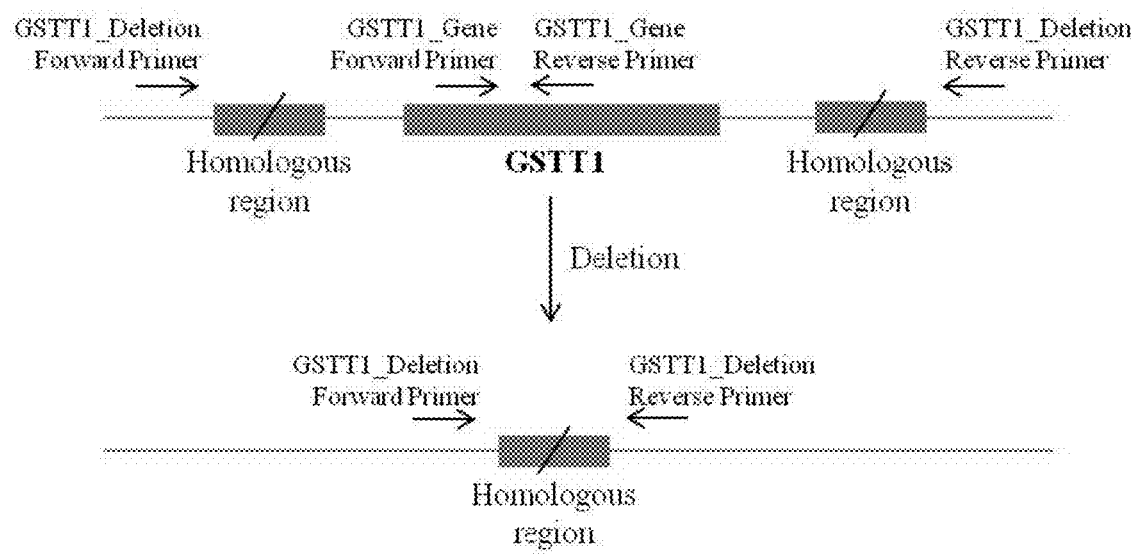

The "GSTT1_Deletion" primer set, hybridizes to specific sequences adjacent to the homologous regions flanking both GSTT1 (FIG. 24). When the GSTT1 gene is deleted, these primers will amplify a ~3 Kb product, as the deletion brings the hybridization sites for the primers into close enough proximity for PCR amplification. The "GSTT1_gene" primer set is specific to a segment of the GSTT1 sequence, and will amplify a 1 Kb product when the gene is present (i.e. not deleted):

GSTT1+/+: 1 kb band only
GSTT1+/−: 1 kb band and 3 kb band
GSTT1+/+: 3 kb band only In a multiplex PCR assay, the primer enable us the genotype of the donors to be determined. Therefore, the copy number of GSTT1 in patients and donors can be identified, enabling pre-selection of individuals null for the biomarker for stem cell isolation. This could save time and resources in generating quality stem cells for cell-based therapies. The application of these selectively isolated stem cells can also have better efficacy for such clinical purposes.

3.2 Assessing Stem Cell Quality In Vitro

Stem cell donors will be screened for GSTT1 genotype, and GSTT1 genotype will be correlated with stem cell phenotype.

a. Bone Marrow Aspiration:

Bone marrow aspirates (30 ml) will be obtained from iliac crests of ten normal healthy adult donors (n=10) under local anaesthesia, using a Jamshidi needle under, after informed consent and following standard protocols.

b. Isolation of MSCs:

Bone marrow aspirate will be layered on Ficoll and centrifuged at 2000 rpm for 20 min. The mononuclear cell fraction will be aseptically transferred to tissue culture plates and incubated at 37° C., 5% $CO_2$ until colonies of adherent cells are formed. The nonadherent cell population will be collected, and DNA isolated for the verification of the GSTT1 status using the biomarker kit according to 3.1. c. MSC characterization: Isolated MSCs from the multiple donors will be characterized individually by the following methods;

(i) Colony Efficiency—

CFU-Fs will be assayed by plating the different MSC preparations (0.5-2 million bone marrow mononuclear cells per T75 flask), and culturing them for 14 days. Colonies with more than 50 cells (not in contact with other colonies) will be scored.

(ii) Proliferation—

Cumulative cell numbers up to passage 10 will be determined by ViaCount assay using the Guava PCA-96 Base System as per the manufacturer's instructions (Millipore).

(iii) Cell-Surface Antigen Marker Expression—

Cells will be lifted using TrypLE™ and washed. Approximately, $1 \times 10^5$ cells will be incubated with antibodies (CD73, CD90, CD105, STRO-1, SSEA-4, CD-19, CD34, CD45, CD14, and HLA-DR) and analyzed on a BD FACSArray Bioanalyzer. All samples will be measured in triplicates.

(iv) Multilineage Differentiation—

MSCs will be phenotypically assessed for their ability to either deposit a bone-like matrix, form fat-laden droplets or secrete glycosaminoglycans when stimulated with osteogenic, adipogenic or chondrogenic supplements. In parallel cultures, total RNA will be isolated and the levels of mRNA transcripts for TWIST-1, DERMO-1, together with other major osteogenic, adipogenic and chondrogenic biomarkers normalized to β-ACTIN.

(v) Telomere Length—

Chromosomal DNA will be isolated and then precipitated, washed, dried and quantified. DNA (12.5 ng) will be used for amplification of telomeric repeats by real time quantitative PCR (RQ-PCR), in triplicate. Relative expression of telomeric repeats will be estimated from standard curves (Ct vs. log quantity) made from chromosomal DNA isolated from the human embryonic stem cell line BG01V (Invitrogen).

3.3 Assessment of Stem Cell Quality In Vivo in an Ectopic Bone Formation Model

Bone-healing potential of MSCs characterised as in 3.2 will be correlated with GSTT1 genotype in a clinically-relevant murine an ectopic bone formation model.

Ectopic Bone Formation Assay

TABLE 5

Experimental groups for ectopic bone formation assay

| Experimental Groupds (6 implants/group) | Method | Dose of MSCs |
|---|---|---|
| 1 | MasterGraft Matrix (vehicle only) | 0 |
| 2-11 | MasterGraft Matrix + MSC (Donor 10) cultured in basal media | $3 \times 10^6$ |

(i) Animal Species:

Immunodeficient 8 week-old female beige mice (NIH-bg-nu-xid) will be used as recipients for subcutaneous transplants.

(ii) Cell and Scaffold Preparation:

Ex vivo expanded, passage 4 MSCs (under maintenance conditions) from donors will be lifted by 0.125% trypsin/versene and resuspended in maintenance medium before seeding onto the MastertGraft® Matrix scaffold (Medtronic, Inc. USA). The MastertGraft® Matrix scaffold is a collagen sponge containing 15% HA/80% β-TCP ceramic particles. The scaffold will be cut into cubes of dimensions 3×3×3 mm (27 mm³) using surgical scalpels, under sterile conditions. Approximately 3-5 million osteoblasts will be seeded on to the cut scaffolds and incubated for 1 h at 37° C. prior to implantation. The scaffold and cells will be held together with a fibrin clot, generated with 15 μl of mouse thrombin (100 U/ml in 2% $CaCl_2$; Sigma-Aldrich®, USA) and 15 μl of mouse fibrinogen (30 mg/ml in PBS; Sigma-Aldrich®, USA).

(iii) Surgery:

Operations will be performed according to specifications of an ethics-approved small animal protocol IACUC: #110651 (pending renewal). Mid-longitudinal skin incisions of 0.5 cm will made on the dorsal surface of each mouse, and subcutaneous pockets formed by blunt dissection. A single implant will be placed into each pocket with two implants per animal. Incisions will be closed with surgical staples. Each transplant and the corresponding control transplant, will be implanted under the same conditions (n=6).

(iv) Methods of Analysis:

The extent of new bone formation will be analyzed by X-rays, micro-CT, and histology. X-rays will be taken on the day of surgery immediately after transplantation and after 8 weeks.

Micro-CT will be performed on the animals at weeks 4 and 8 using a SkyScan μCT-Analyser. Reconstructed images will be analyzed using Mimics software to compute the total bone volume by applying appropriate threshold settings set for each component. For histological analyses, sections of 5

μm thickness will be cut from the middle and either end of each 3-4 mm implant using a rotary microtome (Leica Microsystems, Germany). The paraffin sections will be placed on positively charged microscope slides, dried, stained with H&E and Rallis Trichrome, and finally examined under Zeiss Axiolmager (Z1) upright microscope. For immunohistochemistry analysis, tissue sections will be incubated with appropriate concentrations of primary antibodies to mouse osteocalcin, human osteocalcin, mouse collagen I or the same concentration of mouse IgG. Sections will be incubated with rat absorbed biotinlabeled anti-mouse IgG (Vector Lab Inc, USA), incubated with avidin-biotin-peroxidase complex (ABC) solution (Immunopure ABC preoxidase staining kit, Vector Lab. Inc) for 1 h. Peroxidase activity will be detected using 3,3-diaminobenzidiine-tetrahydrochloride (DAB; DAKO, USA).

TABLE 6

Experimental plan

| Experimental Group | X-ray (0, 4, 8 weeks) | MIcroCT (4, 8 weeks) | Histology (8 weeks) |
|---|---|---|---|
| MasterGraft Matrix (vehicle only) | 6 of 6 implants imaged | 6 of 6 implants imaged | 6 of 6 implants stained |
| MasterGraft Matrix + MSC (Donor 10) cultured in basal media | 60 of 60 implants imaged | 60 of 60 implants imaged | 60 of 60 implants stained |

3.4 Assessment of Strategies for Modulating GSTT1 and Determining Effect on Stem Cell Quality The effects of modulating GSTT1 levels on in vitro MSCs via siRNA and small molecule inhibitors will be investigated.

Given their importance, GSTs have become active targets for drug discovery, particularly for cancer and inflammatory diseases. Preliminary data indicates that the expression of GSTT1 directly impacts the proliferation rates of MSCs. Small molecule inhibitors of GSTT1 will be identified, MSCs will be treated with the inhibitors prior to transplantation, and whether it is possible to bestow bone-forming ability on GSTT1 wild-type cells will be assessed.

GST inhibitors will be obtained from commercial sources and tested in vitro on GSTT1-expressing MSCs for their effects on proliferation. A series of established assays will be used, which will reveal differential activities within GSTT1+ and GSTT1−/− MSCs, including clonogenic potential (colony-forming activity), cell proliferation (the xCELLigence system), and growth rates (EdU labelling). Selected GSTT1 inhibitors will then be tested for their influence on MSC cytokine expression profiles, immunophenotype, and multipotency in vitro.

It is also possible to target its downstream signaling pathways of GSTT1. Preliminary data indicate that p38 MAPK regulates GSTT1 expression (data not shown). The p38 MAPK may therefore be a key regulator of MSC proliferation, and bone-forming activity. Selective targeting of this pathway to enhance the regenerative potential of MSC may therefore be possible. Which cytokines are influenced by GSTT1 will be investigated, as will the mechanism of action, using molecular and pharmacological tools. GSTT1 will be over-expressed in null cells, and changes in cytokine expression will be investigated. Similarly, GSTT1 expression will be knocked-down by shRNA in wildtype MSCs, and subsequent changes in growth, signal transduction, phenotype and cytokine production will be investigated. Such perturbation studies will inform understanding of cytokine expression, and provide the means to explore underlying signaling pathways operating in the presence/absence of GSTT1.

Statistical Justification for the Sample Size and the Means by which Data Will be Analyzed and Interpreted.

Cell-Based Assays—

All experiments will be performed with three independent repeats. The mean values and standard deviations will be computed. Analysis of variance (ANOVA) will be utilised to assess the level of significant difference between the experimental groups, followed by Tukey post hoc testing where appropriate. All statistical analysis will be performed using SPSS V 12.0 software (SPSS, Inc. Chicago, USA). The difference will be considered significant if $p \leq 0.05$.

The invention claimed is:

1. A method for selecting a stem cell donor, the method comprising:
 (a) determining the genotype for GSTT1 in a DNA-containing sample isolated from an individual, and selecting as the stem cell donor an individual determined to have a GSTT1 genotype which is known, and/or which would be predicted, to result in decreased expression of GSTT1 relative to individuals homozygous for wildtype; or
 (b) determining the level of GSTT1 expression by a stem cell or plurality of stem cells in a sample isolated from an individual, and comparing the determined level of GSTT1 expression to a reference value for the level of GSTT1 expression for that stem cell type, and selecting as the stem cell donor an individual determined to have a stem cell or plurality of stem cells having decreased GSTT1 expression relative to the reference value,
 the method further comprising separating and/or isolating a stem cell or plurality of stem cells from the individual selected as a stem cell donor, wherein the stem cell or plurality of stem cells separated and/or isolated from the individual selected as the stem cell donor is a mesenchymal stem cell (MSC) or plurality of MSCs obtained from the bone marrow of the individual selected as a stem cell donor.

2. The method according to claim 1, wherein the stem cell or plurality of stem cells additionally possess one or more of the following characteristics as compared to a reference population of stem cells:
 (i) enhanced colony forming capacity;
 (ii) reduced cell size;
 (iii) increased telomere length and/or a reduced rate of telomere shortening;
 (iv) increased expression of STRO-1, SSEA-4, CD146 and/or PDGFRβ;
 (v) increased secretion of FGF-2, VEGF, SDF-1α, fractalkine, PDGF-BB and/or MIP-1α;
 (vi) enhanced suppression of T cells;
 (vii) decreased expression of ALP, RUNX2 and/or BSP-II; and
 (viii) increased expression of TWIST-1 and DERMO-1.

3. The method according to claim 1, wherein determining the genotype for GSTT1 in a DNA-containing sample isolated from an individual comprises detecting the presence of a wildtype GSTT1 allele, a GSTT1 allele which is known and/or which would be predicted to result in decreased expression of GSTT1 relative to the wildtype GSTT1 allele, and/or a GSTT1 null allele.

4. The method according to claim 3, wherein the method of detecting the presence of a wildtype GSTT1 allele, a GSTT1 allele which is known and/or which would be predicted to result in decreased expression of GSTT1 relative to the wildtype GSTT1 allele, and/or a GSTT1 null allele comprises contacting the DNA-containing sample with one or more oligonucleotide primers suitable for use to detect the presence of a wildtype GSTT1 allele, a GSTT1 allele which is known and/or which would be predicted to result in decreased expression of GSTT1 relative to the wildtype GSTT1 allele and/or a GSTT1 null allele.

5. The method according to claim 4, wherein the one or more oligonucleotide primers comprise one of more of 5'-TCTTTTGCATAGAGACCATGACCAG-3' (SEQ ID NO:12), 5'-CTCCCTACTCCAGTAACTCCCGACT-3' (SEQ ID NO:13), 5'-GAAGCC-CAAGAATGGGTGTGTGTG-3' (SEQ ID NO:14) and 5'-TGTCCCCATGGCCTCCAACATT-3' (SEQ ID NO:15).

* * * * *